US007153655B2

(12) United States Patent
Borrebaeck et al.

(10) Patent No.: US 7,153,655 B2
(45) Date of Patent: Dec. 26, 2006

(54) METHOD FOR IN VITRO MOLECULAR EVOLUTION OF PROTEIN FUNCTION INVOLVING THE USE OF EXONUCLEASE ENZYME AND TWO POPULATIONS OF PARENT POLYNUCLEOTIDE SEQUENCE

(75) Inventors: Carl Arne Krister Borrebaeck, Hjarup (SE); Ann-Christin Malmborg-Hager, Helsingborg (SE); Christina Furebring, Lund (SE); Ulf Hans Eskil Soderlind, Sòdra Sandby (SE); Rebecka Ingrid Camilla Ottosson, Lund (SE)

(73) Assignee: Alligator Bioscience AB, Lund (SE)

(*) Notice: Subject to any disclaimer, the term of this patent is extended or adjusted under 35 U.S.C. 154(b) by 547 days.

(21) Appl. No.: 10/321,195

(22) Filed: Dec. 17, 2002

(65) Prior Publication Data
US 2003/0148353 A1 Aug. 7, 2003

Related U.S. Application Data

(63) Continuation-in-part of application No. 09/445,649, filed as application No. PCT/GB98/01757 on Jun. 16, 1998, now Pat. No. 6,495,321.

(51) Int. Cl.
C12Q 1/68 (2006.01)
C12P 19/34 (2006.01)
(52) U.S. Cl. .................. 435/6; 435/91.1; 435/91.2
(58) Field of Classification Search .............. 435/6, 435/91.1, 91.2
See application file for complete search history.

(56) References Cited

U.S. PATENT DOCUMENTS

| | | | |
|---|---|---|---|
| 4,683,202 A | 7/1987 | Mullis et al. |
| 4,888,286 A | 12/1989 | Crea |
| 4,994,368 A | 2/1991 | Goodman et al. |
| 5,023,171 A | 6/1991 | Ho et al. |
| 5,043,272 A | 8/1991 | Hartley et al. |
| 5,223,408 A | 6/1993 | Goeddel et al. |
| 5,252,479 A | 10/1993 | Srivastava |
| 5,270,170 A | 12/1993 | Schatz et al. |
| 5,338,665 A | 8/1994 | Schatz et al. |
| 5,491,074 A | 2/1996 | Aldwin et al. |
| 5,498,530 A | 3/1996 | Schatz et al. |
| 5,512,463 A | 4/1996 | Stemmer |
| 5,514,568 A | 5/1996 | Stemmer |
| 5,521,291 A | 5/1996 | Curiel et al. |
| 5,573,907 A | 11/1996 | Carrino et al. |
| 5,605,793 A | 2/1997 | Stemmer |
| 5,712,089 A | 1/1998 | Borrebaeck et al. |
| 5,723,323 A | 3/1998 | Kauffman et al. |
| 5,733,731 A | 3/1998 | Schatz et al. |
| 5,733,753 A | 3/1998 | Jørgensen |
| 5,763,192 A | 6/1998 | Kauffman et al. |
| 5,798,208 A | 8/1998 | Crea |
| 5,811,238 A | 9/1998 | Stemmer et al. |
| 5,814,476 A | 9/1998 | Kauffman et al. |
| 5,817,483 A | 10/1998 | Kauffman et al. |
| 5,824,514 A | 10/1998 | Kauffman et al. |
| 5,830,650 A | 11/1998 | Crea |
| 5,830,696 A | 11/1998 | Short |
| 5,830,721 A | 11/1998 | Stemmer et al. |
| 5,834,252 A | 11/1998 | Stemmer et al. |
| 5,837,458 A | 11/1998 | Minshull et al. |
| 5,858,657 A | 1/1999 | Winter et al. |
| 5,858,725 A | 1/1999 | Crowe et al. |
| 5,871,907 A | 2/1999 | Winter et al. |
| 5,925,544 A | 7/1999 | Jørgensen |
| 5,928,905 A | 7/1999 | Stemmer et al. |
| 5,939,250 A | 8/1999 | Short |
| 5,965,408 A | 10/1999 | Short |
| 5,969,108 A | 10/1999 | McCafferty et al. |
| 5,976,862 A | 11/1999 | Kauffman et al. |
| 6,096,548 A | 8/2000 | Stemmer |
| 6,117,679 A | 9/2000 | Stemmer |
| 6,132,970 A | 10/2000 | Stemmer |
| 6,143,527 A | 11/2000 | Pachuk et al. |
| 6,153,410 A | 11/2000 | Arnold et al. |
| 6,156,511 A | 12/2000 | Schatz et al. |
| 6,159,687 A | 12/2000 | Vind |
| 6,159,688 A | 12/2000 | Borchert et al. |
| 6,159,690 A | 12/2000 | Borrebaeck et al. |
| 6,165,793 A | 12/2000 | Stemmer |

(Continued)

FOREIGN PATENT DOCUMENTS

EP 0 368 684 A 5/1990

(Continued)

OTHER PUBLICATIONS

Alber, et al., "Contributions of hydrogen bonds of Thr 157 to the thermodynamic stability of phage T4 lysozyme", Nature 330: 41-46 (1987).

(Continued)

Primary Examiner—Kenneth R. Horlick
(74) Attorney, Agent, or Firm—Dann Dorfman Herrell and Skillman; Kathleen D. Rigaut; Robert C. Netter, Jr.

(57) ABSTRACT

The present invention relates to a method for in vitro evolution of protein function. In particular, the method relates to the shuffling of nucleotide segments obtained from exonuclease digestion. The present inventors have shown that polynucleotide fragments derived from a parent polynucleotide sequence digested with an exonuclease can be combined to generate a polynucleotide sequence which encodes for a polypeptide having desired characteristics. This method may be usefully applied to the generation of new proteins (e.g., antibodies and enzymes) or parts thereof having modified characteristics as compared to the parent protein.

35 Claims, 16 Drawing Sheets

U.S. PATENT DOCUMENTS

| | | |
|---|---|---|
| 6,171,820 B1 | 1/2001 | Short |
| 6,177,263 B1 | 1/2001 | Arnold et al. |
| 6,180,406 B1 | 1/2001 | Stemmer |
| 6,238,884 B1 | 5/2001 | Short et al. |
| 6,251,674 B1 | 6/2001 | Tobin et al. |
| 6,265,201 B1 | 7/2001 | Wackett et al. |
| 6,277,638 B1 | 8/2001 | Stemmer |
| 6,287,861 B1 | 9/2001 | Stemmer et al. |
| 6,287,862 B1 | 9/2001 | delCardayre et al. |
| 6,291,165 B1 | 9/2001 | Borchert et al. |
| 6,291,242 B1 | 9/2001 | Stemmer |
| 6,291,650 B1 | 9/2001 | Winter et al. |
| 6,297,053 B1 | 10/2001 | Stemmer |
| 6,303,344 B1 | 10/2001 | Patten et al. |
| 6,309,883 B1 | 10/2001 | Minshull et al. |
| 6,319,713 B1 | 11/2001 | Patten et al. |
| 6,319,714 B1 | 11/2001 | Crameri et al. |
| 6,323,030 B1 | 11/2001 | Stemmer |
| 6,326,204 B1 | 12/2001 | delCardayre et al. |
| 6,326,206 B1 | 12/2001 | Bjornvad et al. |
| 6,329,178 B1 | 12/2001 | Patel et al. |
| 6,335,160 B1 | 1/2002 | Patten et al. |
| 6,335,179 B1 | 1/2002 | Short |
| 6,335,198 B1 | 1/2002 | delCardayre et al. |
| 6,337,186 B1 | 1/2002 | Krebber |
| 6,344,356 B1 | 2/2002 | Stemmer |
| 6,352,842 B1 | 3/2002 | Short et al. |
| 6,352,859 B1 | 3/2002 | delCardayre et al. |
| 6,355,484 B1 | 3/2002 | Patten et al. |
| 6,358,709 B1 | 3/2002 | Short et al. |
| 6,358,712 B1 | 3/2002 | Jarrell et al. |
| 6,358,740 B1 | 3/2002 | Patten et al. |
| 6,358,742 B1 | 3/2002 | Stemmer |
| 6,361,974 B1 | 3/2002 | Short et al. |
| 6,365,377 B1 | 4/2002 | Patten et al. |
| 6,365,408 B1 | 4/2002 | Stemmer |
| 6,368,798 B1 | 4/2002 | Short |
| 6,368,805 B1 | 4/2002 | Borchert et al. |
| 6,368,861 B1 | 4/2002 | Crameri et al. |
| 6,372,497 B1 | 4/2002 | Stemmer |
| 6,376,246 B1 | 4/2002 | Crameri et al. |
| 6,379,964 B1 | 4/2002 | del Cardayre et al. |
| 6,387,702 B1 | 5/2002 | Stemmer |
| 6,391,552 B1 | 5/2002 | Stemmer |
| 6,391,640 B1 | 5/2002 | Minshull et al. |
| 6,395,547 B1 | 5/2002 | Stemmer |
| 6,399,383 B1 | 6/2002 | Apt et al. |
| 6,406,855 B1 | 6/2002 | Patten et al. |
| 6,406,910 B1 | 6/2002 | Patten et al. |
| 6,413,745 B1 | 7/2002 | Patten et al. |
| 6,413,774 B1 | 7/2002 | Stemmer et al. |
| 6,420,175 B1 | 7/2002 | Stemmer |
| 6,423,542 B1 | 7/2002 | Crameri et al. |
| 6,426,224 B1 | 7/2002 | Crameri et al. |
| 6,429,004 B1 | 8/2002 | Murphy et al. |
| 6,436,675 B1 | 8/2002 | Welch et al. |
| 6,440,668 B1 | 8/2002 | Short |
| 6,444,426 B1 | 9/2002 | Short et al. |
| 6,444,468 B1 | 9/2002 | Stemmer et al. |
| 6,479,258 B1 | 11/2002 | Short |
| 6,479,652 B1 | 11/2002 | Crameri et al. |
| 6,482,647 B1 | 11/2002 | Stemmer |
| 6,483,011 B1 | 11/2002 | Stemmer et al. |
| 6,489,145 B1 | 12/2002 | Short |
| 6,492,107 B1 | 12/2002 | Kauffman et al. |
| 6,635,449 B1 * | 10/2003 | Short ................ 435/69.1 |
| 6,709,841 B1 * | 3/2004 | Short ................ 435/69.1 |
| 6,939,689 B1 * | 9/2005 | Short et al. ........... 435/69.1 |
| 6,958,213 B1 * | 10/2005 | Carlsson et al. .......... 435/6 |
| 2001/0006950 A1 | 7/2001 | Punnonen et al. |
| 2001/0032342 A1 | 10/2001 | Stemmer et al. |
| 2001/0039014 A1 | 11/2001 | Bass et al. |
| 2001/0049104 A1 | 12/2001 | Stemmer et al. |
| 2001/0049125 A1 | 12/2001 | Stemmer et al. |
| 2002/0051976 A1 | 5/2002 | Patten et al. |
| 2002/0058249 A1 | 5/2002 | Subramanian et al. |
| 2002/0059659 A1 | 5/2002 | Stemmer |

FOREIGN PATENT DOCUMENTS

| | | |
|---|---|---|
| EP | 0 415 731 A | 3/1991 |
| EP | 0 456 304 A | 11/1991 |
| EP | 0557897 | 9/1993 |
| EP | 0 590 689 A | 4/1994 |
| FR | 2813314 | 3/2002 |
| GB | 9712512.4 | 6/1997 |
| JP | 10-66576 | 3/1998 |
| JP | 2000-308490 A | 11/2000 |
| JP | 2001-57893 A | 3/2001 |
| JP | 2001-197895 A | 7/2001 |
| WO | WO 86/05803 | 10/1986 |
| WO | WO 90/07936 | 7/1990 |
| WO | WO 90/14430 | 11/1990 |
| WO | WO/1991/007506 | 5/1991 |
| WO | WO/1991/015581 | 10/1991 |
| WO | WO/1991/016427 | 10/1991 |
| WO | WO/1992/007075 | 10/1991 |
| WO | WO 92/01047 | 1/1992 |
| WO | WO 92/15702 | 9/1992 |
| WO | WO/1992/018645 | 10/1992 |
| WO | WO 93/07282 | 4/1993 |
| WO | WO 93/08278 | 4/1993 |
| WO | WO/1993/006213 | 4/1993 |
| WO | WO 93/12257 | 6/1993 |
| WO | WO 94/12632 | 6/1994 |
| WO | WO 94/24313 | 10/1994 |
| WO | WO 94/28173 | 12/1994 |
| WO | WO 95/22625 | 8/1995 |
| WO | WO 96/05803 | 2/1996 |
| WO | WO 96/17056 | 6/1996 |
| WO | WO 96/40750 | 12/1996 |
| WO | WO 96/40987 | 12/1996 |
| WO | WO 97/07205 | 2/1997 |
| WO | WO 97/07206 | 2/1997 |
| WO | WO 97/08320 | 3/1997 |
| WO | WO 97/20078 | 6/1997 |
| WO | WO 97/35957 | 10/1997 |
| WO | WO 97/35966 | 10/1997 |
| WO | WO 98/01581 | 1/1998 |
| WO | WO 98/05765 | 2/1998 |
| WO | WO 98/13485 | 4/1998 |
| WO | WO 98/13487 | 4/1998 |
| WO | WO 98/25965 | 6/1998 |
| WO | WO 98/27230 | 6/1998 |
| WO | WO 98/28416 | 7/1998 |
| WO | WO 98/31837 | 7/1998 |
| WO | WO 98/32845 | 7/1998 |
| WO | WO 98/41622 | 9/1998 |
| WO | WO 98/41623 | 9/1998 |
| WO | WO 98/41653 | 9/1998 |
| WO | WO 98/42832 | 10/1998 |
| WO | WO 98/58080 | 12/1998 |
| WO | WO 99/21979 | 5/1999 |
| WO | WO 99/23107 | 5/1999 |
| WO | WO 99/23236 | 5/1999 |
| WO | WO 99/33965 | 7/1999 |
| WO | WO 99/41368 | 8/1999 |
| WO | WO 99/41369 | 8/1999 |
| WO | WO 99/41383 | 8/1999 |
| WO | WO 99/41402 | 8/1999 |
| WO | WO 99/45110 | 9/1999 |
| WO | WO 99/57128 | 11/1999 |
| WO | WO 99/58661 | 11/1999 |
| WO | WO 99/65927 | 12/1999 |

| | | |
|---|---|---|
| WO | WO 00/04190 | 1/2000 |
| WO | WO 00/09679 | 2/2000 |
| WO | WO 00/09727 | 2/2000 |
| WO | WO 00/12680 | 3/2000 |
| WO | WO 00/18906 | 4/2000 |
| WO | WO 00/20573 | 4/2000 |
| WO | WO 00/28008 | 5/2000 |
| WO | WO 00/28017 | 5/2000 |
| WO | WO 00/28018 | 5/2000 |
| WO | WO 00/34512 | 6/2000 |
| WO | WO 00/42559 | 7/2000 |
| WO | WO 00/42560 | 7/2000 |
| WO | WO 00/42561 | 7/2000 |
| WO | WO 00/46344 | 8/2000 |
| WO | WO 00/52155 | 9/2000 |
| WO | WO 00/53744 | 9/2000 |
| WO | WO 00/58517 | 10/2000 |
| WO | WO 00/61731 | 10/2000 |
| WO | WO 00/61740 | 10/2000 |
| WO | WO 00/72013 | 11/2000 |
| WO | WO 00/73433 | 12/2000 |
| WO | WO 00/77262 | 12/2000 |
| WO | WO 01/00234 | 1/2001 |
| WO | WO 01/02865 | 1/2001 |
| WO | WO 01/04287 | 1/2001 |
| WO | WO 01/12301 | 2/2001 |
| WO | WO 01/12791 | 2/2001 |
| WO | WO 01/23401 | 4/2001 |
| WO | WO 01/25438 | 4/2001 |
| WO | WO 01/27306 | 4/2001 |
| WO | WO 01/32712 | 5/2001 |
| WO | WO 01/34835 | 5/2001 |
| WO | WO 01/38504 | 5/2001 |
| WO | WO 01/38513 | 5/2001 |
| WO | WO 01/42455 | 6/2001 |
| WO | WO 01/46476 | 6/2001 |
| WO | WO 01/51663 | 7/2001 |
| WO | WO 01/64864 | 9/2001 |
| WO | WO 01/64912 | 9/2001 |
| WO | WO 01/68803 | 9/2001 |
| WO | WO 01/70947 | 9/2001 |
| WO | WO 01/73000 | 10/2001 |
| WO | WO 01/75087 | 10/2001 |
| WO | WO 01/75158 | 10/2001 |
| WO | WO 01/75767 | 10/2001 |
| WO | WO 01/96551 | 12/2001 |
| WO | WO 02/04629 | 1/2002 |
| WO | WO 02/10358 | 2/2002 |
| WO | WO 02/10750 | 2/2002 |
| WO | WO 02/16606 | 2/2002 |
| WO | WO 02/22663 | 3/2002 |
| WO | WO 02/29032 | 4/2002 |
| WO | WO 02/29071 | 4/2002 |
| WO | WO 02/38757 | 5/2002 |
| WO | WO 02/48351 | 6/2002 |

OTHER PUBLICATIONS

Arrizubieta, et al., "Increased Thermal Resistance and Modification of the Catalytic Properties of a β-Glucosidase by Random Mutagenesis and in Vitro Recombination", J. Biol. Chem., 275: 28843-8 (2000).
Barbas, et al., "Assembly of combinatorial antibody libraries on phage surfaces: The gene III site", Proc. Natl. Acad. Sci. USA, 88: 7978-7982 (1991).
Barbas, et al., "Semisynthetic combinatorial antibody libraries: A chemical solution to the diversity problem", Proc. Natl. Acad. Sci. USA, 89: 4457-4461 (1992).
Berger, et al., "Expanding the Potential of Restriction Endonucleases: Use of Hapaxoterministic Enzymes", Anal. Biochem. 222:1-8, (1994).
Boder & Wittrup, "Yeast surface display for screening combinatorial polypeptide libraries", Nature Biotechnol., 15: 553-557, (1997).
Boublik, et al., "Eukaryotic Virus Display: Engineering the Major Surface Glycoprotein of the Autographa californica Nuclear Polyhedrosis Virus (AcNPV) for the Presentation of Foreign Proteins on the Virus Surface", Biotechnol., 13: 1079-1084, (1995).
Brown, "Chapter 5: DNA and RNA Modifying Enzymes", Molecular Biology LabFax, BIOS Scientific Publishers Ltd., Oxford, pp. 154 (1991).
Buchholz, et al., "In vivo selection of protease cleavage sites from retrovirus display libraries", Nature Biotechnol. 16: 951-954, (1998).
Cadwell, et al., "Randomization of Genes by PCR Mutagenesis", PCT Methods Appl., 2:28-33, (1992).
Cadwell, et al., "Mutagenic PCR", PCT Methods Appl., 3:S136-140, (1994).
Casson & Manser, "Evaluationof Loss and Change of Specificity Resulting from Random Mutagenesis of an Antibody $V_H$ Region", J Immunol. 155: 5647-5654 (1995).
Chalfie, et al., "Green Florescent Protein as a Marker for Gene Expression", Science 263: 802-805 (1994).
Chang, et al., "Evolution of a cytokine using DNA family shuffling", Nature Biotech., 17: 793-797 (1999).
Chen, et al., "Tuning the activity of an enzyme for unusual environments: Sequential random mutagenesis of subtilisin E for catalysis in dimethylformamide", Proc. Natl. Acad. Sci. USA 90: 5618-5622 (1993).
Christians, et al., "Directed evolution of tymidine kinase for AZT phosphorylation using DNA family shuffling", Nature Biotech., 17: 259-264 (1999).
Crameri, et al., "Combinatorial Multiple Cassette Mutagenesis Creates All the Permutations of Mutant and Wild-Type Sequences", Biotechniques, 18: 194-196 (1995).
Crameri, et al., "Molecular evolution of an arsenate detoxification pathway by DNA shuffling", Nature Biotechnology, 15: 436-438, (1999).
Crameri, et al., "DNA shuffling of a family of genes from diverse species accelerates directed evolution", Nature, 391: 288-291 (1998).
Deng, et al., "Simultaneous randomization of antibody CDRs by a synthetic ligase chain reaction strategy", Nucl. Acid Res. 21: 4418-4419, (1993).
Dower, et al., "High efficiency transformation of E. coli by high voltage electroporation", Nucleic Acids Res. 16: 6127, (1988).
Eckstein, "Exogenous application of ribozymes for inhibiting gene expression", Ciba Found. Symp. 209: 207-217 (1997).
Engberg, et al., "Phage-Display Libraries of Murine and Human Antibody Fab Fragments", Molecular Biotechnology 6: 287-310 (1996).
Ernst, et al., "Baculovirus surface display: construction and screening of a eukaryotic epitope library", Nucleic Acids Res. 26: 1718-1723, (1998).
Fisch, et al., "A strategy of exon shuffling for making large peptide repertoires displayed on filamentous bacteriophage", Proc. Natl. Acad. Sci. USA 93: 7761-7766 (1996).
Gibbs, et al., "Degenerate oligonucleotide gene shuffling (DOGS): a method for enhancing the frequency of recombination with family shuffling", Gene 271: 13-20, (2001).
Giver, et al., "Directed evolution of a thermostable esterase", Proc. Natl. Acad. Sci. USA 95: 12809-12813, (1998).
Gram, et al., "In vitro selection and affinity maturation of antibodies from a naive combinatorial immunoglobulin library", Proc. Natl. Acad. Sci. USA 89: 3576-3580, (1992).
Grabherr, et al., "Expression of Foreign Proteins on the Surface of Autographa Californica Nuclear Polyhedrosis Virus", Biotechniques 22: 730-735, (1997).
Granzerio, et al., "Baculovirus cDNA libraries for expression of cloning genes encoding cell-surface antigens", J. Immunol. Metho. 203: 131-139, (1997).
Griffiths, et al., "Isolation of high affinity human antibodies directly from large synthetic repertoires", EMBO J., 13: 3245-3260, (1994).
Hanahan, "Studies on Transformation of Escherichia coli with Plasmids", Mol. Biol. 166: 557-580, (1983).

Hansson, et al., "Evolution of Differential Substrate Specificities in Mu Class Glutathione Transferases Probed by DNA Shuffling", J. Mol. Biol. 287: 265-276, (1999).

Henke & Bornscheuer, "Directed Evolution of an Esterase from Pseudomonas fluorescens. Random Mutagenesis by Error-Prone PCR or a Mutator Strain and Identification of Mutants Showing Enhanced Enantioselectivity by a Resorufin-Based Fluorescence Assay", Biol. Chem., 380: 1029-1033, (1999).

Higuchi, et al., "Cell display library for gene cloning of variable regions of human antibodies to hepatitis B surface antigen", J. Immunol. Meth., 202: 193-204, (1997).

Ho, et al., "Site-directed mutagenesis by overlap extension using the polymerase chain reaction", Gene 77: 51-59, (1989).

Hoogenboom, et al., "By-passing Immunisation: Human Antibodies from Synthetic Repertoires of Germline $V_H$ Gene Segments Rearranged in Vitro", J. Mol. Biol. 227: 381-388, (1992).

Horton, et al., "Engineering hybrid genes without the use of restriction enzymes: gene splicing by overlap extension", Gene, 77: 61-68, (1989).

Huse, et al., "Generation of a Large Combinatorial Library of the Immunoglobulin Repertoire in Phage Lambda", Science, 246: 1275-1281, (1989).

Jansen, et al., "Disruption of phase during PCR amplification and cloning of heterozygous target sequences", NAR, 18: 5153-5156, (1990).

Kikuchi, et al., "Novel family shuffling methods for the in vitro evolution of enzymes", Gene 236: 159-167, (1999).

Kikuchi, et al., "An effective family shuffling method using single-stranded DNA", Gene 243: 133-137, (2000).

Joern, et al., "Analysis of Shuffled Gene Libraries", J. Mol. Biol. 316: 643-656, (2002).

Kim, et al., "Bacterial Cell Surface Display of an Enzyme Library for Selective Screening of Improved Cellulase Variants", Appl. Environ. Microbiol., 66: 788-93, (2000).

Kobayashi, et al., "Analysis of Assembly of Synthetic Antibody Fragments: Expression of Functional scFv with Predefined Specificity", Biotechniques, 23: 500-503, (1997).

Kuipers, et al., "Improved site-directed mutagenesis method using PCR", Nucleic Acids Res. 19: 4558, (1991).

Kwekkeboom, et al., "CD40 plays an essential role in the activation of human B cells by murine EL4B5 cells", Immunol. 79: 439-444, (1993).

Kong, et al., "Directed Evolution of α-Aspartyl Dipeptidase from Salmonella typhimurium", Biochemical and Biophysical Research Communications, 289: 137-142, (2001).

Larrick, et al., "Rapid cloning of rearranged immunoglobulin genes from human hybridoma cells using mixed primers and the polymerase chain reaction", Biochem. Biophys. Res. Commun. 160: 1250-1256, (1989).

Leung, et al., "A method for random mutagenesis of a defined DNA segment using a modified polymerase chain reaction", Technique 1:11-15, (1989).

Lewin, "Genes IV", p. 272, Oxford University Press, (1990).

Lewis & Crowe, "Immunoglobulin complementary-determining region grafting by recombinant polymerase chain reaction to generate humanised monoclonal antibodies", Gene 101: 297-302 (1991).

Liu, et al., "Replacement and deletion mutations in the catalytic domain and belt region of Aspergillus awamori glucoamylase to enhance thermostability", Protein Eng. 13: 655-659 (2000).

Lu & Gray, "Kinetics and mechanism of BAL 31 nuclease action on small substrates and single-stranded DNA", Biochimica et Biophysica Acta, 1251: 125-138, (1995).

Luqmani & Lymboura, "Subtraction Hybridization Cloning of RNA Amplified From Different Cell Populations Microdissected From Cryostat Tissue Sections", Anal. Biochem., 222: 102-109, (1994).

Lutz, et al., "Rapid generation of incremental truncation libraries for protein engineering using α-phosphothioate nucleotides", Nucleic Acids Res. 29: E16, (2001).

Marks, et al., "By-passing immunization: building high affinity human antibodies by chain shuffling", Biotechnology, 10: 779-783, (1992).

May, et al., "Inverting enantioselectivity by directed evolution of hydantoinase for improved production of L-methionine", Nat. Biotechnol. 18: 317-320, (2000).

McCafferty, et al., "Phage antibodies: filamentous phage displaying antibody variable domains", Nature, 348: 552-554 (1990).

Meyerhans, et al., "DNA recombination during PCR", Nucl. Acid Res., 18: 1687-91, (1990).

Moore, et al., "Directed evolution of a para-nitrobenzyl esterase for aqueous-organic solvents", Nature Biotechnology, 14: 458-467 (1996).

Mottershead, et al., "Baculoviral Display of the Green Fluorescent Protein and Rubella Virus Envelope Proteins", Biochem. Biophys. Res. Com. 238: 717-722, (1997).

Orlandi, et al., "Cloning immunoglobulin variable domains for expression by the polymerase chain reaction", Proc. Natl. Acad. Sci. USA, 86: 3833-3837 (1989).

Ostermeier, et al., "A combinatorial approach to hybrid enzymes independent of DNA homology", Nature Biotech., 17: 1205-9, (1999).

Paabo, et al., "Ancient DNA and the Polymerase Chain Reaction", J. Biol. Chem., 264: 9709-9712, (1989).

Paabo, et al., "DNA Damage Promotes Jumping between Templates during Enzymatic Amplification", J. Biol. Chem., 265: 4718-4721, (1990).

Parmely, et al., "Antibody-selectable filamentous fd phage vectors: affinity purification of target genes", Gene 73: 305-318, (1988).

Prickett, et al., "A Calcium-Dependent Antibody for Identification and Purification of Recombinant Proteins", BioTechniques, 7: 580-589, (1989).

Roberts, et al., "Generation of an antibody with enhanced affinity and specificity for its antigen by protein engineering", Nature, 328: 731-734, (1987).

Schier R., et al., "Isolation of Picomolar Affinity Anti-c-erbB-2 Single-chain Fv by Molecular Evolution of the Contemporary Determining Regions in the Center of the Antibody Binding Site", J. Mol. Biol. 263: 551-567, (1996).

Schmidt, et al., "Exonuclease digestion of chromosomes for in situ hybridization", Nucl. Acid Research, 16: 10381, (1988).

Pelletier, "A RACHITT for our toolbox: A new twist on DNA shuffling increases recombination frequency and expands access to sequence space, facilitating the engineering of new protein activities", Nat. Biotechnol., 19: 314-315, (2001).

Schmidt-Dannert, et al., "Molecular breeding of carotenoid biosynthetic pathways", Nat. Biotechnol., 18: 750-753, (2000).

Shyur, et al., "Site-directed Mutagenesis of Residues at Subunit Interfaces of Procine Fructose-1,6-bisphosphatase", J. Biol. Chem., 271: 3005-3010, (1996).

Sock, et al., "DNA Replication of Human Polyomavirus JC Is Stimulated by NF-I in Vivo", Virology, 182: 298-308, (1991).

Söderlind, et al., "Domain libraries: Synthetic diversity for de novo design of antibody V-regions", Gene, 160: 269-272, (1995).

Song, et al., "Simultaneous Enhancement of Thermostability and Catalytic Activity of Phospholipase $A_1$ by Evolutionary Molecular Engineering", Appl. Environ. Microbiol. 66: 890-894, (2000).

Stemmer, "DNA shuffling by random fragmentation and reassembly: In vitro recombination for molecular evolution", Proc. Natl. Acad. Sci. USA, 91: 10747-51, (1994).

Stemmer, "Rapid evolution of a protein In vitro by DNA shuffling", Nature, 370: 389-391, (1994).

Vaish, et al., "In vitro selection of a purine nucleotide-specific hammerhead-like ribozyme", Proc. Natl. Acad. Sci. USA, 95: 2158-2162 (1998).

Volkov, et al., "Methods for in Vitro DNA Recombination and Random Chimeragenesis", Methods Enzymol., 328: 447-456 (2000).

Wan, et al., "In vitro evolution of horse heart myoglobin to increase peroxidase activity", Proc. Natl. Acad. Sci. USA, 95: 12825-12831 (1998).

Warren, et al., "A Rapid Screen of Active Site Mutants in Glycinamide Ribonucleotide Transformylase", Biochemistry, 35: 8855-8862 (1996).

Yang, et al., "CDR Walking Mutagenesis for the Affinity Maturation of a Potent Human Anti-HIV-1 Antibody into the Picomolar Range", J. Mol. Biol., 254: 392-403 (1995).

Zhang, et al., "Directed evolution of a fucosidase from a galactosidase by DNA shuffling and screening", Proc. Natl. Acad. Sci. USA, 94: 4504-4509, (1997).

Zhao & Arnold, "Directed evolution converts substilisin E into a functional equivalent of thermitase", Protein Eng., 12: 47-53, (1999).

Zhao, et al., "Molecular evolution by staggered extension process (StEP) in vitro recombination", Nat. Biotechnol. 16: 258-261 (1998).

Arnold FH, "Combinatorial and computational challenges for biocatalyst design", Nature (2001) 409:253-257.

Balint RF et al., "Antibody engineering by parsimonious mutagenesis", Gene (1993) 137(1):109-118.

Beaudry AA et al., "Directed evolution of an RNA enzyme", Science (1992) 257:635-641.

Berger SL et al., "Pheonix Mutagenesis: One-Step Reassembly of Multiply Cleaved Plasmids with Mixtures of Mutant and Wild-Type Fragments ", Analytical Biochemistry (1993) 214:571-579.

Berkhout B et al., "In vivo selection of randomly mutated retroviral genomes", Nucleic Acids Research (1993) 21(22) :5020-5023.

Blakely WF et al., "Radiation-induced binding of DNA from irradiated mammalian cells to hydroxyapatite columns", Radiant Research (1990) 121 (3) :338-343.

Bourgaux P et a., "Preferred crossover sites on polyomavirus DNA", Journal of Virology (1990) 64 (5) :2327-2336.

Casorati G et al., "The T cell receptor alpha beta V-J shuffling shows lack of autonomy between the combining site and the constant domain of the receptor chains", Eur. J. Immuno (1993) 23:586-589.

Chambers Dictionary of Science and Technology (1999), p. 995.

Clackson T et al., "Making antibody fragments using phage display libraries", Nature (1991) 352:624-628.

Crameri A, "Improved green fluorescent protein by molecular evolution using DNA shuffling", Nature Biotechnology (1996) 14:315-319.

Daugherty B et al., "Polymerase chain reaction facilitates the cloning, CDR-grafting, and rapid expression of a murine monoclonal antibody directed against the CD18 component of leukocyte integrins", Nucleic Acids Research (1991) 19(9) :2471-2476.

Demple B et al., "5,6-Saturated thymine lesions in DNA: production by ultraviolet light or hydrogen peroxide", Nucleic Acids Research (1982) 10(12) :3781-3789.

Dillon PJ et al., "A rapid method for the construction of synthetic genes using the polymerase chain reaction", BioTechniques (1990), 9 (3) :298-300.

Dimmock NJ et al., "Introduction to Modern Virology", 3$^{rd}$ Ed., Blackwell Scientific Publications, 1987.

Feinberg AP et al., "A technique for radiolabeling DNA restriction endonuclease fragments to high specific activity", Analytical Biochemistry (1983) 132:6-13.

Frappier D et al., "Alternative Homologous and Nonhomologous Products arising from Intramolecular Recombination", journal of Virology (1990) 64 (10) :5058-5065.

Perlak FJ, "Single step large scale site-directed in vitro mutagenesis using multiple oligonucleotides", Nucleic Acids Research (1990) 18 (24) :7457-7458.

Hall BG, "toward an understanding of evolutionary potential", FEMS Microbiology Letter (1999) 178:1-6.

Horton RM et al. "Gene splicing by overlap extension: tailor-made genes using the polymerase chain reaction", BioTechniques (1990) 8 (5) :528-535.

Horton RM et al., "Gene splicing by overlap extension", Methods Enzymol (1993) 217 :270-279.

Judo MSB et al. "Stimulation and suppression of PCR-mediated recombination", Nucleic Acids Research (1998) 26(7) :1819-1825.

Kauffman S et al., "Thinking combinatorially", Current Opinion in Chemical Biology (1999) 3:256-259.

Kaushansky K et al., "Structure-function relationships of interleukin-3. An analysis based on the function and binding characteristics of a series of interspecies chimera of gibbon and murine interleukin-3", J Clin Invest. (1992) 90(5) :1879-1888.

Krishnan BR et al., "Direct and crossover PCR amplification to facilitate Tn5supF-based sequencing of λ phage clones", Nucleic acids Research (1991) 19(22) :6177-6182.

Lassner M et al., "Directed molecular evolution in plant improvement", Current Opinion in Plant Biology (2001) 4:152-156.

Life: The Science of Biology, 3$^{rd}$ Ed. (1992), Sinauer Associates, p. 55.

Lewin B, "Genes III" (1987) , p. 722.

Lewin B, "Genes V" (1994) , p. 647.

Lowe G et al., "Oligoneric and biogenetic combinatorial libraries", Nat. Prod. Rep. (1999) 16:641-651.

Marks JF et al., "By-passing immunization human antibodies from V-gene libraries displayed in phage", J. Mol. Biol. (1991) 222:581-597.

Marton A et al., "DNA nicking favors PCR recombination", Nucleic Acids Research (1991) 19(9) :2423-2426.

McPherson IJ, "Directed Mutagenesis", Oxford Univ. Press, 1991.

Mello Filho AC et al. "In vivo formation fo single-strand breaks in DNA by hydrogen peroxide is mediated by the haber-weiss reaction", Biochim. Biophys. Acta (1984) 781:56-63.

Merz A et al., "Improving the catalytic activity of a thermophilic enzyme at low temperatures", Biochemistry (2000) 39:880-889.

Molecular Cell Biology, 3$^{rd}$ Ed., (1995), W.H. Freeman and Company, p. G-16.

Mouret JF et al., "Ionic and radiacal oxidations of DNA by Hydrogen Peroxide", Chem. Biol. Interact. (1991) 77(2) :187-201.

Mullis K et al., "Specific Enzymatic Amplification of DNA In Vitro: the Polymerase Chain Reaction", Spring harbor Symp., Quant. Biol. (1986) 51:263-273.

NCBI database entries (partial) for Homo sapiens insulin, myoglobin, L-selectin, rhodopsin kinase and complement component C3 mRNAs.

Near RI, "Gene Conversion of Immunoglobulin Variable Regions in Mutagenesis Cassettes by Replacement PCR Mutagenesis", Biotechniques (1992) 12(1) :88-97.

Ness JE et al., "DNA shuffling of subgenomic sequences of subtilisin", Nature Biotechnology (1999) 17:893-896.

Ness JE et al., "Molecular Breeding: the natural approach to protein design", Advances in Protein Chemistry (2001) 55:261-292.

Ørum H et al., "Efficient method for constructing comprehensive murine Fab antibody libraries displayed on phage", Nucleic Acids Research (1993) 21(19) :4491-4498.

Patten AP et al., "Applications of DNA shuffling to pharmaceuticals and vaccines", Current Opinion in Biotechnology (1997) 8:724-733.

Perlak FJ, "Single step large scale site-directed in vitro mutagenesis using multiple oligonucleotides", Nucleic Acids Research (199) 18(24) :7457-7458.

Povirk LF et al., "Oxidized apurinic/apyrimidinic sites formed in DNA by oxidative mutagens", Mutation Research (1989) 214:13-22.

Powell SK et al., "Breeding of retroviruses by DNA shuffling for improved stability and processing yields", Nature Biotechnology (2000) 18:1279-1282.

Prodromou C et al., "Recursive PCR: a novel technique for total gene synthesis", Protein Engineering (1992) 5:827-829.

Punnonen J, "Molecular Breeding of Allergy Vaccines and Antiallergic Cytokines", International Archives of Allergy Immunology (2000) 121:173-182.

Punnonen J et al., "Molecular Breeding by DNA Shuffling", Science & Medicine (2000) 121:38-47.

Rhaese HJ et al., "Chemical analysis of DNA alterations. I. Base liberation and backbone breakage of DNA and oligodeoxyadenylic acid induced by hydrogen peroxide and hydroxylamine", Biochim. Biophys. Acta (1968) 155:476-490.

Sagripanti JL et al., "Site-specific oxidative DNA damage at polyguanosines produced by copper plus hydrogen peroxide", Journal of Biological Chemistry (1989) 264(5) :1729-1734.

Saiki RK et al., "Primer-directed enzymatic amplification of DNA with a Thermostable DNA polymerase", Science (1988) 239(4839) :487-491.

Sambrook J et al., "Molecular Cloning" (1989) Chapters 16-18.

Shi XB et al., "Rapid PCR construction of a gene containing Lym-1 antibody variable regions", PCR Methods and Applications (1993) 3:46-53.

Shuldiner AR et al., "Hybrid DNA artifact from PCR of closely related target sequences", Nucleic Acids Research (1989) 17(11):4409.

Soogn NW et al., "Molecular breeding of viruses", Nature Genetics (2000) 25;436-439.

Suzuki DT et al., "An Introduction to Genetic Analysis", 4$^{th}$ Ed., W.H. Freeman and Company, p. 332.

Tobin MB et al., "Directed evolution: the 'rational' basis for 'irrational' design", Current Opinion in Structural Biology (2000) 10:421-427.

Weisberg EP et al., "Simultaneous mutagenesis of multiple sites: application of the ligase chain reaction using PCR products instead of oligonucleotides", Biotechniques (1993) 15(1):68-70, 72-74, 76.

Whalen RG et al., "DNA shuffling and vaccines", Current Opinions in Molecular therapeutics (2001) 3:31-36.

Zaphiropoulos PG et al., "Non-homologous revombination mediated by Thermus aquaticus DNA polymerase I. Evidence supporting a copy choice mechanism", Nucleic Acids Research (1998) 26(12):2843-2848.

Zoller MJ et al., "New recombinant DNA methodology for protein engineering", Current Opinion in biotech (1992) 3:348-354.

Horton RM et al. (1991), "Recombination and mutagenesis of DNA sequences using PCR", Directed Mutagenesis: A Practical Approach. M.J. McPherson, ed. IRL Press, Oxford, p. 217-247.

Malmborg, A-C., "Molecular libraries," website printout, 2 pages, www.immun.lth.se/texter/project mol-libraries.html (Dec. 8, 2005).

Henriquez, V., et al., "A simple strategy to generate small deletions using Bal31 nuclease," Nuc. Acids Res., 18:6735-6736, (1990).

Horton, R.M., et al., "Gene splicing by overlap extension," Methods in Enzymology, 317:270-279, (1993).

Brown, T.A., ed., Molecular Biology LabFax I: Recombinant DNA, Academic Press, San Diego, 128-129, (1998).

Ostermeier, M., et al., "Combinatorial protein engineering by incremental truncation," Proc. Natl. Acad. Sci. USA, 96:3562-3567, (1999).

Sharrocks, A., et al., "A rapid method for Bal31 deletion analysis," Nuc. Acids Res., 15:8564, (1987), (Abstract).

* cited by examiner

Figure 6A

CTAGCGCTATATGCGTTGATGCAATTTCTATGAGCACCCGTTCTCGGAGCACTGTCC
GACCGCTTTGGCCGCCGCCCAGTCCTGCTCGCTTCGCTACTTGGAGCCACTATCGAC
TACGCGATCATGGCGACCACACCCGTCCTGTGGATCCTCTACGCCGGACGCATCGTG
GCCGGCATCACCGGCGCCACAGGTGCGGTTGCTGGCGCCTATATCGCCGACATCACC
GATGGGGAAGATCGGGCTCGCCACTTCGGGCTCATGAGCGCTTGTTTCGGCGTGGGT
ATGGTGGCAGGCCCCGTGGCCGGGGACTGTTGGGCGCCATCTCCTTGCATGCACCA
TTCCTTGCGGCGGCGGTGCTCAACGGCCTCAACCTACTACTGGGCTGCTTCCTAATG
CAGGAGTCGCATAAGGGAGAGCGTCGACCGATGCCCTTGAGAGCCTTCAACCCAGTC
AGCTCCTTCCGGTGGGCGCGGGGCATGACTATCGTCGCCGCACTTATGACTGTCTTC
TTTATCATGCAACTCGTAGGACAGGTGCCGGCAGCGCTCTGGGTCATTTTCGGCGAG
GACCGCTTTCGCTGGAGCGCGACGATGATCGGCCTGTCGCTTGCGGTATTCGGAATC
TTGCACGCCCTCGCTCAAGCCTTCGTCACTGGTCCCGCCACCAAACGTTTCGGCGAG
AAGCAGGCCATTATCGCCGGCATGGC

Figure 6B

GAGCCACTATCGACTACGCGATCATGGCGACCACACCCGTCCTGTGGATCCTCTACG
CCGGACGCATCGTGGCCGGCATCACCGGCGCCACAGGTGCGGTTGCTGGCGCCTATA
TCGCCGACATCACCGATGGGGAAGATCGGGCTCGCCACTTCGGGCTCATGAGCGCTT
GTTTCGGCGTGGGTATGGTGGCAGGCCCCGTGGCCGGGGACTGTTGGGCGCCATCT
CCTTGCATGCACCATTCCTTGCGGCGGCGGTGCTCAACGGCCTCAACCTACTACTGG
GCTGATTCCTAATGCAGGAGTCGCATAAGGGAGAGCG

Figure 7A

CCGTTNAAGNNNACACAGTTANATTGTTAANGCAGTCAGGCACCGTGTATGAAATC
TAACAATGCGCTCATCGTCATCCTCGGNACCGTCACCCTGGATGTTGTAGGCATAG
GCTTGGTTATGCCGGTACTGCCGGGCCTCTTGCGGGATATCGTCCATTCCGACAGN
ATCGCCAGTCACTATGGNGTGCTGCTAGCGCTATATGCGTTGATGCAATTTCTATG
AGCACCCGTTCTCGGAGCACTGTCCGACCGCTTTGGCCGCCGCCCAGTCCTGCTCG
CTTCGCTACTTGGAGCCACTATCGACTACGCGATCATGGCGACCACACCCGTCCTG
TGGATCCTCTACGCCGGACGAATCGATGGCCGGAATCACCGGGGTCACAGGTGCG
GNTGCTGGNGCCTATTTCGCCGACATCAACGATGGGGAAAGATCNGGCTCGNCAC
TNCGGGCTCATNAGNNTTTGGTTTCGGCNTGGGTATTGGTNGGAAGNCCCCANG
GCCGGGGGGATTGTTNGNGNGCCAACTTCCTTGGATTGAACAATNCCCTNGGGGG
GGGGGGGTTCANCNGGCNCAACCTATTNNTGGGATTNTTNCNNATNNAGAGTCGA
TAAGGAGGNGNNGGCCANTCCNTGNAGCCCACCC

Figure 7B

CAGTATGACCATNNNCTAGCTTCTCGNCGAGACGTTTGGTNGCNGGACCAGTTAC
GAAGGCTTGAGCNAGGGAGTTGAAGATTCCNTATACTNAATGNGATAGGNCTATC
ATCGGNGGGCTCCANAGATAGCGGNCANCGNCNACANATGACCCAGAGCTNTGC
CGGCANCAGTCCTACGAGTNGNATGATNAAGTAGANAGGCATAATTGGGGNGACG
ATAGTCATGNCCCGCGGCCACCGGAAGGAGCTTAATGGGTTGNNGGCTCTCAAGG
GCATCGGTCGACGCTCTCCCTTATGTGACTCNTGNATTAGGAATCAGCCCAGTTNG
CTAGGTTTGNGGCCGNTTGNAANCAACCCCCGNCCNNANAGGGAATTGNTGNAAT
NNAAAGGGNGTTTGGGNGNCCCAACAAGTCCCCCCGNGCNANNGGGGGCCCTC
CCACCAATTNCCCCACGGCCGAAAAAAAANGTTTTCAATNAAGCCCCNAGGTNGG
GGAACCCCTNTTCTTCCCCCATCGGNGGANATTTGGNTGAATTTTTGGGGNCCAAN
ANNCCCNNCTTTNGGGTCCGNTNTTATNTCCCNCCCACAATTNNTTCCCGTTTNGG
GGNNNNNTCCNAANGAAGGTTTTNTTTCCCCCCCNATTTCCNCTTTATNCNNTTTN
TNNTTTNNNNATAGAAAAANAAAANTTTGGGGGNGCCAAGGTTTNATAATATTT

```
AAGCTTGCATGCAAATTCTATTTCAAGGAGACAGTCATAATGAAATACCTATTGCCTACGGC
AGCCGCTGGATTGTTATTACTCGCGGCCCAACCGGCCATGGCATGAGCGGCCGCCCGGGCGG
CGCGCCCTGCAGGCTAGCACTAGTGGTACCGTCGACAAGAAAGTTGAGCCCAAATCTTCAAC
TAAGACGCACACATCAGGAGGTTAGGGTGGCGGTGGCTCTCCATTCGTTTGTGAATATCAAG
GCCAATCGTCTGACCTGCCTCAACCTCCTGTCAATGCTGGCGGCGGCTCTGGTGGTGGTTCT
GGTGGCGGCTCTGAGGGTGGTGGCTCTGAGGGTGGCGGTTCTGAGGGTGGCGGCTCTGAGGG
AGGCGGTTCCGGTGGTGGCTCTGGTTCCGGTGATTTTGATTATGAAAAGATGGCAAACGCTA
ATAAGGGGGCTATGACCGAAAATGCCGATGAAAACGCGCTACAGTCTGACGCTAAAGGCAAA
CTTGATTCTGTCGCTACTGATTACGGTGCTGCTATCGATGGTTTCATTGGTGACGTTTCCGG
CCTTGCTAATGGTAATGGTGCTACTGGTGATTTGCTGGCTCTAATTCCCAAATGGCTCAAG
TCGGTGACGGTGATAATTCACCTTTAATGAATAATTTCCGTCAATATTTACCTTCCCTCCCT
CAATCGGTTGAATGTCGCCCTTTTGTCTTTAGCGCTGGTAAACCATATGAATTTTCTATTGA
TTGTGACAAAATAAACTTATTCCGTGGTGTCTTTGCGTTTCTTTTATATGTTGCCACCTTTA
TGTATGTATTTTCTACGTTTGCTAACATACTGCGTAATAAGGAGTCTTAATAAGGGAGCTTG
CATGCAAATTCTATTTCAAGGAGACAGTCATAATGAAATACCTATTGCCTACGGCAGCCGCT
GGATTGTTATTACTGAATTCACTGGCCGTCGTTTTACAACGTCGTGACTGGGAAAACCCTGG
CGTTACCCAACTTAATCGCCTTGCAGCACATCCCCCTTTCGCCAGCTGGCGTAATAGCGAAG
AGGCCCGCACCGATCGCCCTTCCCAACAGTTGCGCAGCCTGAATGGCGAATGGCGCCTGATG
CGGTATTTTCTCCTTACGCATCTGTGCGGTATTTCACACCGCATACGTCAAAGCAACCATAG
TACGCGCCCTGTAGCGGCGCATTAAGCGCGGCGGGTGTGGTGGTTACGCGCAGCGTGACCGC
TACACTTGCCAGCGCCCTAGCGCCCGCTCCTTTCGCTTTCTTCCCTTCCTTTCTCGCCACGT
TCGCCGGCTTTCCCCGTCAAGCTCTAAATCGGGGGCTCCCTTTAGGGTTCCGATTTAGTGCT
TTACGGCACCTCGACCCCAAAAAACTTGATTTGGGTGATGGTTCACGTAGTGGGCCATCGCC
CTGATAGACGGTTTTTCGCCCTTTGACGTTGGAGTCCACGTTCTTTAATAGTGGACTCTTGT
TCCAAACTGGAACAACACTCAACCCTATCTCGGGCTATTCTTTTGATTTATAAGGGATTTTG
CCGATTTCGGCCTATTGGTTAAAAAATGAGCTGATTTAACAAAAATTTAACGCGAATTTTAA
CAAAATATTAACGTTTACAATTTTATGGTGCACTCTCAGTACAATCTGCTCTGATGCCGCAT
AGTTAAGCCAGCCCCGACACCCGCCAACACCCGCTGACGCGCCCTGACGGGCTTGTCTGCTC
CCGGCATCCGCTTACAGACAAGCTGTGACCGTCTCCGGGAGCTGCATGTGTCAGAGGTTTTC
ACCGTCATCACCGAAACGCGCGAGACGAAAGGGCCTCGTGATACGCCTATTTTTATAGGTTA
ATGTCATGATAATAATGGTTTCTTAGACGTCAGGTGGCACTTTTCGGGGAAATGTGCGCGGA
ACCCCTATTTGTTTATTTTTCTAAATACATTCAAATATGTATCCGCTCATGAGACAATAACC
CTGATAAATGCTTCAATAATATTGAAAAGGAAGAGTATGAGTATTCAACATTTCCGTGTCG
CCCTTATTCCTTTTTTGCGGCATTTTGCCTTCCTGTTTTTGCTCACCCAGAAACGCTGGTGA
AAGTAAAAGATGCTGAAGATCAGTTGGGTGCACGAGTGGGTTACATCGAACTGGATCTCAAC
AGCGGTAAGATCCTTGAGAGTTTTCGCCCCGAAGAACGTTTTCCAATGATGAGCACTTTTAA
AGTTCTGCTATGTGGCGCGGTATTATCCCGTATTGACGCCGGGCAAGAGCAACTCGGTCGCC
GCATACACTATTCTCAGAATGACTTGGTTGAGTACTCACCAGTCACAGAAAAGCATCTTACG
GATGGCATGACAGTAAGAGAATTATGCAGTGCTGCCATAACCATGAGTGATAACACTGCGGC
CAACTTACTTCTGACAACGATCGGAGGACCGAAGGAGCTAACCGCTTTTTGCACAACATGG
GGGATCATGTAACTCGCCTTGATCGTTGGGAACCGGAGCTGAATGAAGCCATACCAAACGAC
GAGCGTGACACCACGATGCCTGTAGCAATGGCAACAACGTTGCGCAAACTATTAACTGGCGA
ACTACTTACTCTAGCTTCCCGGCAACAATTAATAGACTGGATGGAGGCGGATAAAGTTGCAG
GACCACTTCTGCGCTCGGCCCTTCCGGCTGGCTGGTTTATTGCTGATAAATCTGGAGCCGGT
```

Figure 8 (Part 1)

```
GAGCGTGGGTCTCGCGGTATCATTGCAGCACTGGGGCCAGATGGTAAGCCCTCCCGTATCGT
AGTTATCTACACGACGGGGAGTCAGGCAACTATGGATGAACGAAATAGACAGATCGCTGAGA
TAGGTGCCTCACTGATTAAGCATTGGTAACTGTCAGACCAAGTTTACTCATATATACTTTAG
ATTGATTTAAAACTTCATTTTTAATTTAAAAGGATCTAGGTGAAGATCCTTTTTGATAATCT
CATGACCAAAATCCCTTAACGTGAGTTTTCGTTCCACTGAGCGTCAGACCCCGTAGAAAAGA
TCAAAGGATCTTCTTGAGATCCTTTTTTTCTGCGCGTAATCTGCTGCTTGCAAACAAAAAAA
CCACCGCTACCAGCGGTGGTTTGTTTGCCGGATCAAGAGCTACCAACTCTTTTTCCGAAGGT
AACTGGCTTCAGCAGAGCGCAGATACCAAATACTGTCCTTCTAGTGTAGCCGTAGTTAGGCC
ACCACTTCAAGAACTCTGTAGCACCGCCTACATACCTCGCTCTGCTAATCCTGTTACCAGTG
GCTGCTGCCAGTGGCGATAAGTCGTGTCTTACCGGGTTGGACTCAAGACGATAGTTACCGGA
TAAGGCGCAGCGGTCGGGCTGAACGGGGGGTTCGTGCACACAGCCCAGCTTGGAGCGAACGA
CCTACACCGAACTGAGATACCTACAGCGTGAGCTATGAGAAAGCGCCACGCTTCCCGAAGGG
AGAAAGGCGGACAGGTATCCGGTAAGCGGCAGGGTCGGAACAGGAGAGCGCACGAGGGAGCT
TCCAGGGGGAAACGCCTGGTATCTTTATAGTCCTGTCGGGTTTCGCCACCTCTGACTTGAGC
GTCGATTTTTGTGATGCTCGTCAGGGGGCGGAGCCTATGGAAAAACGCCAGCAACGCGGCC
TTTTTACGGTTCCTGGCCTTTTGCTGGCCTTTTGCTCACATGTTCTTTCCTGCGTTATCCCC
TGATTCTGTGGATAACCGTATTACCGCCTTTGAGTGAGCTGATACCGCTCGCCGCAGCCGAA
CGACCGAGCGCAGCGAGTCAGTGAGCGAGGAAGCGGAAGAGCGCCCAATACGCAAACCGCCT
CTCCCCGCGCGTTGGCCGATTCATTAATGCAGCTGGCACGACAGGTTTCCCGACTGGAAAGC
GGGCAGTGAGCGCAACGCAATTAATGTGAGTTAGCTCACTCATTAGGCACCCCAGGCTTTAC
ACTTTATGCTTCCGGCTCGTATGTTGTGTGGAATTGTGAGCGGATAACAATTTCACACAGGA
AACAGCTATGACCATGATTACGCC
```

Figure 8 (Part 2)

Figure 14A

Nucleic acid sequence of GFP mutant #53 (SEQ ID NO: 14)

atgagtaaaggagaagaacttttcactggagttgtcccaattcttgttgaattagatggt
gatgttaatgggcacaaattttctgtcagtggagagggtgaaggtgatgcaacatacgga
aaacttacccttaaatttatttgcactactggaaaactacctgttccatggccaacactt
gtcactactctctcttatggtgttcaatgcttttcaagatacccagatcatatgaaacgg
catgactttttcaagagtgccatgcccgaaggttatgtacaggaaagaactatattttc
aaagatgacgggaactacaagacacgtgctgaagtcaagtttgaaggtgataccttgtt
aatagaatcgagttaaaaggtattgattttaaagaagatggaaacattcttggacacaaa
ttggaatacaactataactcacacaatgtatacatcatggcagacaaacaaaagaatgga
atcaaagttaacttcaaaattagacacaacgttgaagatggaagcgttcaactagcagac
cattatcaactaaatactccaattggcgatggccctgtccttttaccagacaaccattac
ctgtccacacaatctgcccttcgaaagatcccaacgaaaagagagaccacatggtcctt
cttgagtttgtaacagctgctgggattacacatggcatggatgaactatacaaa

Figure 14B

Amino acid sequence of GFP mutant #53 (SEQ ID NO: 15)

MSKGEELFTGVVPILVELDGDVNGHKFSVSGEGEGDATYGKLTLKFI
CTTGKLPVPWPTLVTTLSYGVQCFSRYPDHMKRHDFFKSAMPEGYV
QERTIFFKDDGNYKTRAEVKFEGDTLVNRIELKGIDFKEDGNILGHKL
EYNYNSHNVYIMADKQKNGIKVNFKIRHNVEDGSVQLADHYQLNTP
IGDGPVLLPDNHYLSTQSALSKDPNEKRDHMVLLEFVTAAGITHGMD
ELYK

SEQUENCE LISTING

<160> NUMBER OF SEQ ID NOS: 15

<210> SEQ ID NO 1
<211> LENGTH: 37
<212> TYPE: DNA
<213> ORGANISM: Artificial Sequence
<220> FEATURE:
<223> OTHER INFORMATION: Primer

<400> SEQUENCE: 1
cagcttatca tcgataagct ttaatgcggt agtttat                              37

<210> SEQ ID NO 2
<211> LENGTH: 38
<212> TYPE: DNA
<213> ORGANISM: Artificial Sequence
<220> FEATURE:
<223> OTHER INFORMATION: Primer

<400> SEQUENCE: 2
cgtagcccag cgcgtcggcc gccatgccgg cgataatg                             38

<210> SEQ ID NO 3
<211> LENGTH: 59
<212> TYPE: DNA
<213> ORGANISM: Artificial Sequence
<220> FEATURE:
<223> OTHER INFORMATION: Primer

<400> SEQUENCE: 3
cactatggcg tgctgctagc gctatatgcg ttgatgcaat ttctatgagc acccgttct      59

<210> SEQ ID NO 4
<211> LENGTH: 65
<212> TYPE: DNA
<213> ORGANISM: Artificial Sequence
<220> FEATURE:
<223> OTHER INFORMATION: Primer

<400> SEQUENCE: 4
tctcaagggc atcggtcgac gctctccctt atgcgactcc tgcattagga atcagcccag     60
tagta                                                                65

<210> SEQ ID NO 5
<211> LENGTH: 710
<212> TYPE: DNA
<213> ORGANISM: Artificial Sequence
<220> FEATURE:
<223> OTHER INFORMATION: Theoretical Insert

<400> SEQUENCE: 5
ctagcgctat atgcgttgat gcaatttcta tgagcacccg ttctcggagc actgtccgac     60
cgctttggcc gccgcccagt cctgctcgct tcgctacttg gagccactat cgactacgcg    120
atcatggcga ccacacccgt cctgtggatc ctctacgccg gacgcatcgt ggccggcatc    180
accggcgcca caggtgcggt tgctggcgcc tatatcgccg acatcaccga tggggaagat    240
cgggctcgcc acttcgggct catgagcgct tgtttcggcg tgggtatggt ggcaggcccc    300
gtggccgggg gactgttggg cgccatctcc ttgcatgcac cattccttgc ggcggcggtg    360
ctcaacggcc tcaacctact actgggctgc ttcctaatgc aggagtcgca taagggagag    420
cgtcgaccga tgcccttgag agccttcaac ccagtcagct ccttccggtg ggcgcgggc     480

```
atgactatcg tcgccgcact tatgactgtc ttctttatca tgcaactcgt aggacaggtg    540
ccggcagcgc tctgggtcat tttcggcgag daccgctttc gctggagcgc gacgatgatc    600
ggcctgtcgc ttgcggtatt cggaatcttg cacgccctcg ctcaagcctt cgtcactggt    660
cccgccacca aacgtttcgg cgagaagcag gccattatcg ccggcatggc                710

<210> SEQ ID NO 6
<211> LENGTH: 322
<212> TYPE: DNA
<213> ORGANISM: Artificial Sequence
<220> FEATURE:
<223> OTHER INFORMATION: Theoretical Insert

<400> SEQUENCE: 6
gagccactat cgactacgcg atcatggcga ccacacccgt cctgtggatc ctctacgccg     60
gacgcatcgt ggccggcatc accggcgcca caggtgcggt tgctggcgcc tatatcgccg    120
acatcaccga tggggaagat cgggctcgcc acttcgggct catgagcgct tgtttcggcg    180
tgggtatggt ggcaggcccc gtggccgggg gactgttggg cgccatctcc ttgcatgcac    240
cattccttgc ggcggcggtg ctcaacggcc tcaacctact actgggctga ttcctaatgc    300
aggagtcgca taagggagag cg                                             322

<210> SEQ ID NO 7
<211> LENGTH: 645
<212> TYPE: DNA
<213> ORGANISM: Artificial Sequence
<220> FEATURE:
<223> OTHER INFORMATION: Experimentally determined Sequence
<220> FEATURE:
<221> NAME/KEY: misc_feature
<222> LOCATION: (0)...(0)
<223> OTHER INFORMATION: n = a, t, g, or c

<400> SEQUENCE: 7
ccgttnaagn nnacacagtt anattgttaa ngcagtcagg caccgtgtat gaaatctaac     60
aatgcgctca tcgtcatcct cggnaccgtc accctggatg ttgtaggcat aggcttggtt    120
atgccggtac tgccgggcct cttgcgggat atcgtccatt ccgacagnat cgccagtcac    180 tatgngtgc tgctagcgct atatgcgttg atgcaatttc tatgagcacc cgttctcgga     240
gcactgtccg accgctttgg ccgccgccca gtcctgctcg cttcgctact tggagccact    300
atcgactacg cgatcatggc gaccacaccc gtcctgtgga tcctctacgc cggacgaatc    360
gatggccgga atcaccgggg tcacaggtgc ggntgctggn gcctatttcg ccgacatcaa    420
cgatggggaa agatcnggct cgncactncg ggctcatnag nntttggttt cggcntgggt    480
attggtngga agnccccan ggccgggggg attgttngng ngccaacttc cttggattga    540 acaatncct nggggggggg gggttcancn ggcncaacct attnntggga ttntncnna    600 tnnagagtcg ataaggaggn gnnggccant ccntgnagcc caccc                    645

<210> SEQ ID NO 8
<211> LENGTH: 716
<212> TYPE: DNA
<213> ORGANISM: Artificial Sequence
<220> FEATURE:
<223> OTHER INFORMATION: Experimentally Determined Sequence
<220> FEATURE:
<221> NAME/KEY: misc_feature
<222> LOCATION: (0)...(0)
<223> OTHER INFORMATION: n = a, t, g, or c
```

<400> SEQUENCE: 8

```
cagtatgacc atnnnctagc ttctcgncga gacgtttggt ngcnggacca gttacgaagg      60
cttgagcnag ggagttgaag attccntata ctnaatgnga taggnctatc atcggngggc     120
tccanagata gcggncancg ncnacanatg acccagagct ntgccggcan cagtcctacg     180
agtngnatga tnaagtagan aggcataatt ggggngacga tagtcatgnc ccgcggccac     240
cggaaggagc ttaatgggtt gnnggctctc aagggcatcg gtcgacgctc tcccttatgt     300
gactcntgna ttaggaatca gcccagttng ctaggtttgn ggccgnttgn aancaacccc     360
cgnccnnana gggaattgnt gnaatnnaaa gggngtttgg gngncccaac aagtcccccc     420
cgngcnanng ggggccctcc caccaattnc cccacggccg aaaaaaaang ttttcaatna     480
agccccnagg tngggaacc cctnttcttc ccccatcggn gganatttgg ntgaattttt      540
ggggnccaan annccnnct ttngggtccg ntnttatntc ccnccacaa ttnnttcccg       600
tttnggggnn nnntccnaan gaaggttttn tttcccccc natttccnct ttatncnntt      660
tntnnttnn nnatagaaaa anaaaanttt ggggngcca aggtttnata atattt           716
```

<210> SEQ ID NO 9
<211> LENGTH: 4054
<212> TYPE: DNA
<213> ORGANISM: Artificial Sequence
<220> FEATURE:
<223> OTHER INFORMATION: pEXmide V

<400> SEQUENCE: 9

```
aagcttgcat gcaaattcta tttcaaggag acagtcataa tgaaatacct attgcctacg      60
gcagccgctg gattgttatt actcgcggcc caaccggcca tggcatgagc ggccgcccgg     120
gcggcgcgcc ctgcaggcta gcactagtgg taccgtcgac aagaaagttg agcccaaatc     180
ttcaactaag acgcacacat caggaggtta gggtggcggt ggctctccat cgtttgtga     240
atatcaaggc caatcgtctg acctgcctca acctcctgtc aatgctggcg gcggctctgg     300
tggtggttct ggtggcggct ctgagggtgg tggctctgag ggtggcggtt ctgagggtgg     360
cggctctgag ggaggcggtt ccggtggtgg ctctggttcc ggtgattttg attatgaaaa     420
gatggcaaac gctaataagg gggctatgac cgaaaatgcc gatgaaaacg cgctacagtc     480
tgacgctaaa ggcaaacttg attctgtcgc tactgattac ggtgctgcta tcgatggttt     540
cattggtgac gtttccggcc ttgctaatgg taatggtgct actggtgatt tgctggctc      600
taattcccaa atggctcaag tcggtgacgg tgataattca cctttaatga ataatttccg     660
tcaatattta ccttccctcc ctcaatcggt tgaatgtcgc ccttttgtct ttagcgctgg     720
taaaccatat gaattttcta ttgattgtga caaaataaac ttattccgtg gtgtctttgc     780
gtttcttta tatgttgcca cctttatgta tgtattttct acgtttgcta acatactgcg     840
taataaggag tcttaataag ggagcttgca tgcaaattct atttcaagga cagtcata      900
atgaaatacc tattgcctac ggcagccgct ggattgttat tactgaattc actggccgtc     960
gttttacaac gtcgtgactg ggaaaaccct ggcgttaccc aacttaatcg ccttgcagca    1020
catccccctt tcgccagctg gcgtaatagc gaagaggccc gcaccgatcg cccttcccaa    1080
cagttgcgca gcctgaatgg cgaatggcgc tgatgcggt attttctcct tacgcatctg     1140
tgcggtattt cacaccgcat acgtcaaagc aaccatagta cgcgccctgt agcggcgcat    1200
taagcgcggc gggtgtggtg gttacgcgca gcgtgaccgc tacacttgcc agcgccctag    1260
cgcccgctcc tttcgctttc ttcccttcct ttctcgccac gttcgccggc tttccccgtc    1320
```

-continued

```
aagctctaaa tcgggggctc cctttagggt tccgatttag tgctttacgg cacctcgacc    1380
ccaaaaaact tgatttgggt gatggttcac gtagtgggcc atcgccctga tagacggttt    1440
ttcgcccttt gacgttggag tccacgttct ttaatagtgg actcttgttc caaactggaa    1500
caacactcaa ccctatctcg ggctattctt tgatttata agggattttg ccgatttcgg     1560
cctattggtt aaaaaatgag ctgatttaac aaaaatttaa cgcgaatttt aacaaaatat    1620
taacgtttac aattttatgg tgcactctca gtacaatctg ctctgatgcc gcatagttaa    1680
gccagccccg acaccgcca acaccgctg acgcgccctg acgggcttgt ctgctcccgg      1740
catccgctta cagacaagct gtgaccgtct ccgggagctg catgtgtcag aggttttcac    1800
cgtcatcacc gaaacgcgcg agacgaaagg gcctcgtgat acgcctattt ttataggtta    1860
atgtcatgat aataatggtt tcttagacgt caggtggcac ttttcgggga aatgtgcgcg    1920
gaacccctat ttgtttattt ttctaaatac attcaaatat gtatccgctc atgagacaat    1980
aaccctgata aatgcttcaa taatattgaa aaggaagag tatgagtatt caacatttcc     2040
gtgtcgccct tattccttt ttgcggcatt ttgccttcct gttttgctc acccagaaac      2100
gctggtgaaa gtaaagatg ctgaagatca gttgggtgca cgagtgggtt acatcgaact     2160
ggatctcaac agcggtaaga tccttgagag ttttcgcccc gaagaacgtt ttccaatgat    2220
gagcactttt aaagttctgc tatgtggcgc ggtattatcc cgtattgacg ccgggcaaga    2280
gcaactcggt cgccgcatac actattctca gaatgacttg gttgagtact caccagtcac    2340
agaaaagcat cttacggatg gcatgacagt aagagaatta tgcagtgctg ccataaccat    2400
gagtgataac actgcggcca acttacttct gacaacgatc ggaggaccga aggagctaac    2460
cgcttttttg cacaacatgg gggatcatgt aactcgcctt gatcgttggg aaccggagct    2520
gaatgaagcc ataccaaacg acgagcgtga ccacgatg cctgtagcaa tggcaacaac      2580
gttgcgcaaa ctattaactg gcgaactact tactctagct tcccggcaac aattaataga    2640
ctggatggag gcggataaag ttgcaggacc acttctgcgc tcggcccttc cggctggctg    2700
gtttattgct gataaatctg gagccggtga gcgtgggtct cgcggtatca ttgcagcact    2760
ggggccagat ggtaagccct cccgtatcgt agttatctac acgacgggga gtcaggcaac    2820
tatgatgaa cgaaatagac agatcgctga gataggtgcc tcactgatta gcattggta     2880
actgtcagac caagtttact catatatact ttagattgat ttaaaacttc attttaatt     2940
taaaaggatc taggtgaaga tccttttga taatctcatg accaaaatcc cttaacgtga    3000
gttttcgttc cactgagcgt cagaccccgt agaaaagatc aaaggatctt cttgagatcc    3060
tttttttctg cgcgtaatct gctgcttgca acaaaaaaa ccaccgctac cagcggtggt     3120
ttgtttgccg gatcaagagc taccaactct ttttccgaag gtaactggct tcagcagagc    3180
gcagatacca aatactgtcc ttctagtgta gccgtagtta ggccaccact tcaagaactc    3240
tgtagcaccg cctacatacc tcgctctgct aatcctgtta ccagtggctg ctgccagtgg    3300
cgataagtcg tgtcttaccg ggttggactc aagacgatag ttaccggata aggcgcagcg    3360
gtcgggctga acggggggtt cgtgcacaca gcccagcttg gagcgaacga cctacaccga    3420
actgagatac ctacagcgtg agctatgaga aagcgccacg cttcccgaag ggagaaaggc    3480
ggacaggtat ccggtaagcg gcagggtcgg aacaggagag cgcacgaggg agcttccagg    3540
gggaaacgcc tggtatcttt atagtcctgt cgggtttcgc cacctctgac ttgagcgtcg    3600
attttgtga tgctcgtcag ggggcggag cctatggaaa aacgccagca acgcggcctt      3660
```

```
tttacggttc ctggccttttt gctggccttt tgctcacatg ttctttcctg cgttatcccc      3720
tgattctgtg gataaccgta ttaccgcctt tgagtgagct gataccgctc gccgcagccg      3780
aacgaccgag cgcagcgagt cagtgagcga ggaagcggaa gagcgcccaa tacgcaaacc      3840
gcctctcccc gcgcgttggc cgattcatta atgcagctgg cacgacaggt ttcccgactg      3900
gaaagcgggc agtgagcgca acgcaattaa tgtgagttag ctcactcatt aggcacccca      3960
ggctttacac tttatgcttc cggctcgtat gttgtgtgga attgtgagcg gataacaatt      4020
tcacacagga aacagctatg accatgatta cgcc                                  4054

<210> SEQ ID NO 10
<211> LENGTH: 61
<212> TYPE: DNA
<213> ORGANISM: Artificial Sequence
<220> FEATURE:
<223> OTHER INFORMATION: Primer

<400> SEQUENCE: 10
caactttctt gtcgacttta tcatcatcat ctttataatc acctaggacc gtcagcttgg      60
t                                                                      61

<210> SEQ ID NO 11
<211> LENGTH: 43
<212> TYPE: DNA
<213> ORGANISM: Artificial Sequence
<220> FEATURE:
<223> OTHER INFORMATION: Primer

<400> SEQUENCE: 11
actcgcggcc caaccggcca tggccgaggt gcagctgttg gac                         43

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
ggagagccac cgccacccta ac                                               22

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
tcacacagga aacagctatg ac                                               22

<210> SEQ ID NO 14
<211> LENGTH: 714
<212> TYPE: DNA
<213> ORGANISM: Artificial Sequence
<220> FEATURE:
<223> OTHER INFORMATION: Synthetic Sequence

<400> SEQUENCE: 14
atgagtaaag gagaagaact tttcactgga gttgtcccaa ttcttgttga attagatggt      60
gatgttaatg ggcacaaatt ttctgtcagt ggagagggtg aaggtgatgc aacatacgga     120
aaacttaccc ttaaatttat ttgcactact ggaaaactac ctgttccatg gccaacactt     180
```

-continued

```
gtcactactc tctcttatgg tgttcaatgc ttttcaagat acccagatca tatgaaacgg      240
catgactttt tcaagagtgc catgcccgaa ggttatgtac aggaaagaac tatattttc       300 aaagatgacg ggaactacaa gacacgtgct gaagtcaagt ttgaaggtga taccttgtt       360 aatagaatcg agttaaaagg tattgatttt aaagaagatg gaaacattct tggacacaaa     420
ttggaataca actataactc acacaatgta tacatcatgg cagacaaaca aaagaatgga     480
atcaaagtta acttcaaaat tagacacaac gttgaagatg gaagcgttca actagcagac     540
cattatcaac taaatactcc aattggcgat ggccctgtcc ttttaccaga caaccattac     600
ctgtccacac aatctgccct ttcgaaagat cccaacgaaa agagagacca catggtcctt     660
cttgagtttg taacagctgc tgggattaca catggcatgg atgaactata caaa           714
```

<210> SEQ ID NO 15
<211> LENGTH: 238
<212> TYPE: PRT
<213> ORGANISM: Artificial Sequence
<220> FEATURE:
<223> OTHER INFORMATION: Synthetic Sequence

<400> SEQUENCE: 15

```
Met Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
             20                  25                  30

Gly Glu Gly Asp Ala Thr Tyr Gly Lys Leu Thr Leu Lys Phe Ile Cys
         35                  40                  45

Thr Thr Gly Lys Leu Pro Val Pro Trp Pro Thr Leu Val Thr Thr Leu
     50                  55                  60

Ser Tyr Gly Val Gln Cys Phe Ser Arg Tyr Pro Asp His Met Lys Arg
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Val Glu Asp Gly Ser Val
                165                 170                 175

Gln Leu Ala Asp His Tyr Gln Leu Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

METHOD FOR IN VITRO MOLECULAR EVOLUTION OF PROTEIN FUNCTION INVOLVING THE USE OF EXONUCLEASE ENZYME AND TWO POPULATIONS OF PARENT POLYNUCLEOTIDE SEQUENCE

This application is a continuation-in part application of U.S. application Ser. No. 09/445,649, filed—Apr. 6, 2000, U.S. Pat. No. 6,495,321, which in turn claims priority to international patent application PCT/GB98/01757 filed Jun. 16, 1998. Each of the foregoing applications is incorporated in their entirety by reference herein.

FIELD OF THE INVENTION

The present invention relates to a method for in vitro molecular evolution of protein function.

BACKGROUND OF THE INVENTION

Protein function can be modified and improved in vitro by a variety of methods, including site directed mutagenesis (Alber et al, Nature, 5; 330(6143):41–46, 1987) combinatorial cloning (Huse et al, Science, 246:1275–1281, 1989; Marks et al, Biotechnology, 10: 779–783, 1992) and random mutagenesis combined with appropriate selection systems (Barbas et al, PNAS. USA, 89: 4457–4461, 1992).

The method of random mutagenesis together with selection has been used in a number of cases to improve protein function and two different strategies exist. Firstly, randomization of the entire gene sequence in combination with the selection of a variant (mutant) protein with the desired characteristics, followed by a new round of random mutagenesis and selection. This method can then be repeated until a protein variant is found which is considered optimal (Schier, R. et al., J. Mol. Biol., 263(4): 551–567 (1996). Here, the traditional route to introduce mutations is by error prone PCR (Leung et al, Technique, 1: 11–15, 1989) with a mutation rate of ≅0.7%. Secondly, defined regions of the gene can be mutagenized with degenerate primers, which allows for mutation rates up to 100% (Griffiths et al, EMBO. J, 13: 3245–3260, 1994; Yang et al, J. Mol. Biol. 254: 392–403, 1995). The higher the mutation rate used, the more limited the region of the gene that can be subjected to mutations.

Random mutation has been used extensively in the field of antibody engineering. In vivo formed antibody genes can be cloned in vitro (Larrick et al, Biochem. Biophys. Res. Commun. 160: 1250–1256, 1989) and random combinations of the genes encoding the variable heavy and light genes can be subjected to selection (Marks et al, Biotechnology, 10: 779–783, 1992). Functional antibody fragments selected can be further improved using random mutagenesis and additional rounds of selection (Schier, R. et al., J. Mol. Biol. 263(4): 551–567 (1996).

The strategy of random mutagenesis is also followed by selection. Variants with interesting characteristics can be selected and the mutated DNA regions from different variants, each with interesting characteristics, are combined into one coding sequence (Yang et al, J. Mol. Biol. 254: 392–403, 1995). This is a multi-step sequential process, and potential synergistic effects of different mutations in different regions can be lost, since they are not subjected to selection in combination. Thus, these two strategies do not include simultaneous mutagenesis of defined regions and selection of a combination of these regions. Another process involves combinatorial pairing of genes which can be used to improve, for example, antibody affinity (Marks et al, Biotechnology, 10: 779–783, 1992). Here, the three CDR-regions in each variable gene are fixed and this technology does not allow for shuffling of individual gene segments in the gene for the variable domain, for example, including the CDR regions, between clones.

The process of DNA shuffling (Stemmer, Nature 370: 389–391, 1994) utilizes random fragmentation of DNA and assembly of fragments into a functional coding sequence. In this process it is possible to introduce chemically synthesized DNA sequences and thus target changes in nucleic acid sequence to defined regions for which DNA sequence is known (Crameri et al, Biotechniques, 18: 194–196, 1995). In theory, it is also possible to shuffle DNA between any clones. However, if the resulting shuffled gene is to be functional with respect to expression and activity, the clones to be shuffled have to be related or even identical with the exception of a low level of random mutations. DNA shuffling between genetically different clones will generally produce non-functional genes.

Selection of functional proteins from molecular libraries has been revolutionized by the development of the phage display technology (Parmley et al, Gene, 73: 305–391 1988; McCafferty et al, Nature, 348: 552–554, 1990; Barbas et al, PNAS. USA, 88: 7978–7982, 1991). Here, the phenotype (protein) is directly linked to its corresponding genotype (DNA) and this allows for directly cloning of the genetic material which can then be subjected to further modifications in order to improve protein function. Phage display has been used to clone functional binders from a variety of molecular libraries with up to $10^{11}$ transformants in size (Griffiths et al, EMBO. J. 13: 3245–3260, 1994). Thus, phage display can be used to directly clone functional binders from molecular libraries, and can also be used to improve further the clones originally selected.

SUMMARY OF THE INVENTION

According to one aspect of the present invention, there is provided a method for generating a polynucleotide sequence or population of sequences from at least one parent polynucleotide sequence encoding one or more protein motifs, comprising the steps of a) digesting at least one parent polynucleotide sequence with at least one exonuclease to generate at least one population of fragments, wherein said digesting with said at least one exonuclease comprises digesting a first parent polynucleotide sequence with a first exonuclease to produce a first population of fragments and digesting a second parent polynucleotide sequence with a second exonuclease to produce a second population of fragments;

b) incubating the first and second population of fragments under conditions wherein said fragments of said first and second population anneal;

c) amplifying the annealed fragments of step b) to generate at least one polynucleotide sequence encoding one or more protein motifs having altered characteristics as compared to the one or more protein motifs encoded by said parent polynucleotide.

Preferably the method further comprises the step of expressing the resulting protein encoded by the assembled polynucleotide sequence and screening the protein for desired characteristics.

In one aspect of the invention, at least one parent polynucleotide sequence is double-stranded and the method further comprises the step of separately generating single-stranded plus and minus strand polynucleotide sequence from said double-stranded fragments prior to step a). In a particular aspect, the single-stranded plus and minus strand polynucleotide sequences are separated prior to the digestion step in b).

In a preferred aspect of the invention, at least one parent polynucleotide sequence is single-stranded. Further, the at least one single-stranded parent polynucleotide may comprise at least one single-stranded plus polynucleotide sequence and at least one single-stranded minus polynucleotide sequence.

In a particularly preferred aspect, the single-stranded plus polynucleotide sequence is digested with a first exonuclease to produce a first population of single-stranded plus fragments and the single-stranded minus polynucleotide sequence is digested with a second exonuclease to produce a second population of single-stranded minus fragments.

In one aspect, the first and second exonuclease are the same. In a preferred aspect, the first and the second exonucleases are different.

In order to generate a polynucleotide sequence of desired characteristics the at least one parent polynucleotide sequence encoding one or more protein motifs may be subjected to mutagenesis to create a plurality of differently mutated derivatives thereof. Likewise, a parent polynucleotide may be obtained already encoding a plurality of variant protein motifs of unknown sequence.

Random mutagenesis can be accomplished by any conventional method as described above, but a suitable method is error-prone PCR.

Any exonuclease that digests polynucleotide from the 3' prime end to the 5' prime end or from both the 3' and the 5' end may be used. In one aspect of the invention, digesting the at least one parent polynucleotide sequence is performed with an exonuclease selected from the group consisting BAL31, Exonuclease I, Exonuclease III, Exonuclease V, Exonuclease VII, T7 gene 6, and RecJ exonuclease.

BAL31, for example, is an exonuclease that digests and removes nucleotide bases from both the 3' and the 5' ends of a linear polynucleotide molecule. The enzyme uses Ca2+ as a co-factor which can be bound in complex with EGTA (Ethylene Glycol bis β-amino ethyl Ether) N,N,N',N'-tetra acetic acid). EGTA does not bind Mg2+ which is necessary for the subsequent PCR process. Linear DNA sequences are digested with BAL31 and the reaction stopped at different time points by the addition of EGTA. The individual digested fragments are mixed and reassembled with PCR technology. The assembled (recombinant) gene may then be cloned into an expression vector to express an encoded recombinant protein having altered characteristics. The protein may then be analyzed for improved characteristics.

In a preferred embodiment, a first parent polynucleotide sequence is digested with a first exonuclease for a first incubation time to produce a first population of fragments and a second parent polynucleotide sequence is digested with a second exonuclease for a second incubation time to produce a second population of fragments. Also provided are methods wherein a first or a second parent polynucleotide sequence is digested separately with 1) a first exonuclease to generate a first population of fragments, 2) a second exonuclease to generate a second population of fragments, 3) a third exonuclease to generate a third population of fragments, 4) a fourth exonuclease to generate a fourth population of fragments, 5) a fifth exonuclease to generate a fifth population of fragments, 6) a sixth exonuclease to generate a sixth population of fragments, and 7) a seventh exonuclease to generate a seventh population of fragments. Such populations of fragments may then be used to advantage in subsequent annealing steps to maximize the diversity of recombinant polynucleotides generated having altered characteristics as compared to those of the parent polynucleotides.

Also provided are methods wherein the duration of the first and second incubation time, for example, can be the same or different. By controlling the duration of the exonucleolytic digestion, the size of the resultant polynucleotide fragments is determined. Further, as some exonucleases digest polynucleotide sequences from both the 3' and the 5' ends, fragments which center around the middle of the gene sequence may be selected following digestion with such exonucleases. Such centrally located fragments may be mutated randomly by error prone PCR, for example, and subsequently used in the shuffling process.

However, in some cases it may be desirable to maintain the central region of the parent polynucleotide sequence. Such an objective is achieved by choosing long fragments generated after exonuclease treatment of a short duration and/or low enzyme concentration. Conversely, if it is desirable to shuffle the middle of the parent polynucleotide sequence, short fragments generated by prolonged exonuclease treatment and/or incubation at high enzyme concentration may be used.

It is preferable to use PCR technology to assemble single-stranded polynucleotide fragments into double-stranded polynucleotide sequences.

The polynucleotide sequence is preferably DNA although RNA may be used. For simplicity, the term polynucleotide will now be used in the following text in relation to DNA (e.g., single-stranded or double-stranded) but it will be appreciated that the present invention is applicable to both RNA and DNA.

Also provided are methods further comprising digesting a third parent polynucleotide sequence with a third exonuclease to produce a third population of fragments and contacting said third population of fragments to said first and second population of fragments in step b), wherein said fragments of said first, second, and third population of fragments anneal. In short, the methods of the present invention encompass the use of two or more parent polynucleotide sequences, wherein each parent polynucleotide sequence is digested with an exonuclease to produce a population of fragments which may be used in subsequent shuffling steps to generate a recombinant polynucleotide sequence.

The method of the present invention may be carried out on any polynucleotide which encodes a particular product, for example, any protein having binding or catalytic properties (e.g., antibodies or parts of antibodies), enzymes or receptors. Further, any polynucleotide that has a function that may be altered. Catalytic RNA, for example, may be shuffled in accordance with the present invention.

The present invention further comprises the step of screening the at least one recombinant polynucleotide for desired characteristics.

It is preferable that the parent polynucleotide encoding one or more protein motifs is at least 12 nucleotides in length, more preferably at least 20 nucleotides in length, even more preferably more than 50 nucleotides in length. Polynucleotides being at least 100 nucleotides in length or even at least 200 nucleotides in length may be used. Parent polynucleotides that encode large proteins such as enzymes or antibodies may comprise hundreds or thousands of nucleotides. The present invention may be carried out on a parent polynucleotide of any size.

The present invention also provides polynucleotide sequences generated by the method described above having desired characteristics. Such recombinant polynucleotide sequences may be used in gene therapy vectors and replication-defective gene therapy constructs or vaccination vectors for DNA-based vaccinations. Further, the polynucleotide sequences may be used as research tools.

The present invention also provides a polynucleotide library of sequences generated by the method described above from which a polynucleotide may be selected which encodes a protein having the desired characteristics. It is preferable that the polynucleotide library is a cDNA library.

In a preferred aspect, the invention further comprises the step of expressing the at least one assembled recombinant polynucleotide and screening the resulting recombinant polypeptide for desired characteristics.

The present invention also provides recombinant proteins produced by the method herein, including antibodies, enzymes, and receptors having characteristics that differ from those of the wild type proteins from which they are derived. These proteins may be used individually or in combination within a pharmaceutically acceptable carrier as vaccines or medicaments for therapy. They may be used, for example, as immunogens or otherwise for generating specific antibodies. They may also be used as research tools.

The desired characteristics of a polynucleotide generated by the present invention or a protein encoded by a polynucleotide generated by the present invention may be any variation in the normal activity of the wild type (parent) polynucleotide or the polypeptide, protein or protein motifs encoded therefrom. For example, it may be desirable to reduce or increase the catalytic activity of an enzyme, or improve or reduce the binding specificity of an antibody. Further, if the protein, or polynucleotide is an immunogen, it may be desirable to reduce or increase its immunogenic properties. The parent polynucleotide preferably encodes one or more protein motifs. These are defined by regions of polynucleotide sequence that encode polypeptide sequence having or potentially having characteristic protein function. For example, a protein motif may define a portion of a whole protein, e.g., a protein domain, an epitope, a cleavage site or a catalytic site, etc.

It may be desirable to modify a protein so as to alter the conformation of certain epitopes, thereby improving its antigenicity and/or reducing cross-reactivity. For example, should such a protein be used as an antigen, the modification may reduce any cross-reaction of raised antibodies with similar proteins.

Although the term "enzyme" is used, this is to be interpreted as also including any polypeptide having enzyme-like activity, e.g., a catalytic function. For example, polypeptides being part of an enzyme may still possess catalytic function. Likewise, the term "antibody" should be construed as covering any binding substance having a binding domain with the required specificity. This includes antibody fragments, derivatives, functional equivalents and homologues of antibodies, including synthetic molecules and molecules whose shape mimics that of an antibody enabling it to bind an antigen or epitope. Examples of antibody fragments, capable of binding an antigen or other binding partner are the Fab fragment consisting of the VL, VH, Cl and CH1 domains, the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

By 'corresponding populations of single stranded polynucleotide fragments' we mean the population of fragments produced by digestion of the first and second populations of single stranded polynucleotide molecules with an exonuclease.

By 'equivalent parameter' we mean the same parameter used in the reaction for digestion of the other population of single stranded polynucleotide molecules. For example, the exonuclease used for digestion of the first population of single stranded polynucleotide molecules may differ from the exonuclease used for digestion of the second population of single stranded polynucleotide molecules.

By 'exonuclease' we mean a polypeptide, e.g. enzyme or fragment thereof, having exonucleolytic activity. Preferably, the exonucleolytic activity of the polypeptide is greater than the endonucleolytic activity of the polypeptide. More preferably, the polypeptide has exonucleolytic activity but is substantially free of endonucleolytic activity.

Advantageously, the parameter of the digestion reaction which differs is selected from exonuclease type, exonuclease concentration, reaction volume, duration of the digestion reaction, temperature of the reaction mixture, pH of the reaction mixture, length of parent single stranded polynucleotide sequences, amount of single stranded polynucleotide molecules and buffer composition of the reaction mixture.

In a preferred embodiment of the method of the first aspect of the invention, the exonuclease used for digestion of the first population of single stranded polynucleotide molecules is different from the exonuclease used for digestion of the second population of single stranded polynucleotide molecules. Preferably, the exonuclease used for digestion of the first population of single stranded polynucleotide molecules is a 3' exonuclease (i.e. preferentially or exclusively removes nucleotides from 3' terminus of ss polynucleotides) and the exonuclease used for digestion of the second population of single stranded polynucleotide molecules is a 5' exonuclease (i.e. preferentially or exclusively removes nucleotides from 5' terminus of ss polynucleotides).

In order to obtain expression of the generated recombinant polynucleotide sequence, the sequence may be incorporated into a vector having control sequences operably linked to the polynucleotide sequence to control its expression. The vectors may include other sequences such as promoters or enhancers to drive the expression of the inserted polynucleotide sequence and additional polynucleotide sequences to facilitate expression of the encoded protein as a fusion protein and/or as a secreted protein.

A protein encoded by a recombinant polynucleotide sequence can be obtained by transforming a vector as described above into host cells in which the vector is functional, culturing the host cells so that the protein is produced and recovering the protein from the host cells or the surrounding medium. Prokaryotic and eukaryotic cells may be used for this purpose in the art, including strains of E. coli and yeast, and eukaryotic cell lines such as COS cells, CHO cells, or various insect or plant cell lines. Expression systems of utility for such purposes are well known in the art. The choice of host cell can be used to control the properties of the protein expressed in those cells, e.g. controlling where the protein is deposited in the host cells or affecting properties such as its glycosylation.

The protein encoded by the polynucleotide sequence may be expressed by methods well known in the art. Conveniently, expression may be achieved by growing a host cell in culture, containing such a vector, under appropriate conditions which cause or allow expression of the protein.

Systems for cloning and expression of a protein in a variety of different host cells are well known. Suitable host cells include bacteria, eukaryotic cells such as mammalian cells and yeast, and insect baculovirus systems. Mammalian cell lines available in the art for expression of a heterologous polypeptide include Chinese hamster ovary cells, HeLa cells, baby hamster kidney cells, COS cells and many others. A common, preferred bacterial host is *E. coli*.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. λ phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of polynucleotide sequences, for example in preparation of polynucleotide constructs, mutagenesis, sequencing, introduction of DNA into cells and gene expression, and analysis of proteins, are described in detail in Current Protocols in Molecular Biology, Ausubel et al. eds., John Wiley & Sons, 1992.

The FIND system can be used for the creation of DNA libraries comprising variable sequences which can be screened for the desired protein function in a number of ways. Phage display may be used to select for binding avidity (Griffith et al., EMBO J., 113: 3245–3260 (1994) and to screen for enzyme function (Crameri, A. et al., Nature, 391(6664): 288–291 (1998); Zhang, J. H. et al., PNAS USA, 94:(9): 4504–4509 (1997); Warren, M. S. et al., Biochemistry, 35(27): 8855–8862 (1996).

A protein provided by the present invention may be used in screening for molecules which affect or modulate its activity or function. Such molecules may be useful in a therapeutic (possibly including prophylactic) context.

The present invention also provides vectors comprising polynucleotide sequences generated by the method described above.

The present invention also provides compositions comprising either polynucleotide sequences, vectors comprising the polynucleotide sequences or proteins generated by the method described above and a pharmaceutically acceptable carrier or a carrier suitable for research purposes.

The present invention also provides a method comprising, following the identification of the polynucleotide or polypeptide having desired characteristics by the method described above, the manufacture of that polypeptide or polynucleotide in whole or in part, optionally in conjunction with additional polypeptides or polynucleotides.

Following the identification of a polynucleotide or polypeptide having desired characteristics, these can then be manufactured in quantity by well known techniques such as PCR, cloning, or expression within a host cell. The resulting polypeptides or polynucleotides may be used in the preparation of medicaments for diagnostic use, pharmaceutical use, therapy etc. This is discussed further below. Alternatively, the manufactured polynucleotide, polypeptide may be used as a research tool, e.g., antibodies may be used in immunoassays, polynucleotides may be used a hybridization probes or primers.

The polypeptides or polynucleotides generated by the method of the invention and identified as having desirable characteristics can be formulated in pharmaceutical compositions. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required.

Whether it is a polypeptide, e.g. an antibody or fragment thereof, an enzyme, a polynucleotide or nucleic acid molecule, identified following generation by the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment (e.g. decisions on dosage etc) may be determined by medical practitioners based on a number of factors, including, but not limited to, the disorder to be treated, the condition of the individual patient, the site of delivery, the method of administration and other factors known to skilled practitioners. Examples of the techniques and protocols mentioned above can be found in Remington's Pharmaceutical Sciences, 16th edition, Osol, A. (ed), 1980.

Alternatively, targeting therapies may be used to deliver the active agent more specifically to certain types of cells, by the use of targeting systems such as antibody or cell specific ligands. Targeting may be desirable for a variety of reasons; for example, if the agent is unacceptably toxic, or if it would otherwise require too high a dosage, or if it would not otherwise be able to enter the target cells.

Instead of administering these agents directly, they could be produced in the target cells by expression from an encoding gene introduced into the cells, e.g., in a viral vector (a variant of the VDEPT technique). The vector could be targeted to the specific cells to be treated, or it could contain regulatory elements which are switched on selectively by the target cells.

Alternatively, the agent could be administered in a precursor form, for conversion to the active form by an activating agent produced in, or targeted to, the cells to be treated. This type of approach is sometimes known as ADEPT or VDEPT; the former involving targeting the activating agent to the cells by conjugation to a cell-specific antibody, while the latter involves producing the activating agent, e.g. an enzyme, in a vector by expression from encoding DNA in a viral vector (see for example, EP-A-415731 and WO 90/07936).

A composition may be administered alone or in combination with other treatments, either simultaneously or sequentially depending upon the condition to be treated.

As a further alternative, the polynucleotide identified as having desirable characteristics following generation by the method of the present invention could be used in a method of gene therapy, to treat a patient who is unable to synthesize the active polypeptide encoded by the polynucleotide or unable to synthesize it at the normal level, thereby providing the biological effect of the corresponding wild-type protein.

Vectors such as viral vectors have been used in the prior art to introduce polynucleotides into a wide variety of different target cells. Typically the vectors are exposed to the target cells so that transfection can take place in a sufficient proportion of the cells to provide a useful therapeutic or prophylactic effect from the expression of the desired polypeptide. The transfected nucleic acid may be permanently incorporated into the genome of each of the targeted cells (e.g., tumor cells), providing long lasting effect, or alternatively the treatment may have to be repeated periodically.

A variety of vectors, both viral vectors and plasmid vectors, are known in the art, see U.S. Pat. No. 5,252,479 and WO 93/07282. In particular, a number of viruses have been used as gene transfer vectors, including papovaviruses, such as SV40, vaccinia virus, herpes viruses, including HSV and EBV, and retroviruses. Many gene therapy protocols in the prior art have used disabled murine retroviruses.

As an alternative to the use of viral vectors, other known methods of introducing nucleic acid into cells include electroporation, calcium phosphate co-precipitation, mechanical techniques such as microinjection, transfer mediated by liposomes and direct DNA uptake and receptor-mediated DNA transfer.

As mentioned above, the aim of gene therapy using nucleic acid encoding a polypeptide, or an active portion thereof, is to increase the amount of the expression product of the nucleic acid in the cells. In some circumstances, for example, gene therapy is directed to increasing the amount of a wild-type polypeptide in cells in which the level of the wild-type polypeptide is absent or present only at reduced levels. Such treatment may be therapeutic in the treatment of cells which are already cancerous or prophylactic in the treatment of individuals identified through screening to have a susceptibility allele and hence a predisposition to, for example, cancer.

The present invention also provides a kit for generating a polynucleotide sequence or population of sequences of desired characteristics comprising an exonuclease and components for carrying out a PCR technique, for example, thermostable DNA (nucleotides) and a stopping agent, for example, EGTA.

Also provided is a nucleic acid sequence (SEQ ID NO: 14) which encodes a novel fluorescent protein, GFP clone 53. See FIG. 14 (higher emission spectra, upper line trace). GFP clone 53, a FIND-generated derivative of GFP, possesses altered characteristics as compared to GFP (lower emission spectra, lower line trace. Such characteristics include, but are not limited to enhanced fluorescence emission relative to that of wild type GFP. The amino acid sequence (SEQ ID NO: 15) of GFP clone 53 is also provided. See FIG. 14.

The present applicants have termed the technology described herein as FIND (Fragment Induced Nucleotide Diversity).

As outlined above, the FIND program, in accordance with the present invention conveniently provides for the creation of mutated antibody gene sequences and their random combination to functional antibodies having desirable characteristics. As an example of this aspect of the invention, the antibody genes are mutated by error prone PCR which results in a mutation-rate of approximately 0.7%. The resulting pool of mutated antibody genes are then digested with an exonuclease, preferably BAL31, and the reaction inhibited by the addition of EGTA at different time points, resulting in a set of DNA fragments of different sizes. These may then be subjected to PCR based reassembly as described above. The resulting reassembled DNA fragments are then cloned and a gene library constructed. Clones may then be selected from this library and sequenced.

A further application of the FIND technology is the generation of a population of variable DNA sequences which can be used for further selections and analyses. Besides encoding larger proteins, e.g. antibody fragments and enzymes, the DNA may encode peptides where the molecules functional characteristics can be used for the design of different selection systems. Selection of recombined DNA sequences encoding peptides has previously been described (Fisch et al PNAS. USA Jul. 23, 1996; 93 (15): 7761–7766). In addition, the variable DNA population can be used to produce a population of RNA molecules with e.g. catalytic activities. Vaish et al (PNAS. USA Mar. 3, 1998; 95 (5): 2158–2162) demonstrated the design of functional systems for the selection of catalytic RNA and Eckstein (Ciba Found. Symp. 1997; 209; 207–212) has outlined the applications of catalytic RNA by the specific introduction of catalytic RNA in cells. The FIND system may be used to further search through the sequence space in the selection of functional peptides/molecules with catalytic activities based on recombined DNA sequences.

Aspects and embodiments of the present invention will now be illustrated, by way of example, with reference to the accompanying figures. Further aspects and embodiments will be apparent to those skilled in the art. All documents mentioned in this text, including: literature references, patents, and patent applications are incorporated in their entirety herein by reference.

BRIEF DESCRIPTION OF THE DRAWINGS

FIG. 6 shows FIG. 6A) the theoretical insert after restriction digestion of the fragment resulting from the primer combination FIND 1, pBR322 NheI-forward—STOP-primer with pBR322-EagI-reversed-primer. This is termed FIND 1 and SEQ ID NO: 5; and FIG. 6B) the theoretical insert after restriction digestion of the fragment resulting from the primer combination pBR322 HindIII forward primer and pBR322 SalI reverse stop primer. This is termed FIND 3 (SEQ ID NO: 6).

FIG. 7 shows the experimentally determined sequences of the two first FIND clones after automated sequencing. FIG. 7A) shows FIND 1 sequence with the STOP codon marked in bold (SEQ ID NO: 7); and FIG. 7B) shows the FIND 3 sequence with the STOP codon shown in underlined text (SEQ ID NO: 8).

FIG. 8 shows the sequence of pEXmide V (4055 bp) NcoI- and Sal I-sites are marked in underlined text (SEQ ID NO: 9).

FIG. 11A depicts the recombination frequencies observed when using dsDNA or ssDNA as starting material and FIG. 11B reveals the dependency of recombinant frequency on the enzyme concentration used to digest ssDNA.

FIG. 14 shows the (A) nucleic acid (SEQ ID NO: 14) and (B) amino acid (SEQ ID NO: 15) sequences of a novel fluorescent protein GFP clone 53.

DETAILED DESCRIPTION AND EXEMPLIFICATION OF THE INVENTION

Figure 1:
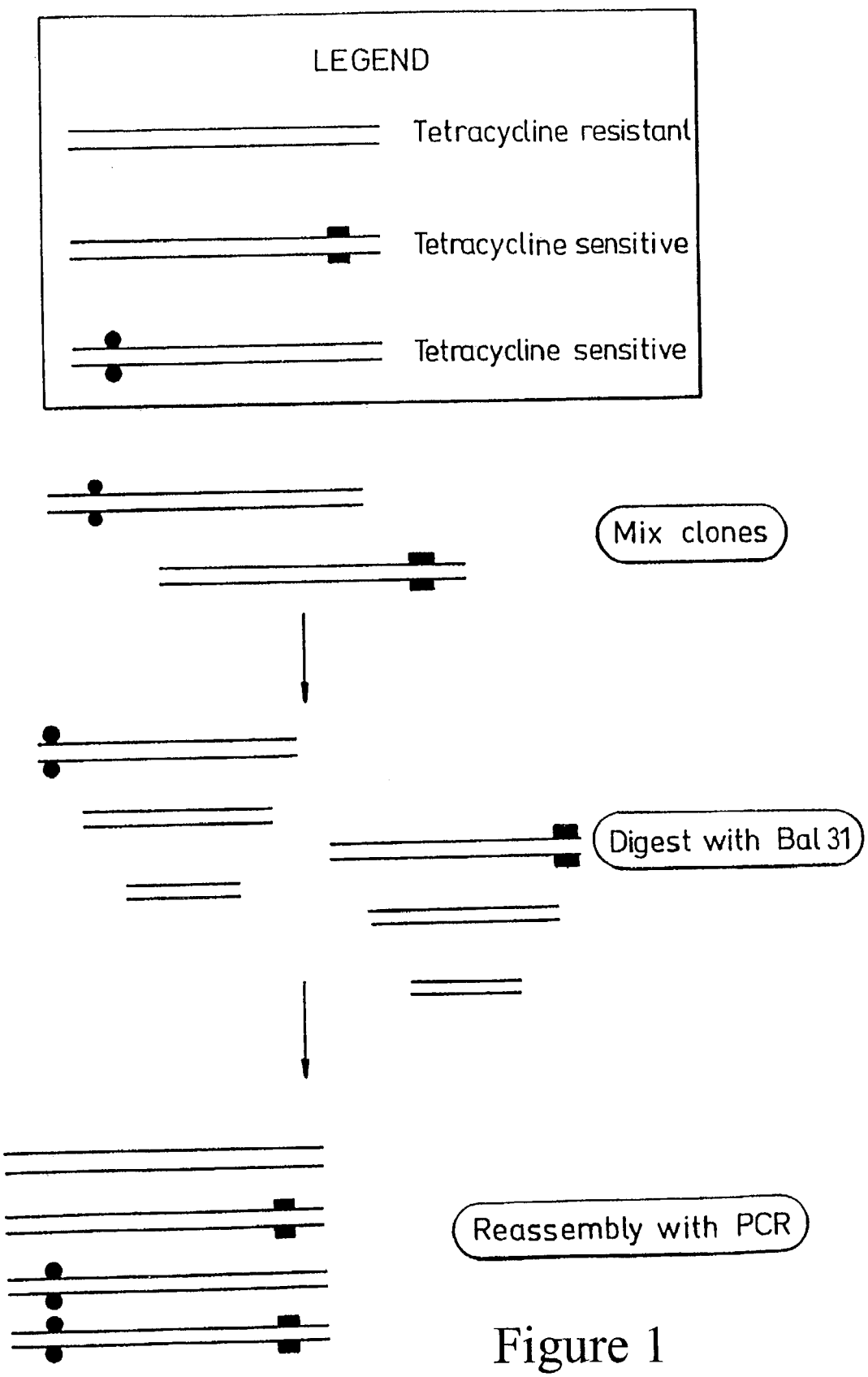
FIG. 1 shows the principle steps in the shuffling of specific DNA sequences between different clones.
Figure 2:
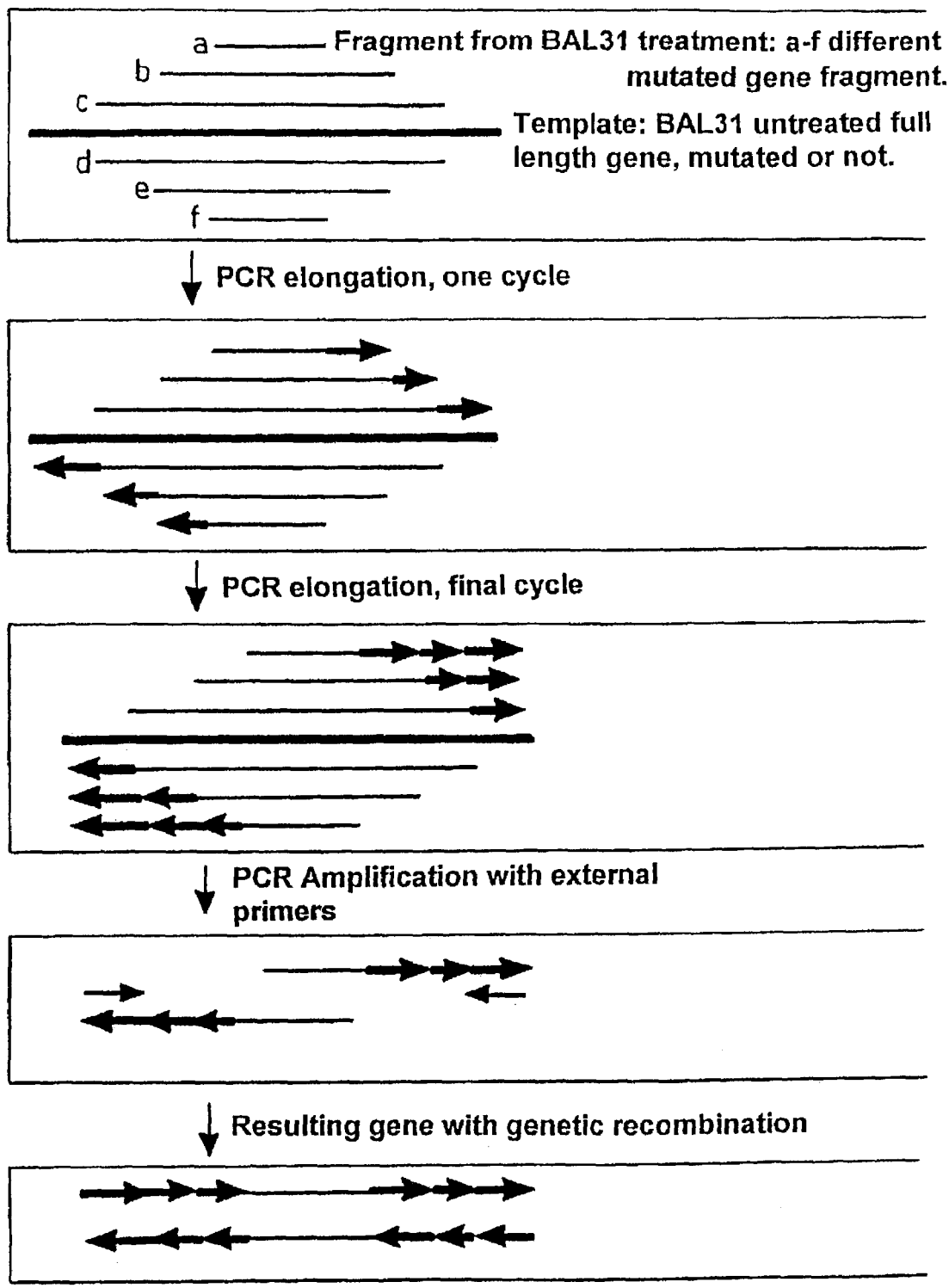
FIG. 2 shows the principle steps in the PCR elongation of exonuclease treated gene sequences.
Figure 3:
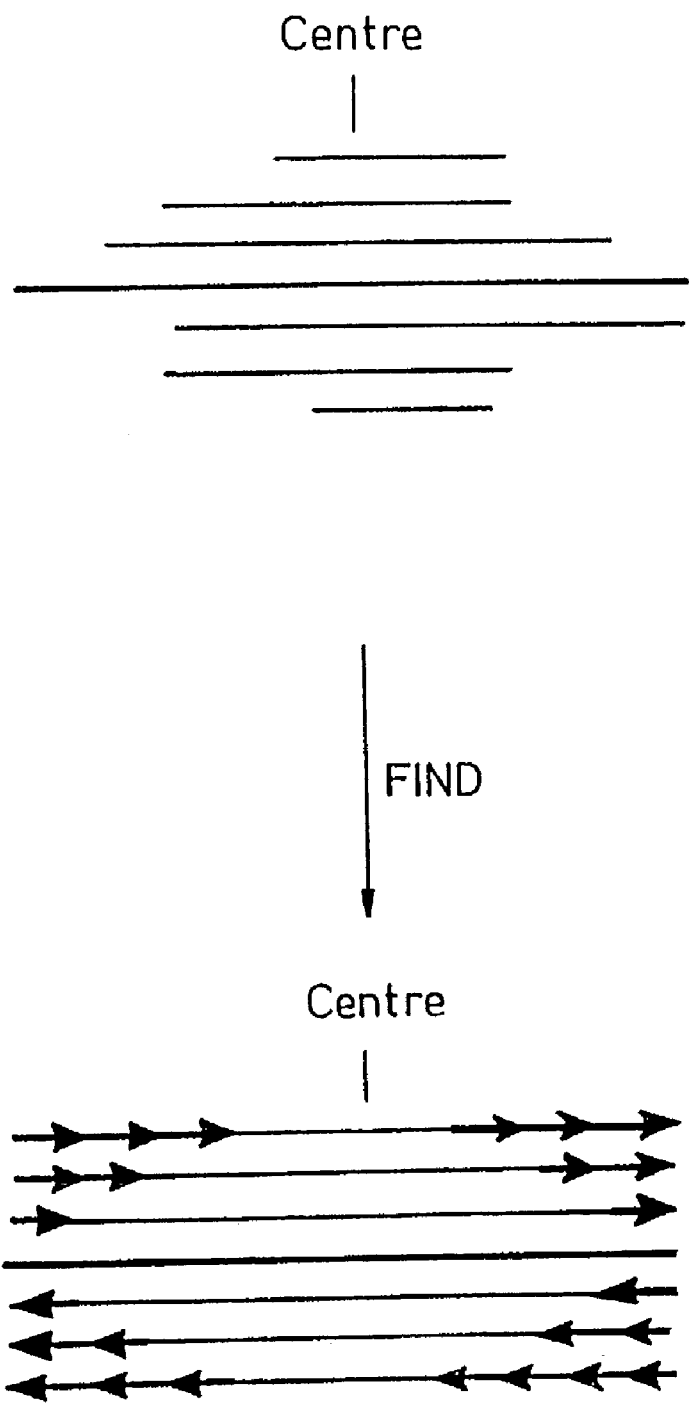
FIG. 3 shows the principle steps in the PCR elongation of long fragments of exonuclease treated gene sequences. The use of long fragments results in the middle region of the gene not being recombined. This region may, however, contain random mutations and the middle of the gene sequence may thus differ from other clones. The middle region of the sequence may differ in length, but by using longer primers the middle region may be covered.
Figure 4:
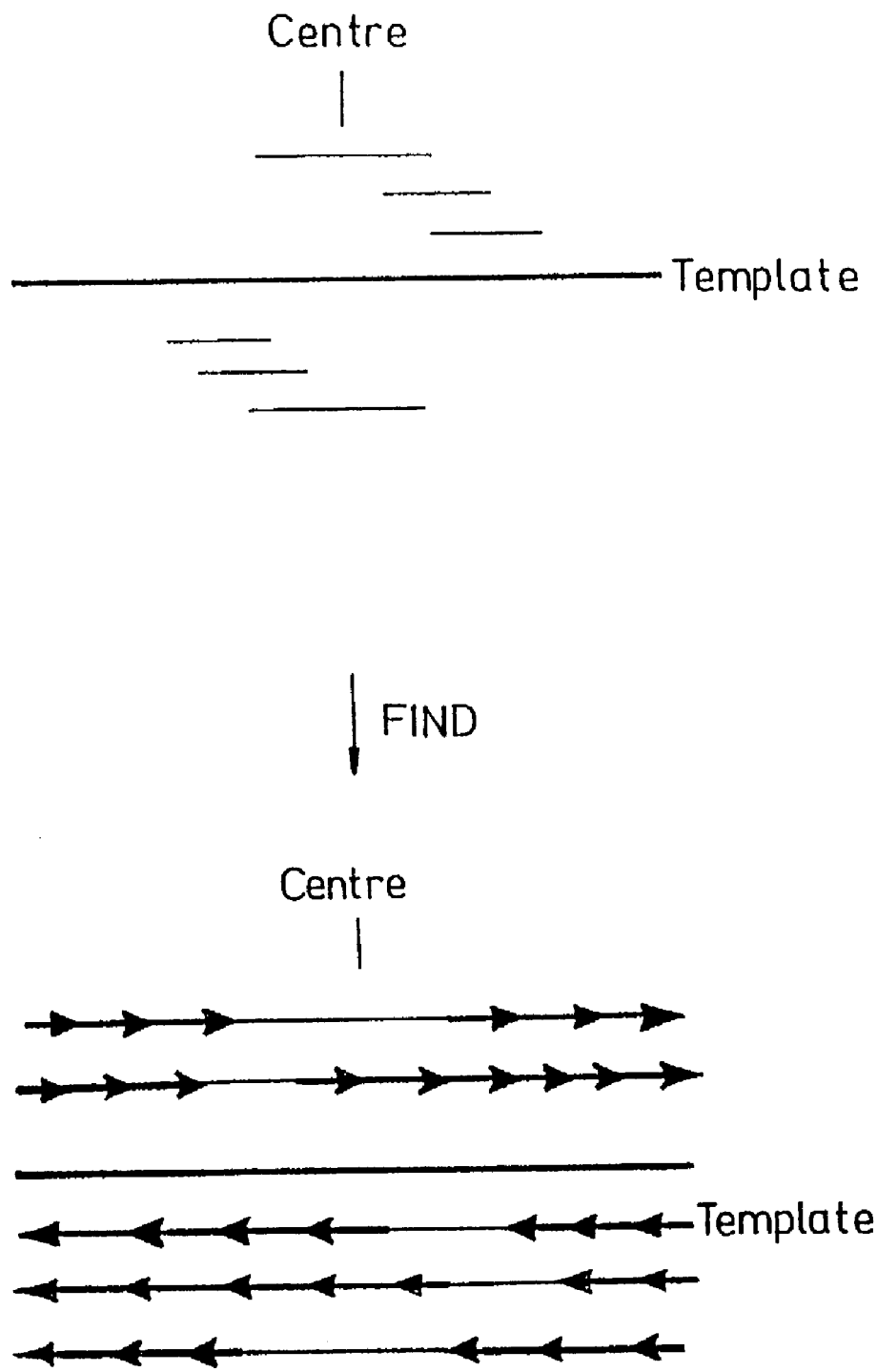
FIG. 4 shows the principle steps in the PCR elongation of short fragments of exonuclease treated gene sequences. The use of short fragments results in the middle region of the gene being recombined. If a longer reaction time is used for the exonuclease digestion a set of fragments of differing lengths are produced. If the fragments are short, some fragments will be located away from the middle region of the gene sequence thereby allowing recombination of the middle sequence.

One aspect of the DNA shuffling procedure can be illustrated by the steps shown in FIG. 1. The gene encoding the tetracycline-resistance (Tet-R) in the plasmid pBR322 is used in this example. Two clones were generated by site directed mutagenesis: one with an engineered stop codon close to the 5' terminus and one with a stop codon close to the 3' terminus of the Tet-R gene. The phenotype of these two genes is tetracycline sensitive. By mixing the two clones in equimolar amounts and digesting with BAL31, revertants were selected. After cloning the reassembled genes (with combination between the two genes carrying the two stop codons) revertants with a frequency of 16% were detected, i.e. 16% of the clones were tetracycline resistant. The experiment used the ampicillin-resistance in pBR322 for primary selection and then individual Amp-R clones were tested under tetracycline selection (see the overview in FIG. 1 and the theoretical view in FIG. 2).

A more detailed description of examples of the present invention are given below.

Reagents:

AmpliTaq® polymerase was purchased from Perkin-Elmer Corp., dNTPs from Boehringer Mannheim Biochemica (Mannheim, Germany), and BAL31 Nuclease from New England Biolabs Inc. (Beverly, USA). Klenow enzyme was purchased from Amersham.

All restriction enzymes were purchased from Boehringer Mannheim Biochemica (Mannheim, Germany). Ethidium bromide was purchased from Bio-Rad Laboratories (Bio-Rad Laboratories, Hercules, Calif., USA). T4 DNA Ligase was purchased from Appligene Inc. (Pleasanton, Calif., USA).

All primers were designed in the laboratory and synthesized with an Applied Biosystems 391 DNA-synthesiser.

PCR:

All Polymerase Chain Reactions (PCR) were carried out in a automatic thermocycler (Perkin-Elmer Cetus 480, Norwalk, Conn., USA). PCR techniques for the amplification of nucleic acid are described in U.S. Pat. No. 4,683,195. The PCR reactions were run at varying amounts of cycles consisting of following profile: denaturation (94° C., 1 minute), primer annealing (55° C., 1 minute) and extension (72° C., 1 minute) using a 1 second ramp time. The PCR reactions contained, unless otherwise noted, 5 µl of each primer (20 µW), 8 µl of DNTP (1.25 mM each of dTTP, dATP, dCTP and dGTP), 10 µl 10× reaction buffer, 0.5 µl AmpliTaq® thermostable DNA polymerase (5U/µl) (Perkin-Elmer Corp.), and water to a final volume of 100 µl. In all PCR experiments these parameters were used and the number of reaction cycles was varied. References for the general use of PCR techniques include Mullis et al, Cold Spring Harbor Symp. Quant. Biol., 51:263, (1987), Ehrlich (ed), PCR technology, Stockton Press, NY, 1989, Ehrlich et al, Science, 252:1643–1650, (1991), "PCR protocols; A Guide to Methods and Applications", Eds. Innis et al, Academic Press, New York, (1990).

Sequencing:

All constructs have been sequenced by the use of a Taq Dyedeoxy™ Terminator Cycle Sequencing Kit. The sequencing was performed on an ABI Prism 373 DNA Sequencer.

Figure 5:
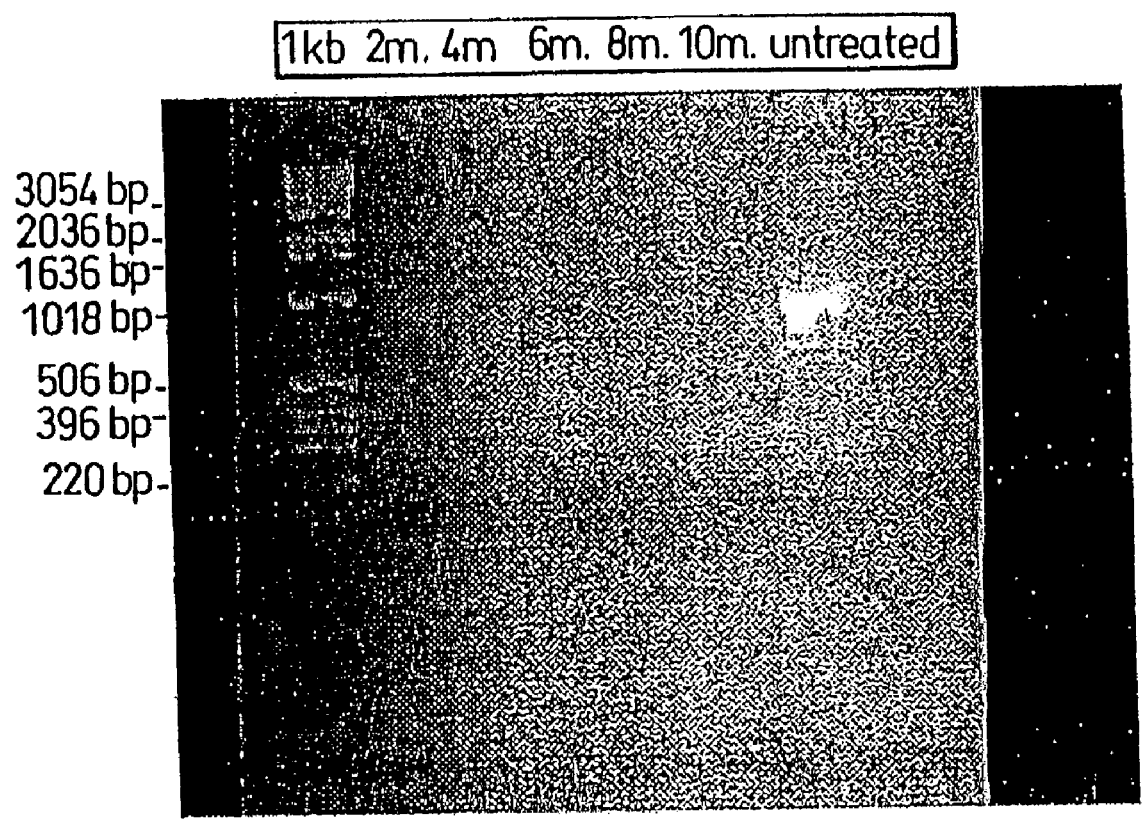
FIG. 5 shows the appearance of DNA at different fixed time intervals after digestion with BAL31 Nuclease. The DNA was mixed with the enzyme and incubated at 30° C. At different time points samples were removed and the enzymatic activity stopped by addition of 20 mM EGTA. The samples from the different time points were purified and analyzed on a 2% agarose gel. The samples are indicated as follows: 1 Kb=DNA molecular marker 1; 2–10 m=2 to 10 minutes BAL31 incubation samples.

Agarose Electrophoresis:

Agarose electrophoresis of DNA was performed with 2% agarose gels composed of 1% NuSieve® GTG® Low Melting AGAROSE (FMC Bioproducts, Rockland, Me., USA) and 1% AMRESCO® Agarose (AMRESCO, SOLON, Ohio, USA) with 0.25 µg/ml ethidium bromide in Tris-acetate buffer (TAE-buffer 0.04M Tris-acetate, 0.001M EDTA). Samples for electrophoresis were mixed with a sterile filtrated loading buffer composed of 25% Ficoll and Bromphenolic blue and loaded into wells in a 2% agarose gel. Electrophoresis was performed at 90 V for 45 minutes unless otherwise stated in Tris-acetate buffer with 0.25 µg/ml ethidium bromide. Bands of appropriate size were gel-purified using the Qiaquick Gel Extraction Kit (Qiagen GmbH, Hilden, Germany). As molecular weight standard, DNA molecular weight marker 1 (Boehringer Mannheim GmbH, Germany) was used. The DNA concentrations of the gel extracted products were estimated using a spectrophotometer (see FIG. 5).

Bacterial Strains:

The *Escherichia coli*-strain *E. coli* BMH71-18 (supE thi Δ(lac-proAB) F'[proAB+ lacI$^q$ Δ(lacZ)M15]), was used as a bacterial host for transformations. Chemically competent cells of this strain were produced basically as described Hanahan, D. 1983. Studies on transformation of *Escherichia coli* with plasmids. J. Mol. Biol. 166: 557–580. Electrocompetent cells of this bacterial strain were produced (Dower, W. J., J. F. Miller, and C. W. Ragsdale. 1988: High efficiency transformation of *E.coli* by high voltage electroporation. Nucleic Acids Res. 16:6127).

Plasmids:

The tetracycline resistance-gene of pBR322 is 1191 bp (base pairs) long. A deleted tetracycline resistance-gene variant of plasmid pBR322 was constructed by cleaving the plasmid with the restriction enzymes SalI and BamHI. This resulted in removal of a 276 bp fragment inside the tetracycline gene. A cleavage reaction with HindIII and EagI and the deleted plasmid would theoretically lead to a 634 bp cleavage-product, whereas a wildtype pBR322 cleaved with these enzymes produces a 910 bp product. The resulting protruding single stranded overhangs on the deleted plasmid after cleavage were treated with Klenow enzyme to generate double-stranded ends at both ends of the plasmid. These ends were then blunt-end ligated according to Molecular cloning; A LABORATORY MANUAL (Second Edition, Cold Spring Harbor Laboratory Press, 1989). The resulting plasmid was transformed into chemically competent *E. coli* BMH71-18 and plated onto ampicillin-containing plates (100 µg/ml). When replated onto tetracycline-containing agar plates (10 µg/ml) the colonies were tetracycline sensitive.

External Primers:

Two external primers surrounding the tetracycline gene of pBR322 were designed with the following sequences including designated unique restriction sites: pBR322 HindIII forward primer:

```
                                              (SEQ ID NO: 1)
5'-CAGCTTATCATCGATAAGCTTTAATGCGGTAGTTTAT-3'
and pBR322-EagI-reversed-primer:

(SEQ ID NO: 2)
5'-CGTAGCCCAGCGCGTCGGCCGCCATGCCGGCGATAATG-3'
```

To show that the two external primers cover the functional parts of the tetracycline-gene, a PCR reaction with the above mentioned profile was used for a 30 cycles-PCR with pBR322 (250 ng) as a template and the external primers described above. This yielded a PCR-product of 910 bp after subsequent cleavage with HindIII and EagI. When this restriction product was cloned in a likewise restriction-digested pBR322 plasmid, the plasmid encoded a tetracycline resistant phenotype. This was detected after transformation of a ligation of plasmid and 910 bp PCR-product into *E.coli* host BMH 7118 plated on tetracycline containing agar-plates (10 µg/ml).

STOP-Containing Primers:

Two pBR322 forward mutagenic primers and two pBR322 reversed primers containing unique restriction-sites and one STOP codon each at various sites were constructed. These were:

```
pBR322 NheI forward STOP:
5'-CACTATGGCGTGCTGCTAGCGCTATATGCGTTGATGCAATTTCTATGAGCACCCGTTCT-3'.     (SEQ ID NO: 3)

pBR322 SalI reversed STOP:
5'-TCTCAAGGGCATCGGTCGACGCTCTCCCTTATGCGACTCCTGCATTAGGAATCAGCCCAGTAGTA-     (SEQ ID NO: 4)
3'.
```

Generation of STOP-codon Containing Variants of pBR322 Plasmids.

Four different variants of the tetracycline gene were constructed. A combination of one mutated forward or reversed primer with the corresponding external forward or reversed primer was used in PCR-reactions to generate mutated inserts. Plasmid pBR322 was used as a template (250 ng) in 40 PCR-cycles. The resulting restriction digested fragments were then cloned into tetracycline deleted pBR322, and the resulting clones were called FIND 1 and FIND 3.

The following primer combinations were used: FIND 1, pBR322 NheI-forward-STOP-primer with pBR322-EagI-reversed-primer. This combination gave the insert after restriction digestion as shown in FIG. 6A; and FIND 3, pBR322 HindIII forward primer and pBR322 SalI reversed STOP primer. This combination gave the insert after restriction digestion as shown in FIG. 6B.

The amplified PCR-products were analyzed on a 2% agarose gel. The electrophoresis was run at 90V for 40 minutes as described above. Bands of appropriate size (1000 bp), as compared to the molecular weight standard, were cut out and gel-purified using the Qiaquick Gel Extraction Kit. The four different STOP-containing inserts were then cleaved with the restriction enzymes designated in the primers above. For each insert a pool of plasmid pBR322 was cleaved with the same enzymes, and these four combinations were then ligated and transformed into chemically competent *E coli* BMH 71-18 according to the modified protocol of Detlef (Modified Hanahan, revised M. Scott, F. Hochstenbach and D. G Rebecka Ingrid Camilla Güssow 1989). The transformants were plated onto ampicillin containing agar-plates (50 µg/ml). When replated on tetracycline containing agar plates (10 µg/ml) no colonies survived, confirming the functional effect of the introduced STOP-codon in the tetracycline gene. Plasmids of the four different FIND-clones were prepared with Qiagen Plasmid Midi Kit (Qiagen Inc., Chatsworth, Calif., USA). The plasmids of the four clones were sequenced by the use of a Taq Dyedeoxy™ Terminator Cycle Sequencing Kit. The sequencing was performed on a ABI Prism 373 DNA Sequencer. The STOP-codons were confirmed and the inserts to be correct.

Find Experiment I:

Generation of FIND-fragments for BAL31 Nuclease Digestion.

PCR-fragment of FIND 1 and FIND 3 were generated by running PCR-reactions with FIND 1 and FIND 3-plasmids as templates (500 ng) and with the two external primers, pBR322 HindIII forward primer and pBR322-EagI-reversed-primer. PCR-cycles were as described above for 30 cycles. The amplified PCR-products were mixed with 20 µl of loading buffer (25% Ficoll and Bromophenolic blue) and analyzed on a 2% agarose gel. The electrophoresis was run at 90V for 35 minutes as previously described. Bands of appropriate size were cut out and gel-purified using the Qiaquick Gel Extraction Kit. The DNA-concentration was estimated to 112.25 µg/ml for the FIND-1 PCR-fragment and to 110 µg/ml for the FIND-3 PCR-fragment.

BAL31 Nuclease Treatment:

5 µg each of FIND 1 and FIND 3 PCR-fragments (FIGS. 7 A and B) were mixed in equimolar amounts together with 100 µl of 2× BAL31 buffer and 10 µl sterile water to a final volume of 200 µl. A smaller volume of 22.5 µl was prepared to be used as an enzymatically untreated blank. This consisted of 4.5 µl FIND 1-fragment and 4.5 µl of FIND 3, 11.25 µl 2× BAL31 nuclease buffer and 2.25 µl sterile water. 1.5 ml sterile eppendorf tubes with DNA and 2× BAL31 nuclease buffer and water as described were pre-incubated in a 30° C. water-bath in a cold-room of +4° C. for 10 minutes.

Meanwhile five sterile eppendorf tubes were prepared with 4 µl each of a 200 mM solution of EGTA. These were marked 1–9 minutes. In the same way a tube with 2.5 µl 200 mM EGTA was prepared for the blank untreated DNA-solution. The working concentration of EGTA is 20 mM. After the 10 minutes pre-incubation BAL31 Nuclease was added to the tube with the larger volume to a final concentration of 1 Unit/µg of DNA (10 µl of 1 U/µl solution). After t=1, 3, 5, 7 and 9 minutes the tube was mixed and samples of 36 µl were removed and added to the tubes with 4 µl of EGTA and placed onto ice. At the same time the blank volume of 22.5 µl was removed and added to the prepared 2.5 µl of EGTA and also placed on ice. The tubes were then placed in a 65° C. water-bath for heat inactivation of the enzyme and then replaced onto ice.

Purification of Digestion Produced Fragments:

The volumes in the tubes were corrected to 100 µl each and a phenol/chloroform/isoamylalcohol extraction was performed. 50 µl of buffered phenol was added to each tube together with 50 µl of a mixture of chloroform and isoamylalcohol (24:1). The tubes were vortexed for 30 seconds and then centrifuged for 1 minute in a microfuge at 14000 r.p.m. The upper phase was then collected and mixed with 2.5 volumes of 99.5% Ethanol (1/10 was 3M Sodium Acetate, pH 5.2). The DNA was precipitated for 1 hour in −80° C. The DNA was then pelleted by centrifugation for 30 minutes in a microfuge at 14.000 r.p.m. The pellet was washed once with 70% ethanol and then re-dissolved in 10 µl of sterile water.

Analysis of Digestion Produced Purified Fragments on Agarose Gel:

5 µl of the dissolved pellet from each time point and from the blank were mixed with 2.5 µl of loading buffer (25% Ficoll and Bromophenolic blue) and loaded into wells in a 2% agarose gel. The electrophoresis and subsequent gel extraction of the different time points were performed as above.

Reassembly PCR with BAL31 Nuclease Generated Fragments:

The remaining 5 µl of the dissolved pellet from each time point after phenol-extraction and precipitation were mixed in a PCR-reassembly without primers. A portion of 5 µl from the untreated blank was added as template to make it possible to generate full length fragments. 40 PCR-cycles were run with the PCR-profile and reaction mixture as described above, but without any primers.

PCR with External Primers to Increase the Amount of Reassembled PCR-products:

50 µl of the reassembled PCR-product was mixed with PCR reagents including the two external primers as described above to generate a 100 µl PCR reaction. This PCR was run for 25 cycles with the profile described above. The amplified PCR-product was analyzed on an agarose gel. A band of approximately 1000 bp was visible on the gel after the second PCR with the two external primers. The remaining 50 µl from the first reassembly PCR, showed only a smear of bands spanning the whole interval of the molecular weight marker. The 1000-bp fragment after the second PCR was excised and gel-purified as described previously.

Restriction Digestion of Reassembled FIND-fragment and Tetracycline Sensitive pBR322 with HindIII and EagI:

10 µg of tetracycline-deleted pBR322 (10 µl) was cleaved with 2 µl each of the enzymes HindIII (10 U/µl) and EagI (10U/µl) (4U enzyme/µg vector) in a mixture with 10 µl 10× buffer B (supplied with the enzymes) and water to 100 µl. All of the agarose purified reassembled FIND-fragment was cleaved with the same enzymes in a similar 100 µl reaction mixture. The tubes were incubated in a 37° C. water bath for 14 hours.

Gel Purification of Restriction Digested Vector and Restriction Digested Reassembled FIND-fragment:

The cleavage reactions were mixed and analyzed on a 2% agarose gel. The restriction digested tetracycline-deleted pBR322 showed a cleavage product of about 600 bp. This corresponds well with the expected size of 635 bp. The band of the cleaved plasmid was cut out and gel-extracted as previously described. The reassembled cleaved FIND-product was about 1000 bp long and was gel extracted in the same manner as the plasmid.

Spectrophotometer estimations of the restriction digested-plasmid and FIND-fragment gave the following indications of DNA-concentrations: plasmid 13.5 µg/ml; reassembled cleaved FIND-fragment 77.3 µg/ml.

Ligation of Reassembled Restriction Digested FIND-fragment with Tetracycline Deleted Restriction Digested pBR322:

9.6 µg of purified, cleaved tetracycline resistance gene-deleted pBR322 was ligated to 2.76 µg purified reassembled restriction digested FIND-fragment at 12° C. water bath for 16 hours. 50 µl of the vector was mixed with 60 µl of the insert and 15 µl of 10× buffer (supplied with the enzyme) 7.5 µl ligase (5 U/µl) and sterile water to a final volume of 150 µl. A ligation of 2 µg restriction digested tetracycline resistance gene-deleted pBR322 without any insert was also performed in the same manner.

Transformation of Chemically Competent *E coli* BMH 71-18 with the Ligated Reassembled FIND-insert and pBR322:

The ligation reactions were purified by phenol/chloroform extraction as described above. The upper phase from the extraction was collected and mixed with 2.5 volumes of 99.5% Ethanol (1/10 was 3M Sodium Acetate, pH 5.2). The DNA was precipitated for 1 hour in −80° C. The DNA was then pelleted by centrifugation for 30 minutes in a microfuge at 14.000 r.p.m. The pellet was washed once with 70% ethanol and then re-dissolved in 10 µl of sterile water. 5 µl of each ligation was separately mixed with 95 µl chemically competent *E. coli* BMH 71-18 incubated on ice for 1 hour and then transformed according to the modified protocol of Detlef (Modified Hanahan, revised M. Scott, F. Hochstenbach and D. Güssow 1989). After one hour's growth the bacteria from the two transformations were spread onto ampicillin containing agar plates (100 µg/ml). The plates were grown upside-down in a 37° C. incubator for 14 hours.

Testing of Ampicillin-resistant Transformant for Tetracycline-resistant Recombinants:

The transformation with reassembled FIND-fragment and tetracycline-deleted pBR322 gave 122 ampicillin-resistant transformants. The religated cleaved empty tetracycline-deleted pBR322 gave 100 transformants. The transformants from both categories were transferred with sterile toothpicks one at a time to tetracycline (10 µg/ml) containing agar plates and to ampicillin containing plates at the same time and to corresponding locations. These plates were incubated in 37° C. incubator for 14 hours.

Counting of Tetracycline Resistant Recombinants:

The colonies on both the tetracycline plates and the ampicillin plates were counted the following day for both transformants.

Find Experiment II:

The above described methods were used for a second BAL31 Nuclease treatment with a mixture of 5 µg of FIND 1 and 5 µg of FIND 3 as described above and in the overview in FIG. 1. This time new PCR-fragments had been generated with the estimated concentrations of 192.25 µg/ml for FIND 1 and 231.5 µg/ml for FIND 3. The following reaction mixture was used: 26 µl FIND 1, 21.6 µl FIND 3, 100 µl 2× BAL31 exonuclease buffer, 9.9 µl BAL31 Nuclease and water to 200 µl. A blank was also prepared with 13 µl FIND 1 and 10.8 µl FIND 3, 361 µl 2× BAL31 exonuclease buffer, 0 µl BAL31 Nuclease and water to 72 µl.

The BAL31 digestion was performed as described in the previous experiment and samples were withdrawn at the same timepoints to tubes with 200 mM EGTA to get a final concentration of 20 mM EGTA. The exonuclease in the resulting samples was heat-inactivated as described above and the fragments where extracted, precipitated and 50% were loaded on agarose gel. After the anticipated fragment banding pattern was confirmed on the gel, the samples were purified and two sequential PCR-reactions were performed as described hereinabove. The final PCR-fragment was cloned into tetracycline deleted pBR322 under the same conditions as above. The ligation was then electroporated into electrocompetent cells as described (Dower, W. J., J. F. Miller, and C. W. Ragsdale. 1988: High efficiency transformation of *E. coli* by high voltage electroporation. *Nucleic Acids Res.* 16:6127.) and plated on ampicillin agar plates as before. Several thousands of transformants were achieved.

397 of these were transported as described above to tetracycline agar plates and ampicillin agar plates at the same time. The amount of tetracycline revertants were counted the following day after incubation in a 37° C. incubator for 14 hours.

The tetracycline recombinants were then plated for separate colonies onto new tetracycline plates. Separate colonies were then inoculated into liquid cultures comprising 1× TB-media (Terrific Broth; Molecular cloning; A LABORATORY MANUAL, Second Edition, Cold Spring Harbor Laboratory Press, 1989), supplemented with 1% Glucose and both ampicillin and tetracycline at the above concentrations, and cultured. Plasmids were isolated from these bacterial cultures using a Qiagen Plasmid Midi Kit (Qiagen Inc., Chatsworth, Calif., USA). Glycerol stocks of the overnight cultures were prepared by mixing 500 µl of bacterial culture with 215 µl of 50% Glycerol and storing these mixtures at −80° C.

A bacterial PCR-screening of 40 of the tetracycline-sensitive colonies was performed using the two external primers mentioned above to estimate the frequency of empty religated vector among these transformants. This was done with the PCR-mixture mentioned hereinabove, but scaled down to 25 µl reactions. Such reactions were inoculated with one tetracycline-sensitive bacterial colony each and the PCR-profile was performed as described above for 30 cycles. The resulting PCR-fragments were analyzed on gel as described above.

| FIND-experiment I: | |
|---|---|
| No. of amp.-resistant FIND-transformants | No. of tet-resistant FIND-Transformants |
| 122<br>Frequency of recombinants: 16% | 19 |
| No. of amp.-resistant relig. Sensitive vector | No. of tet.-resistant Relig. Vect. |
| 100<br>Frequency of recombinants: 0% | 22 |

| FIND-experiment II: | |
|---|---|
| No. of amp.-resistant FIND-Transformants | No. of tet-resistant FIND-transformants |
| 397<br>Frequency of recombinants: 5.5% | 22 |

2 out of 40 bacterially PCR-screened sensitive clones were empty religated vector. This would then make up 5% of the total number of transformants. Therefore, 20 out of 397 is empty vector. This increased the number of recombinants to 5.8%.

Find Experiment III:

The FIND procedure is not restricted to usage with tetracycline genes, but can be applied to any type of gene which encodes a protein or protein motif. This is exemplified by creating a new repertoire of antibody fragments with mutations evenly spread over the entire antibody variable genes after FIND treatment.

Single base pair mutations were introduced into the VL and VH-regions of the anti-FITC scFv antibody fragment B11 (Kobayashi et al., Biotechniques September 1997; 23(3):500–503) by the use of error prone PCR in accordance with Kuipers et al., (Nucleic Acids Res Aug. 25, 1991; 19(16):4558) except for a raise in the $MgCl_2$ concentration from 2 mM to 5 mM. This anti FITC scFv antibody fragment was constructed by the use of overlap extension PCR, and the overlap extension procedure has previously been used for the random combination of DNA variation (Soderlind et al. Gene Jul. 28, 1995;160(2):269–272).

The mutated products were then subjected to controlled degradation with BAL31 exonuclease which can be used for removing nucleotides from the termini of double stranded DNA in a controlled manner. It is predominantly a 3' exonuclease (Sambrook et al., Sambrook, J., Fritsch E. F. and Mantiatis T. Molecular Cloning-a laboratory Manual Cold Spring Harbor Laboratory Press, $2^{nd}$ edition, 1989) and removes mononucleotides from both 3' termini of the two strands of linear DNA. In addition, it also acts as an endonuclease degrading the single stranded DNA (ssDNA) generated by the exonuclease activity. Degradation is completely dependent on the presence of calcium and the reaction can be stopped at different stages by adding the calcium chelating agent EGTA. BAL31 works asynchronously on a pool of DNA molecules, generating a population of DNA of different sizes whose termini have been digested to various extents and whose single stranded DNA tails vary in length. DNA of interest is digested with BAL31 and samples are withdrawn at different times and placed in a solution with EGTA, which does not interfere with the activity of Taq polymerase. Thus, PCR based reassembly is possible directly after the digestion procedure. The average length of single-stranded tails created by digestion of linear double stranded DNA (dsDNA) is dependent both on the time of BAL31 treatment and the enzyme concentration. High enzyme concentrations of 2–5 U/ml yield an average of 5 nucleotides of ssDNA per terminus, whereas 0.1–0.2 U/ml can yield longer ssDNA.

The resultant pool of DNA fragments of varying sizes were reassembled as described hereinabove into full length scFv genes. The resulting genes were cloned into the phagemid vector pEXmide5 and the resulting library size after transformation was $5.7 \times 10^4$ cfu/µg DNA.

Single clones from the library were sequenced to estimate the genetic variability of the library. The number of mutations found, distributed over the 782 bp long VL-VH-region of the scFv antibody ranged from 1–56 (Table 1). This correlates with a mutation rate ranging from 0.13% to 7.16%, whereas the mutation rate for error prone PCR has been reported to be 0.7% (Kuipers et al., Nucleic Acids Res Aug. 25, 1991; 19(16):4558). This result demonstrates the effect of recombining mutations in a set of genes, resulting in a varied gene population which can be used in selections/screening of proteins with new and altered functions.

Reagents:

AmpliTaq™ polymerase was purchased from Perkin-Elmer Corp., dNTPs from Boehringer Mannheim Biochemica (Mannheim,Germany), and BAL31 Nuclease from New England Biolabs Inc. (Beverly, USA). All restriction enzymes were purchased from Boehringer Mannheim Biochemica (Mannheim, Germany). Ethidium bromide was purchased from Bio-Rad Laboratories (Bio-Rad Laboratories, Hercules, Calif., USA). T4 DNA Ligase was purchased from Boehringer Mannheim Biochemica (Mannheim, Germany).

Primers:

All primers were designed and synthesized at the department with a Applied Biosystems 391 DNA-synthesizer. The restriction sites introduced in each primer are underlined.

Reamplification Primers:

For error prone PCR and reamplification PCR after BAL31 treatment:

```
3'-primer DL:FITC-b11-VL3'-FLAG SAL 1:
5'-CAA CTT TCT TGT CGA CTT TAT CAT CAT CAT CTT TAT AAT CAC CTA GGA      (SEQ ID NO: 10)
CCG TCA GCT TGGT-3'

5'-primer DL:FITC B11-VH-5'NcoI:
5'-ACT CGC GGC CCA ACC GGC CAT GGC CGA GGT GCA GCT GTT GGA C-3'          (SEQ ID NO: 11)
```

Sequencing Primers:

```
Sequencing reversed pEXmide 4:    5'-GGA GAG CCA CCG CCA CCC TAA C-3'    (SEQ ID NO: 12)

pUC/M 13 reversed primer:         5'-TCA CAC AGG AAA CAG CTA TGA C-3'    (SEQ ID NO: 13)
```

Plasmids pEXmide V: 4055 bp NcoI- and SalI-sites are marked with underlined text is shown in FIG. 8.

Error Prone PCR:

The error prone PCR reactions were carried out in a 10× buffer containing 500 mM NaCl, 100 mM Tris-HCl, pH 8.8, 5 mM $MgCl_2$ 100 µg gelatin (according to Kuipers et al Nucleic Acids Res. Aug. 25, 1991;19 (16):4558) except for an increase in the $MgCl_2$ concentration from 2 mM to 5 mM)

For each 100 µl reaction the following was mixed:
dATP 5 mM: 5 µl
dGTP 5 mM: 5 µl
dTTP 10 mM: 10 µl
dCTP 10 mM: 10 µl
20 µM 3' primer: 1.5 µl
20 µM 5'-primer: 1.5 µl
10× Kuipers buffer: 10 µl
sterile millipore $H_2O$: 46.3 µl The template scFv FITC B11 in pEXmideV vector (24.5 ng/µl) was added at an amount of 42 ng. 10 µl of 10 mM $MnCl_2$ was added and the tube was visually assessed to ensure that no precipitation of $MnO2$ occurred. In the final step, 5 Units of Taq enzyme was added. The error prone PCR was performed at the following temperatures for 25 cycles without a hot start: 94° C. 1', 45° C. 1', 72° C. 1', using a 1 second ramp time, followed by a rapid cooling to 4° C. Since the resultant products were amplified using error-prone PCR conditions, they comprised multiple nucleic acid sequence mutations within the 782 bp scFv FITC. These PCR products were purified using a Qiaquick PCR purification kit and then treated with BAL31 nuclease.

BAL31 Treatment:

Purified FITC B11 amplification products generated by error prone PCR were digested with BAL31. Briefly, 1.5 ml sterile Eppendorf tubes containing DNA, 2× BAL31 nuclease buffer and water were pre-incubated at 30° C. for 10 minutes. After this pre-incubation step, BAL31 nuclease was added to all tubes, except for one control tube, at a final concentration of 0.5 Units BAL31/µg of DNA. The control tube, therefore, contained only DNA, buffer, and water. After the indicated incubation time (t=2', 4', 6', 8' and 10 minutes), the tubes were mixed and samples removed, which were added to tubes containing EGTA and placed on ice. The working concentration of EGTA was 20 mM. In parallel, samples were also removed from the control tube, which were mixed with EGTA and placed on ice. After the incubation on ice, the tubes were incubated in a 65° C. water bath to heat inactivate the enzyme and then replace on ice.

Reassembly of BAL31 Generated Fragments:

The reassembly of the generated fragment pools was performed as described hereinabove, in two sequential PCR amplifications. The first PCR was performed without the addition of any external primers by mixing equal amounts of the different digestion time pools in a standard PCR reaction. The PCR comprised 40 cycles consisting of the following profile: denaturation (94° C. for 1 minute), primer annealing (55° C. for 1 minute) and extension (72° C. for 1 minute) using a 1 second ramp time. Unless otherwise noted, the PCR mixtures contained 5 µl of each primer (20 µM), 16 µl of a dNTP mixture (1.25 mM each of dTTP, DATP, dCTP and dGTP), 10 µl 10× reaction buffer supplied with the enzyme, 0.5 µl AmpliTaq™ thermostable DNA polymerase (5 U/µl) (Perkin-Elmer Corp.) and water to a final volume of 100 µl.

The reassembled products were then reamplified using a PCR mixture containing the 3'- and 5'-external primers to generate an insert of the correct size and thereby also introducing the restriction sites NcoI and SalI for cloning into the pEXmideV vector. The PCR amplification comprised 25 cycles consisting of the following profile: denaturation (94° C. for 1 minute), primer annealing (55° C. for 1 minute) and extension (72° C. for 1 minute) using a 1 second ramp time. The PCR mixtures contained 5 µl of each primer (20 µM), 16 µl of a dNTP mixture (1.25 mM each of dTTP, DATP, dCTP and dGTP), 10 µl 10× reaction buffer supplied with the enzyme, 0.5 µl AmpliTaq™ thermostable DNA polymerase (5 U/µl) (Perkin-Elmer Corp.) and water to a final volume of 100 µl. The resultant insert was purified on a 2% agarose gel using the Qiaquick gel extraction kit (Kobayashi et al., Biotechniques September 1997; 23(3): 500–503).

Cloning in the PEXMIDEV Phagemid Vector:

The insert and vector were digested with the NcoI and SalI enzymes from Boehringer Mannheim. The insert was cleaved with 10 U enzyme/µg DNA and vector with 4 U/µg DNA. The insert was then gel purified as described previously and the vector was purified using the Microcon 100 micro concentrators (Amicon, Inc., Beverly, Mass. 01915, USA). The vector was then cleaved with a third enzyme, the Pst I enzyme, a restriction site which is located between the recognition sites for the first two enzymes. The vector was gel purified with the Qiaquick gel extraction kit (Qiagen GmbH, Hilden, Germany). Insert and purified vector were ligated with 25 U T4 DNA ligase/µg DNA (Boehringer Mannheim) at a vector to insert ratio of 590 ng vector to 240 ng insert (12:1 molar ratio) for 14 hours at 12° C. The ligation reactions were purified by phenol/chloroform extraction and ethanol precipitation and subsequently transformed into electro-competent Top 10 F' bacterial cells. The library size was determined to be $5.7 \times 10^4$ cfu/µg DNA. Glycerol stocks were produced after transformation according to J. Engberg et al (Molecular Biotechnology Vol 6, 1996 p287–310) and stored at −20° C.

Sequencing:

Individual colonies from the glycerol stock library were grown and plasmid preparations were performed with Promega Wizard Plus Minipreps DNA purification System (Promega, Madison, Wis. USA). The VL and VH inserts of these plasmids were amplified by PCR using the 3'- and 5'-external primers to generate an insert of the correct size. These inserts were then sequenced with Big Dye Dyedeoxy™ Terminator Cycle Sequencing Kit. The sequencing was performed on an ABI Prism 377 DNA Sequencer.

TABLE 1

Number of mutations in the 782 bp long scFv sequences after FIND treatment

| Clone | Number of Mutations |
|---|---|
| 1 | 1 |
| 2 | 5 |
| 3 | 8 |
| 4 | 23 |
| 5 | 50 |
| 6 | 56 |
| 7 | 10 |
| 8 | 26 |
| 9 | 38 |
| 10 | 18 |

Find Experiment IV:

The field of protein engineering has proven to be an area of great expansion during the past decade and has been essential to the advancement of scientific knowledge regarding protein activity and structure-function relationships. It has also been used to advantage to engineer proteins having properties particularly well suited to different applications, including industrial appplications. Indeed, many new technologies have been developed that provide extremely efficient methods for the production of proteins having improved and desirable characteristics. This expanding area of research continues to evolve and is referred to herein as directed evolution.

Protein engineering was originally performed by directed mutagenesis of amino acid residues, the alteration of which was anticipated to improve protein activity. Comparative analysis of protein structure was generally the method of choice in the determination of the optimal sites for mutagenesis (15,21). This approach is often referred to as rational design of proteins.

Directed evolution technologies, on the other hand, essentially mimic the process of natural selection. In this process, the evolution of a protein proceeds via selection for those variant proteins in a diverse pool that are capable of adapting to different environmental conditions. A variant protein (e.g., a mutant) having improved properties possesses a selective advantage over those lacking such features. Eventually, the selective advantage of these variants produces a population of proteins having the altered properties of the progenitor variant protein. Unlike natural selection, in which similar processes take generations and generations, directed evolution is a rapid process. Directed evolution is accelerated by initiating the process using a vast pool comprised of essentially all possible variants of a protein and by providing stringent selection means. Moreover, the effectiveness of directed evolution as a tool for protein engineering is largely dependent upon maximum coverage of the nucleic acid sequence or sequence space involved to produce the greatest diversity of protein variants.

One frequently applied strategy involves simple recursive mutagenesis methods wherein point mutations are introduced in an additive manner and mutants possessing a selective advantage are preserved in subsequent selection steps (4,22). This is a laborious method and relatively time consuming. In 1994, Stemmer (23,24) introduced the method of DNA shuffling, wherein functional mutations are recombined among a set of homologous sequences, and a greater portion of sequence space is covered in a more efficient manner. Functional recombination can be performed among homologous genes generated by random mutagenesis experiments (27) or among naturally occurring homologous genes isolated from living organisms (5,9). These methods have been successfully applied to a variety of proteins and resulted in the production of proteins having altered properties. Such altered properties include, for example, enhanced enzyme stability (8,14), modified enzyme enantioselectivity (10,17), improved enzymatic activity (25), and the creation of new metabolic pathways (20).

The principle behind functional recombination involves cleaving the genes in question into smaller parts, which are rejoined such that fragments from different source genes are combined to produce novel genes having altered/improved properties. The fragmentation can be accomplished by, for example, enzymatic cleavage of existing DNA (12,13,23) or de novo synthesis of fragments by PCR (7,26). The recombination step can be performed by, for example, standard PCR (23), modified PCR (28), or ligation (16,18,19). The above approaches have various limitations with regard to homology requirements, knowledge of the sequences involved, controllability, recombination frequencies, library sizes, library diversities, and library functionalities.

A method for directed evolution, designated Fragment Induced Diversity (FIND), is provided herein. FIND technology provides a sensitive (i.e., highly controllable), process which yields high recombination frequencies and extremely diverse libraries. Moreover, FIND may be used to particular advantage because it does not introduce unwanted mutations and thus produces libraries of high functionality. It is based on exonucleolytic fragmentation of DNA followed by random recombination using PCR. Herein, a proof of principle for the FIND method is provided and applications of FIND technology in the generation of proteins having desirable characteristics are exemplified. Results from FIND experiments in which a number of parameters, including fragment size and the nature of the parental genes, were varied are provided. As shown herein, these experiments revealed surprising results regarding the impact of such variations on the frequency of the generation of productive recombinants.

The following methods and materials are provided to facilitate the practice of the following aspect of the invention.

Plasmids. A tetracycline-deleted variant of plasmid pBR322 was constructed by cleavage with SalI and BamHI (Roche, Basel, Switzerland), Klenow treatment (Amersham Biosciences AB, Uppsala, Sweden), and blunt-end ligation (New England Biolabs, MA, USA). The resulting plasmid was assessed for tetracycline sensitivity and is referred to herein as pBR322dtet. pBR322stop1 and pBR322stop3 were created by PCR amplification of the tetracycline gene of pBR322 using specific primers (see Table 2). Each mutated tetracycline gene was cloned into pBR322.

TABLE 2 shows the primer sequences used in the FIND methods.

Primer sequences pBR322 NheI forward stop:
5'-CACTATGGCGTGCTGCTAGCGCTATATGCGTTGATGCAATTTCTATGAGCACC CGTTCT-3' (SEQ ID NO: 3)

pBR322 EagI reversed:
5'-CGTAGCCCAGCGCGTCGGCCGCCATGCCGGCGATAATG-3' (SEQ ID NO: 2)

pBR322 HindIII forward:
5'-CAGCTTATCATCGATAAGCTTTAATGCGGTAGTTTAT-3' (SEQ ID NO: 1)

pBR322 SalI reversed stop:
5'-TCTCAAGGGCATCGGTCGACGCTCTCCCTTATGCGACTCCTGCATTAGGAATC AGCCCAGTAGTA-3' (SEQ ID NO: 4)

Polymerase Chain Reaction (PCR).

Unless otherwise noted PCR reactions contained 4 µM of each primer, 160 µM DNTP (Roche, Basel, Switzerland), 1× AmpliTaq reaction buffer, and 2.5 U AmpliTaq thermostable DNA polymerase (Applied Biosystems, CA, USA). The following PCR cycles were performed as indicated. FIND PCR 1: 5 or 25 cycles of 94° C. for 30 seconds (s); 50° C. for 45 s; 72° C. for 1 minute; and 72° C. for 7 minutes, no external primers were included. FIND PCR 2: 15, 25 or 50 cycles of 94° C. for 30 s; 55° C. for 45 s; 72° C. for 1 minute; and 72° C. for 7 minutes with external primers included.

Single Stranded DNA (ssDNA) Preparation.

The gene of interest was amplified using specific primers, one of which was biotinylated. Sense and antisense strands derived from the ssDNA were purified using streptavidin-magnetic beads (purchased from either Dynal AS, Oslo, Norway or Miltenyi Biotec, Bergisch Gladbach, Germany) according to the manufacturers' recommendations. The ssDNA obtained was further purified either by ethanol precipitation or using RECOCHIP (TaKaRa, Shiga, Japan) according to manufacturers' recommendations.

FIND Experiments.

The FIND experiments were initiated by digesting DNA with an exonuclease. The DNA sequences digested included a tetracycline resistance gene (pBR322stop1 or pBR322stop3, 945 bp), a scFv antibody fragment gene (CT17, sMUC or F8, 780 bp), and an antibody VH region gene (5D12, 314 bp). The DNA was either single or double stranded and prepared as indicated above or by PCR. The exonucleases used included BAL31 (0.08–1 U/µg DNA, New England Biolabs, Me., USA), exonuclease I (100 U/µg DNA, New England Biolabs, Me., USA), T7 gene 6 exonuclease (320 U/µg DNA, USB, Cleveland Ohio, USA), and exonuclease V (12.5 U/µg DNA, USB, Cleveland Ohio, USA). The digestion time was varied within the range of 2–90 minutes. The digestion reactions were stopped by adding EDTA to a final concentration of 20 mM and/or heat inactivation at 65° C. or 95° C. for 10 minutes. When EDTA was used to terminate a digestion reaction, the DNA was further purified by phenol/chloroform extraction and ethanol precipitation. The fragments were recombined in a FIND PCR 1 reaction for 5 or 25 cycles (as indicated) and the material was amplified in a FIND PCR 2 reaction for 15, 25 or 50 cycles. Full-length genes were cloned into pBR322dtet at HindIII and EagI sites (New England Biolabs, Me., USA), wherein they were screened for functionality, or into pGEM (Promega, Madison, Wis., USA), wherein they were sequenced.

Evaluation of Functionality of Tetracycline Clones.

The clones introduced into pBR322dtet were transformed into competent TG1 E. coli, which were plated on LB agar plates containing 1 µg/ml ampicillin. One to two hundred clones were re-streaked onto LB agar plates containing 50 µg/ml tetracycline. The frequency of tetracycline resistant clones was calculated based on the number of tetracycline resistant clones evident.

Selection of GFP Clones.

The GFP gene was excised from the commercially available PGFP plasmid (Clontech; 3). Random mutations were introduced into the GFP gene by error prone PCR according to Cadwell and Joyce (1,2). The point-mutated GFP genes were cloned into the indicated vector, which was transformed into E. coli TG1 and plated on LB plates. Using a standard UV light box, the 100 brightest colonies were selected and pooled. These colonies were used as a template for PCR reactions with biotinylated oligos. ssDNA from sense and antisense strands were purified and used as starting material for digestion with BAL31. Fragments of DNA from different digestion time points were reassembled into full-length DNA using PCR and further cloned into the indicated vector. The brightest colonies were cultured until reaching an $OD_{600}$ of 0.5 and whole cell fluorescence spectra were obtained with a luminescence spectrophotometer.

Results

Proof of Principle.

FIND technology is an in vitro protein evolution system wherein small blocks of genetic information (i.e., nucleic acid sequence blocks) may be recombined to provide optimal building blocks for incorporation into an engineered protein having improved characteristics. The technology utilizes exonucleases for fragmentation of DNA. The resulting DNA fragments may then be reassembled in two PCR reactions.

Figure 9:
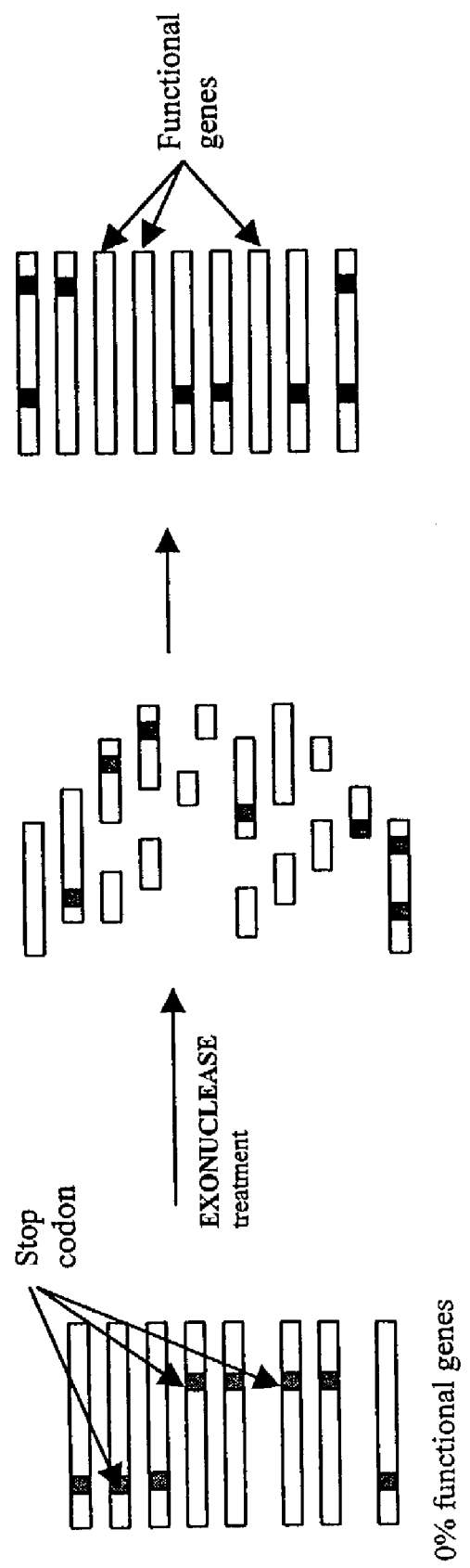
FIG. 9 shows a schematic of the steps involved in performing FIND™ technology when applied to a model system based on the tetracycline resistance gene. Stop codons were introduced at two different sites in separate constructs, thereby producing two versions of non-functional tetracycline resistance genes to be tested. The frequency of functional genes after FIND treatment was evaluated.

The FIND system was first tested by using the tetracycline resistance gene, Tet(A), as a selection marker for recombination. Two different variants of this gene were constructed, each containing a premature stop codon at a different position. Fragments of these clones were generated by treatment with either exonuclease or BAL31, mixed, and then recombined randomly into full length genes by PCR (FIG. 9). The reassembled genes were recloned and functional clones were identified as viable tetracycline resistant colonies.

Parameters that Influence the Result of a FIND Experiment

In order to improve the FIND technology, different experimental parameters were varied to investigate the impact of such changes on the functional outcome of the process.

Figure 10A:
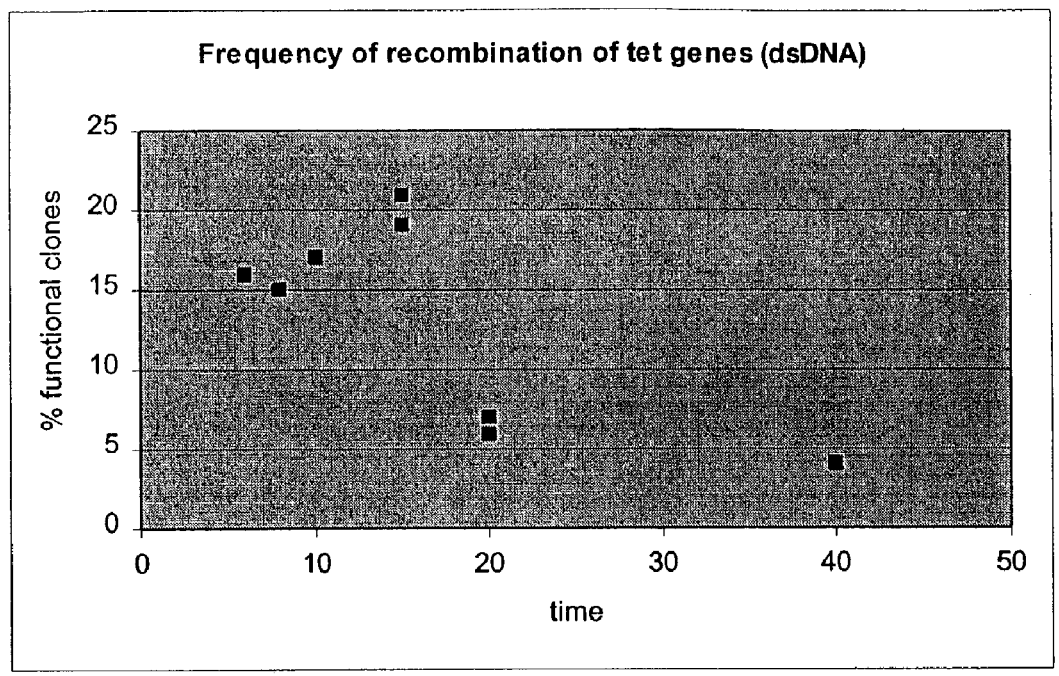
FIGS. 10A and B show graphs of the frequency of recombinant genes produced using FIND™ technology. The tetracycline resistance model system was used to examine the frequency of recombination as a function of fragmentation time.

Time. Since an exonuclease digests DNA from the ends and cleaves off one nucleotide at a time, fragments of all possible sizes were created readily by stopping the enzymatic reaction at various time points. In brief, the duration of the digestion time is inversely correlated with the size of the resultant fragments produced. Using the tetracycline resistance model system described hereinabove and keeping each time point separate, the dependency between fragmentation time and functionality of the recombinants was investigated. As shown in FIG. 10A, an optimal level of end-product functionality was attained after a particular range of fragmentation time. In this experiment, in which the enzyme concentration was constant and each digestion time point was maintained separately, a digestion time of about 15 minutes resulted in the production of ~20% functional genes.

Figure 10B:
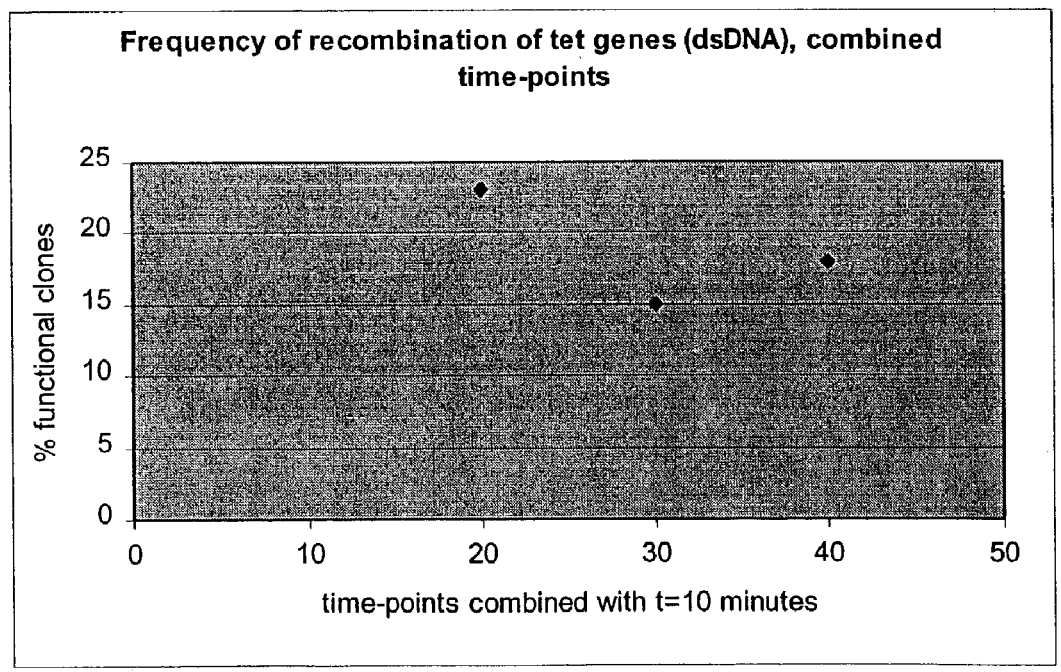

To evaluate if combinations of smaller fragments, derived from prolonged digestion times, and larger fragments could improve the results even further, fragments from different time points were combined with large fragments generated after 10 minutes of digestion (FIG. 10B). As shown, the maximum frequency of functional genes generated improved slightly. Notably, higher frequencies of functional end-products were achieved over a broader range of fragmentation times.

Double or single stranded DNA. As described herein, experiments were performed to compare the utility of single stranded versus double stranded DNA in the methods of the present invention. Of note, there is a tendency for double stranded fragmented genes to form homoduplexes rather than heteroduplexes upon PCR-mediated recombination (13). Clearly, the formation of homoduplexes would lead to the re-generation of the parent polynucleotides and thus, render the process of limited utility for the production of novel polynucleotide sequences. When engineering novel polynucleotides by shuffling different family member genes, therefore, it is important to achieve an efficient recombination frequency in order to optimize the diversity of the end-product shuffled polynucleotides.

In order to evaluate the effects of altering various experimental parameters on recombination frequency among family member genes, three different scFv antibody fragments (CT17, SMUC, and F8) were used as starting material for FIND-mediated DNA shuffling. These scFvs differ only in the six hypervariable loops. For these experiments, double stranded and single stranded polynucleotides encoding each of the three scFv antibodies were isolated. For clarity, the procedures for double stranded and single stranded polynucleotide starting material will be described separately.

An equimolar mixture of the three scFv double stranded polynucleotides was used in fragmentation reactions and fragmented double stranded polynucleotides were reassembled by PCR to produce full length genes. For single stranded shuffling experiments, plus and minus strand populations for each of the scFv fragments were generated by PCR amplification. The plus strand was amplified using a biotinylated primer, the incorporation of which facilitated the isolation of the biotinylated plus strand PCR product using streptavidin-magnetic beads. The complementary strand, the minus strand, was also amplified in parallel using an unbiotinylated primer. The minus strand PCR product, therefore, remained in solution after affinity purification of the biotinylated plus strand with streptavidin-magnetic beads.

Figure 11A:
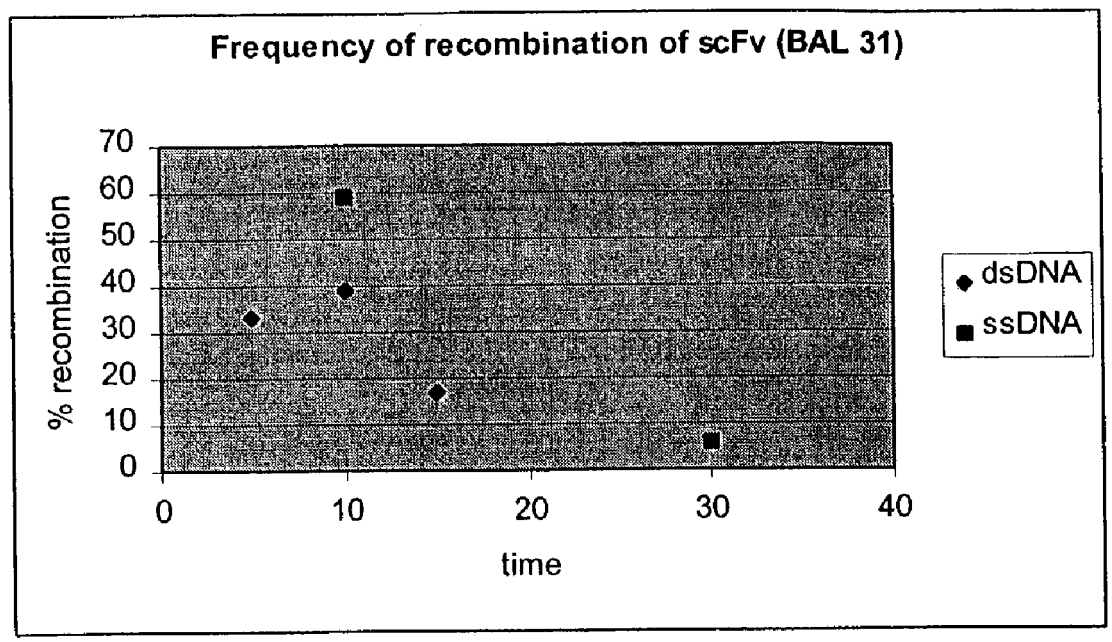
FIGS. 11A and 11B show graphs of the frequency of recombinant genes produced using FIND™ technology.

Equimolar mixtures comprising either the plus strands or the minus strands of the three scFv polynucleotides were generated. The plus and minus single stranded polynucleotide population mixtures were digested separately to produce plus and minus single stranded fragments. The resultant fragmented plus and minus single stranded populations were subsequently mixed and reassembled by PCR to produce full length genes. Shuffled full length genes derived from double stranded or single stranded starting material were subcloned and individual clones sequenced. An optimum in recombination frequency was identified, which was dependent on the duration time of fragmentation. See FIG. 11A.

These experiments revealed the surprising result that the frequency of clones having at least one recombination event was significantly higher for shuffled single stranded digested DNA than for shuffled double stranded digested DNA. Sixty percent of the clones derived from shuffling single stranded starting material had a least one recombination, whereas only forty percent of such recombinants was obtained following shuffling of double stranded starting material. The actual recombination frequencies were probably higher than indicated because the above scFv antibody fragment genes possess long stretches of homology, the presence of which would favor multiple recombination events.

The foregoing data clearly show the superior and unexpected results achieved when populations of plus or minus single stranded nucleic acids are used as starting material for exonucleolytic digestion and the resultant single stranded fragments are subsequently utilized in the DNA shuffling methods of the present invention.

It will be appreciated by those of skill in the art that other methods for differentially labeling and/or isolating populations of single stranded plus or minus strands exist. The invention is, therefore, not limited to the particular methods for the isolation of plus and minus single strand populations that are described herein.

Figure 11B:
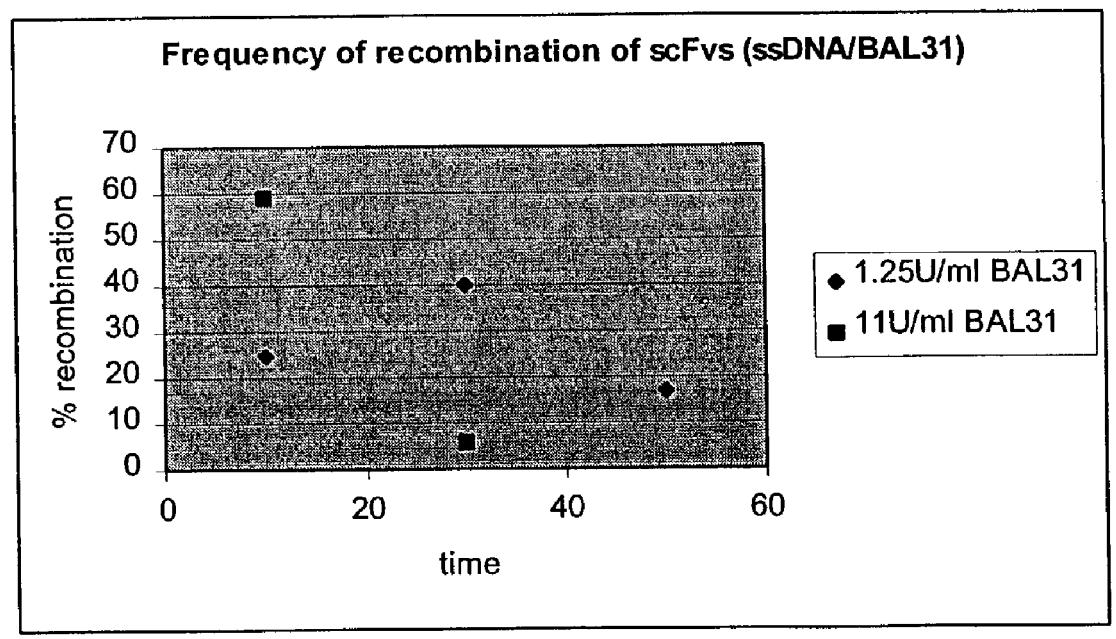

Enzyme concentration. Higher enzyme concentrations are known to promote a faster fragmentation rate and thus shorter fragments, whereas lower enzyme concentrations produce longer fragments. Using the three scFv antibody fragments described above, the influence of enzyme concentration on the recombination frequency was evaluated for single stranded DNA starting material. The experiments were performed using 1.25 or 11 U BAL31/ml and fragments generated during 10 to 50 minute digestion times were used as starting material for PCR-mediated shuffling. The enzyme concentration clearly played an important role in the outcome of such recombination experiments. Depending on the conditions selected, recombination frequencies ranging from 5–60% were achieved. See FIG. 11B.

Different exonucleases. As shown herein, higher frequencies of recombination were achieved using ssDNA as starting material for fragmentation in the FIND process. The exonuclease BAL31 is predominately a 3' exonuclease that removes mononucleotides from the 3' termini of both strands of a linear double stranded DNA. BAL31 can also, however, degrade the single-stranded DNA ends generated as a consequence of the 3' exonuclease activity on the double stranded DNA. BAL31 acts on ssDNA by removing mononucleotides exclusively from the 5' termini. Utilization of BAL31 alone to digest ssDNA into fragments for use in the reassembly of full length genes should, therefore, theoretically produce one cross-over per gene.

To examine the influence of using different exonucleases for the fragmentation of ssDNA in the FIND process, the frequency of productive recombinants generated from shuffling fragments digested with a variety of exonucleases (e.g., Exonuclease I, Exonuclease V, Exonuclease VII, and BAL31, T7 gene 6, and RecJ exonucleases) was determined. Exonuclease I is known to have 3' activity only, whereas BAL31, T7 gene 6 and RecJ exonucleases have 5' activity only. Exonuclease V and Exonuclease VII have activity at both 5' and 3' ends.

Figure 12A:
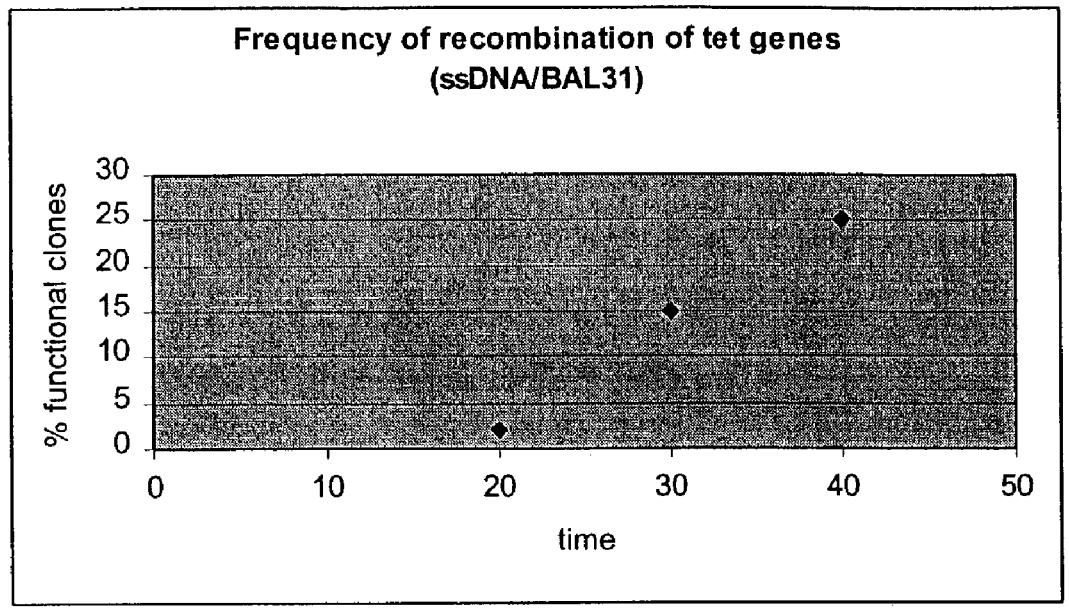
FIGS. 12A, B, C, and D show graphs of the frequency of recombinant genes produced using FIND™ technology. Results are presented for ssDNA digested with A) BAL31 exonuclease, B) exonuclease I, or C) T7 gene 6 exonuclease to generate ssDNA fragments for recombination into functional tetracycline (tet) genes.

In order to show that these exonucleases are of utility in the fragmentation step of a FIND process and yield functionally recombined genes, the tetracycline resistance gene model system was utilized. As shown herein, BAL31, Exonuclease I, and T7 gene 6 exonuclease all worked well in the FIND procedure. See FIGS. 12A, B, and C, respectively. Moreover, the recombination frequency observed was dependent on fragmentation time. The activity of RecJ was, however, too low to yield any functional fragmentation. Alterations in various parameters of the experiment could, however, render RecJ useful in the FIND process.

In theory, if only one enzyme that digests ssDNA from only one end is used, only one cross-over will occur. Additional cross-overs could, however, be obtained if DNA fragments generated following treatment with different exonucleases were shuffled in the FIND process. Exonuclease V and Exonuclease VII treatment, for example, produced small fragments which were digested from both the 5' and 3' ends. For some applications, such 5' and 3' ends are useful for the amplification step of the recombined material in the final PCR reaction. These DNA fragments may, therefore, be used to advantage in combination with DNA digested from either the 5' or 3' end to produce shuffled recombinants having improved properties.

Figure 12B:
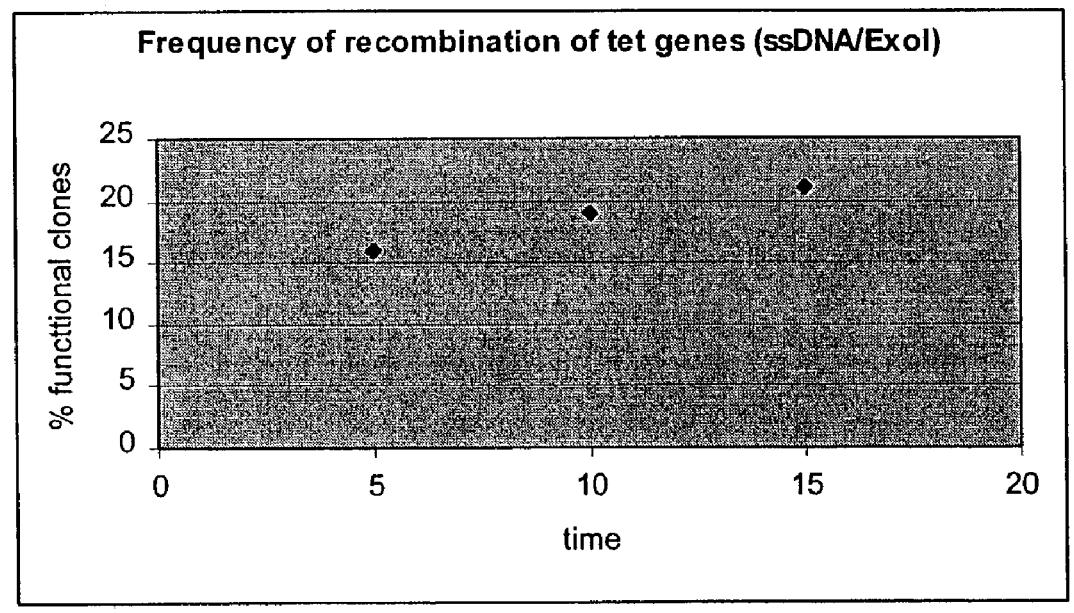
FIG. 12D shows recombinant frequencies observed when fragments generated by digestion with exonuclease I for 10 minutes were combined with fragments from digestion with exonuclease V.
Figure 12C:
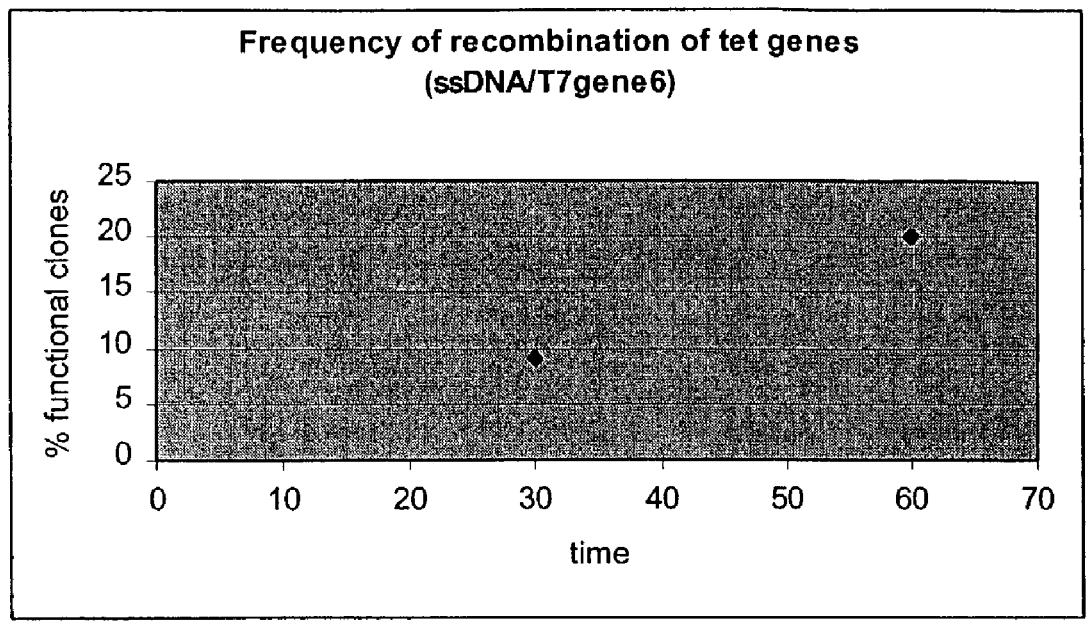
Figure 12D:
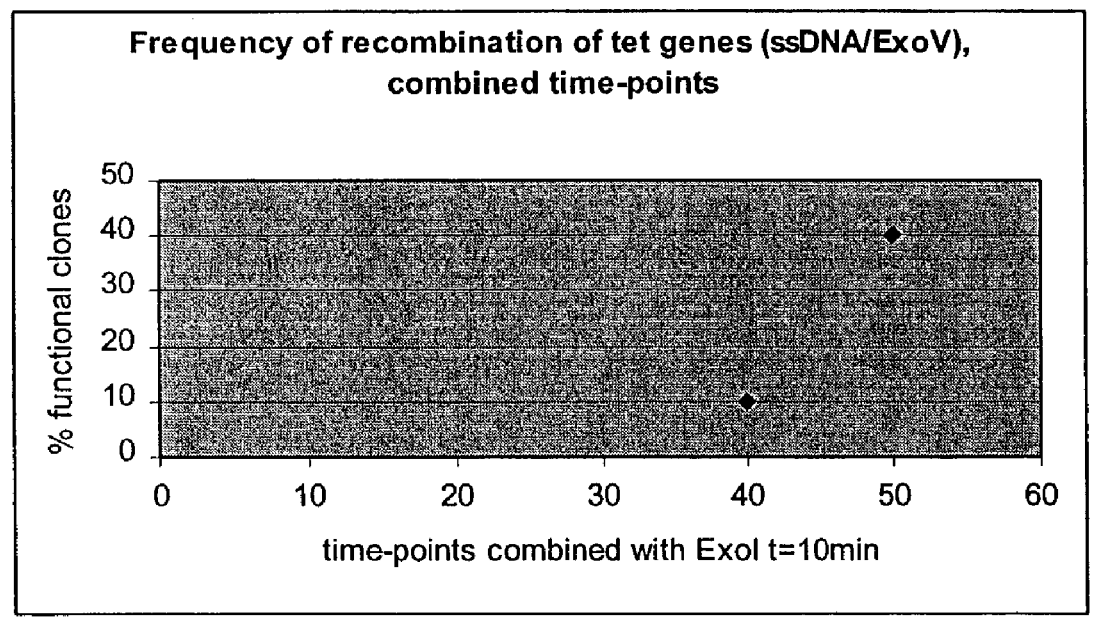

As shown in FIG. 12D, the use of a combination of ssDNA treated with Exonuclease I for 10 minutes and ssDNA treated with Exonuclease V for 50 minutes in the FIND process resulted in an increase in the frequency of functional clones generated. Functional clones comprising up to 40% were obtained. The attainment of 40% functional clones represented a significant improvement over the maximum frequency of functional clones obtained using single enzyme-digested fragments. See FIGS. 12A–C. Functionally recombined clones have also been obtained by shuffling populations of fragments generated by digestion with either Exonuclease I or Exonuclease VII for different time points. Populations of fragments generated by digestion with either T7 gene 6 exonuclease or Exonuclease VII for different time points have also been shuffled to produce functional recombined polynucleotides and/or polypeptides (data not shown).

Introduction of mutations. The use of a high fidelity system, whereby uncontrolled mutations are not introduced, is particularly advantageous for processes directed to in vitro evolution. The introduction of unwanted point mutations at random sites during the recombination step may result in the production of non-functional proteins. In order to evaluate if such mutations were introduced during the course of the FIND process, the frequency of such mutations was determined in experiments in which the VH gene from 5D12 (an anti-CD40 antibody; Kwekkebom et al. 1993. Immunology 79:439-44) was used as the double-stranded starting material. In these experiments, two different concentrations of BAL31 were used in the fragmentation step (see Tables 3 and 4) and samples from different time points were combined prior to PCR-mediated reassembly. The second PCR reaction was performed for either 15 or 50 cycles, as indicated. The resultant full length genes were cloned and sequenced to determine the number of mutations introduced during the procedure. The results presented herein demonstrate that the FIND technology introduced very few mutations, irrespective of enzyme concentration, fragmentation time, and the number of PCR cycles performed. See Tables 3 and 4. Increasing the number of PCR cycles did, however, correlate with an increase in Taq-mediated errors under all experimental conditions. See Tables 3 and 4.

TABLE 3 shows mutations introduced during a FIND experiment using 0.1 U of enzyme and varying times for digestion and nunibers of PCR cycles.

| FIND experimental conditions | # of sequences analyzed | # of mutations (not Taq mediated) | # of Taq mediated mutations | Mutations/base (Total) |
|---|---|---|---|---|
| 0.002 U/µg DNA 4 minute digestion 15 cycles | 17 | 1 (C-T) | 0 | 0.018% |
| 0.002 U/µg DNA 10 minute digestion 15 cycles | 16 | 1 (C-A) | 0 | 0.017% |
| 0.002 U/µg DNA 10 minute digestion 50 cycles | 18 | 1 (G-C) | 8 | 0.15% |

TABLE 4 shows mutations introduced during a FIND experiment using 5 U of enzyme and varying times for digestion and nunibers of PCR cycles.

| FIND experimental conditions | # of sequences analyzed | # of mutations (not Taq mediated) | # of Taq mediated mutations | Mutations/base (Total) |
|---|---|---|---|---|
| 0.125 U/µg DNA 4 minute digestion 15 cycles | 16 | 1 (C-A) | 0 | 0.019% |
| 0.125 U/µg DNA 10 minute digestion 15 cycles | 18 | 1 (C-T) 2 (G-A) | 0 | 0.05% |
| 0.125 U/µg DNA 10 minute digestion 50 cycles | 17 | 1 (G-C) | 4 | 0.089% |

The number of mutations introduced during the course of FIND procedures wherein error prone conditions had been used in the reassembly PCR step was also evaluated. See Table 5. In the first experiment, excess manganese (Mn) in the buffer (0.5 mM $MnCl_2$) was used to enhance the error rate. In the second experiment, a buffer comprising excess Mn and altered nucleotide composition was used to augment the incorporation of errors as previously described by Cadwell and Joyce (2). These error prone conditions were shown to increase both FIND-generated mutations and Taq-mediated errors.

TABLE 5 shows the type and frequency of mutations introduced during a FIND experiment under error prone conditions.

| FIND experimental conditions | # of sequences analyzed | # of mutations (not Taq mediated) | # of Taq mediated mutations | Mutations/base (Total) |
|---|---|---|---|---|
| 0.125 U/µg DNA 8 minute digestion 15 cycles with 10 × mut. buffer | 15 | 2 (C-T) 1 (G-C) 1 deletion | | 0.085% |
| 0.125 U/µg DNA 8 minute digestion 15 cycles with 10 × mut. buffer and DnTP (EP) | 20 | 2 (G-A) 1 deletion | 4 | 0.11% |

10 × mut. buffer: 10 × mutation buffer
dNTP (EP): error prone dNTP concentration Application of FIND technology to Green Fluorescent Protein. A double-stranded wildtype GFP gene was point-mutated using error prone PCR and the resultant randomly mutated GFP genes were cloned into the indicated expression vector. TG1 bacterial cells (*E. coli*) were transformed with the above expression vectors comprising mutated GFP molecules and plated on LB plates. The 100 brightest bacterial colonies were selected and pooled using a standard UV light box. These colonies were used as a template for PCR reactions with biotinylated oligonucleotides to provide means to isolate populations comprising either single stranded plus or minus strands as described hereinabove.

Populations of ssDNA nucleic acid sequences comprising either sense and antisense strands were purified and used as starting material for digestion with BAL31. Populations of fragments of single stranded plus or minus strand nucleic acids derived from different digestion time points were mixed, shuffled, and reassembled into full-length GFP molecules as described herein. The resultant recombinants were cloned into the indicated expression vector to facilitate screening. The brightest colonies identified were subsequently cultured in liquid media until reaching an $OD_{600}$ of 0.5 and whole cell fluorescence spectra were obtained with a luminescence spectrophotometer.

Figure 13:
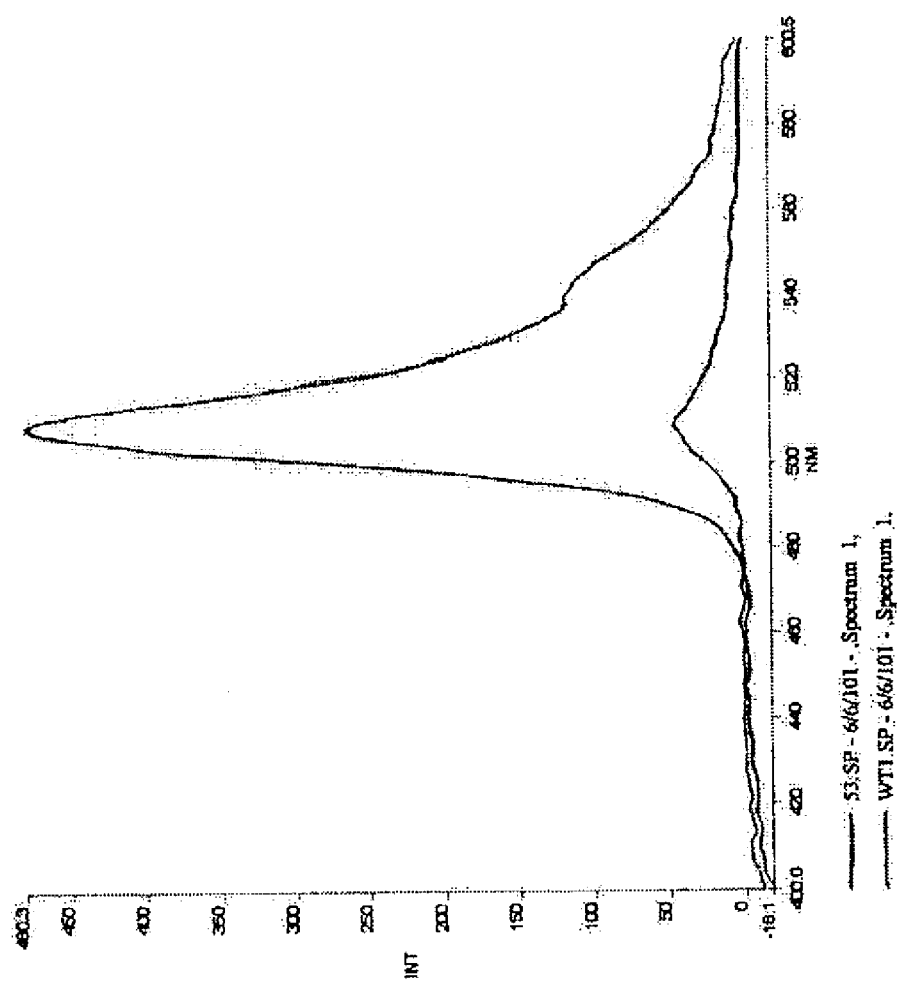
FIG. 13 shows the emission spectrum for wild type Green Fluoresence Protein (GFP) and GFP clone 53 after one round of FIND treatment.

GFP mutants with 10–30-fold improved fluorescence signals were identified by the above means. See FIG. 13. The mutant GFP genes were sequenced and the clone encoding the mutant GFP protein having the highest fluorescent signal was shown to include two novel mutations which resulted in amino acid changes I171V and Q184L. These amino acids have not previously been demonstrated to contribute significantly to an enhanced fluorescent signal.

Discussion

A novel method for directed evolution, designated FIND, is presented herein. The FIND technology utilizes exonucleases for fragmentation of DNA and the resulting DNA molecules are reassembled in two sequential PCR reactions. By definition, an exonuclease digests DNA from the ends and cleaves off one nucleotide at a time. Different exonucleases have different kinetics and different detailed mechanisms of digestion. As described hereinabove, these properties may be exploited to create fragments of all possible sizes. When combining two different genes, the influence of fragment size on recombination frequency is particularly important. Accordingly, as presented herein, recombination frequencies may be enhanced by utilizing optimal sets of fragments. Different fragment sets may be generated by varying the enzyme concentration and/or digestion times of the fragmentation step. A wider range of digestion times, for example, may be used to yield higher recombination frequencies if fragments of a particular size range are used to supplement the reaction. See FIG. 10B.

Moreover, a variety of different exonucleases may be used to advantage in the FIND process, especially when using single stranded DNA as the starting material. Enhanced frequencies of recombination were obtained when DNA fragments derived from treatment with different exonucleases were combined. See FIG. 12D.

The impact of genetic homology between genes on recombination frequency (11) and the frequency of homoduplex formation (12,13) during recombination processes have been investigated. Homoduplex formation, wherein genetic fragments from the same parental gene anneal to each other during the recombination process, tends to reduce the diversity of the resultant pool of recombinants. Utilization of restriction enzymes for the fragmentation step has been shown to increase the frequency of chimeric genes to almost 100% (12). The use of single stranded DNA and DNAse I fragmentation has also been shown to increase the frequency of chimeric genes from 1% to 14% as compared to double stranded DNA (13).

As presented herein, the frequency of chimeric genes produced using FIND technology was increased to 60% upon utilization of single stranded DNA as template. See FIGS. 11A and B. When recombining only two genes, FIND technology may be used to manipulate the genes separately throughout the experimental steps leading to the recombination step. This feature of the FIND procedure may be exploited to yield 100% chimeras.

A robust system is of critical importance in the creation of highly functional genetic libraries. A system that introduces random mutations (6,24) in an uncontrolled manner is not well suited for such applications because it may lead to the elimination of functional positive mutations introduced into the parental gene or introduce lethal mutations. In either event, such features would limit the utility of a genetic library generated with such a system.

The FIND system, as described herein, inherently possesses a high degree of fidelity and can be modified to accommodate the introduction of directed mutations. It is a highly controllable and robust method/technology that utilizes exonucleolytic fragmentation of DNA. Herein, a number of parameters that contribute significantly to the quality of the end-products (e.g., library of shuffled genes) generated using FIND technology were examined. These parameters include time of fragmentation, type of exonuclease, enzyme concentration, and type of template molecule used. Experiments in which these parameters were varied produced surprising results and provide an improved method for the generation of nucleic acids encoding proteins or peptides having altered biological and biochemical characteristics.

REFERENCES

1. Cadwell, R. C. and G. F. Joyce. 1992. PCR Methods Appl 2:28–33.
2. Cadwell, R. C. and G. F. Joyce. 1994. Mutagenic PCR. PCR Methods Appl 3:S136–140.
3. Chalfie, M., Y. Tu, G. Euskirchen, W. W. Ward and D. C. Prasher. 1994. Science 263:802–805.
4. Chen, K. and F. H. Arnold. 1993. Proc Natl Acad Sci USA 90:5618–5622.
5. Crameri, A., S. A. Raillard, E. Bermudez and W. P. Stemmer. 1998. Nature 391:288–291.
6. Crameri, A., E. A. Whitehorn, E. Tate and W. P. Stemmer. 1996. Nat Biotechnol 14:315–319.
7. Gibbs, M. D., K. M. Nevalainen and P. L. Bergquist. 2001. Gene 271:13–20.
8. Giver, L., A. Gershenson, P. O. Freskgard and F. H. Arnold. 1998. Proc Natl Acad Sci USA 95:12809–12813.
9. Hansson, L. O., R. Bolton-Grob, T. Massoud and B. Mannervik. 1999. J Mol Biol 287:265–276.
10. Henke, E. and U. T. Bornscheuer. 1999. Biol Chem 380:1029–1033.
11. Joern, J. M., P. Meinhold and F. H. Arnold. 2002. J Mol Biol 316:643–656.
12. Kikuchi, M., K. Ohnishi and S. Harayama. 1999. Gene 236:159–167.
13. Kikuchi, M., K. Ohnishi and S. Harayama. 2000. Gene 243:133–137.
14. Kong, X., Y. Liu, X. Gou, S. Zhu, H. Zhang, X. Wang and J. Zhang. 2001. Biochem Biophys Res Commun 289:137–142.
15. Liu, H. L., Y. Doleyres, P. M. Coutinho, C. Ford and P. J. Reilly. 2000. Protein Eng 13:655–659.
16. Lutz, S., M. Ostermeier and S. J. Benkovic. 2001. Nucleic Acids Res 29:E16.
17. May, O., P. T. Nguyen and F. H. Arnold. 2000. Nat Biotechnol 18:317–320.
18. Ostermeier, M., J. H. Shim and S. J. Benkovic. 1999. Nat Biotechnol 17:1205–1209.
19. Pelletier, J. N. 2001. Nat Biotechnol 19:314–315.
20. Schmidt-Dannert, C., D. Umeno and F. H. Arnold. 2000 Nat Biotechnol 18:750–753.
21. Shyur, L. F., A. E. Aleshin, R. B. Honzatko and H. J. Fromm. 1996. J Biol Chem 271:3005–3010.
22. Song, J. K. and J. S. Rhee. 2000. Appl Environ Microbiol 66:890–894.
23. Stemmer, W. P. 1994. Proc Natl Acad Sci USA 91:10747–10751.
24. Stemmer, W. P. 1994. Nature 370:389–391.
25. Wan, L., M. B. Twitchett, L. D. Eltis, A. G. Mauk and M. Smith. 1998. Proc Natl Acad Sci USA 95:12825–12831.
26. Volkov, A. A. and F. H. Arnold. 2000. Methods Enzymol 328:447–456.
27. Zhao, H. and F. H. Arnold. 1999. Protein Eng 12:47–53.
28. Zhao, H., L. Giver, Z. Shao, J. A. Affholter and F. H. Arnold. 1998. Nat Biotechnol 16:258–261.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for generating a polynucleotide sequence or population of sequences, comprising the steps of
   a) digesting parent polynucleotide sequences encoding one or more protein motifs with at least one exonuclease to generate at least one population of fragments, wherein said digesting with at least one exonuclease comprises digesting a first parent polynucleotide sequence with a first exonuclease to produce a first population of fragments and digesting a second parent polynucleotide sequence with a second exonuclease to produce a second population of fragments;
   b) contacting said first and second population of fragments, wherein said fragments of said first and second population of fragments anneal;
   c) amplifying the annealed fragments of step b) to generate at least one polynucleotide sequence encoding one or more protein motifs having altered characteristics as compared to the one or more protein motifs encoded by said parent polynucleotide sequences,
   wherein in step (a) at least one parameter of the reaction used for digestion of the first parent polynucleotide sequence is different from the equivalent parameter(s) used in the reaction for digestion of the second parent polynucleotide sequence.

2. A method according to claim 1 wherein the reaction parameter is selected from exonuclease type, exonuclease concentration, reaction volume, duration of the digestion reaction, temperature of the reaction mixture, pH of the reaction mixture, length of parent single stranded polynucleotide sequences, the amount of single stranded polynucleotide molecules and the buffer composition of the reaction mixture.

3. A method according to claim 1, wherein the at least one parent polynucleotide sequence is double-stranded and the method further comprises the step of generating single-stranded plus and minus strand polynucleotide sequence from said double-stranded fragments prior to step a).

4. A method according to claim 3, wherein said single-stranded plus and minus strand polynucleotide sequences are isolated to generate a plus strand population and a minus strand population prior to step a).

5. A method according to claim 1, wherein the at least one parent polynucleotide sequence is single-stranded.

6. A method according to claim 1, wherein the first parent polynucleotide is at least one single-stranded plus polynucleotide sequence and the second parent polynucleotide is at least one single-stranded minus polynucleotide sequence.

7. A method according to claim 3 wherein the single-stranded plus polynucleotide sequence is digested with a first exonuclease to produce a first population of single-stranded plus fragments and the single-stranded minus polynucleotide sequence is digested with a second exonuclease to produce a second population of single-stranded minus fragments.

8. A method according to claim 1 wherein the first and second exonuclease are the same.

9. A method according to claim 1 wherein the first and second exonuclease are different.

10. A method according to claim 1, wherein the at least one parent polynucleotide sequence has been subjected to mutagenesis.

11. A method according to claim 1, wherein the population of fragments generated in step b) is subjected to mutagenesis.

12. A method according to claim 10, wherein the mutagenesis is error prone mutagenesis.

13. A method according to claim 1, wherein said first and second exonuclease are selected from the group consisting of BAL31, Exonuclease I, Exonuclease V, Exonuclease VII, T7 gene 6, and RecJ exonuclease.

14. A method according to claim 1, wherein said first parent polynucleotide sequence is digested with said first exonuclease for a first incubation time to produce a first population of fragments and said second parent polynucleotide sequence is digested with said second exonuclease for a second incubation time to produce a second population of fragments.

15. A method according to claim 14, wherein said first and second incubation time are the same.

16. A method according to claim 14, wherein said first and second incubation time are different.

17. A method according to claim 1, further comprising digesting a third parent polynucleotide sequence with a third exonuclease to produce a third population of fragments and contacting said third population of fragments to said first and second population of fragments in step b), wherein said fragments of said first, second, and third population of fragments anneal.

18. A method according to claim 1 wherein at least one parent polynucleotide sequence encodes an antibody or fragment thereof.

19. A method according to claim 1 wherein at least one parent polynucleotide sequence encodes an enzyme.

20. A method according to claim 1 further comprising the step of screening the at least one polynucleotide generated in step c) for desired characteristics.

21. A method according to claim 1 further comprising the step of expressing the at least one polynucleotide generated in step c) and screening the resulting polypeptide for desired characteristics.

22. A method according to claim 1, wherein the exonuclease concentration used for digestion of the first population of single stranded polynucleotide molecules is different from the exonuclease concentration used for digestion of the second population of single stranded polynucleotide molecules.

23. A method according to claim 1, wherein the reaction volume used for digestion of the first population of single stranded polynucleotide molecules is different from the reaction volume used for digestion of the second population of single stranded polynucleotide molecules.

24. A method according to claim 1, wherein the temperature of the reaction mixture used for digestion of the first population of single stranded polynucleotide molecules is different from the temperature of the reaction mixture used for digestion of the second population of single stranded polynucleotide molecules.

25. A method according to claim 1, wherein the pH of the reaction mixture used for digestion of the first population of single stranded polynucleotide molecules is different from the pH of the reaction mixture used for digestion of the second population of single stranded polynucleotide molecules.

26. A method according to claim 1, wherein the length of the polynucleotides in the first population of single stranded polynucleotide molecules is different from the length of the polynucleotides in the second population of single stranded polynucleotide molecules.

27. A method for preparing a pharmaceutical composition which comprises, identifying of a polynucleotide with desired characteristics as claimed in claim 1 and adding said polynucleotide to a pharmaceutically acceptable carrier.

28. The method of claim 27, wherein said polynucleotide is translated into a polypeptide having desired characteristics and said polypeptide is added to a pharmaceutically acceptable carrier.

29. A process which comprises, following the identification of a polynucleotide by the method of claim 1, the manufacture of that polynucleotide, in whole or in part, optionally in conjunction with an additional polynucleotide sequence.

30. The method according to claim 28 wherein the polypeptide is an antibody or fragment thereof.

31. The method according to claim 28 wherein the polypeptide is an enzyme.

32. A method of detecting and/or amplifying a target polynucleotide in a sample comprising contacting said sample with a polynucleotide having been identified by a method according to claim 1, said identified polynucleotide optionally being conjugated with an additional polynucleotide sequence.

33. A method as claimed in claim 1, wherein a plurality of populations of single stranded fragments of varying lengths are generated following digestion in step a).

34. A method according to claim 33, wherein said digestion is controlled to generate a population of single-stranded fragments having an average length of more than approximately 50 nucleotides.

35. A method for making a polypeptide having desired properties, the method comprising the following steps:
   (a) generating variant forms of a parent polynucleotide as claimed in claim 1;
   (b) expressing the variant polynucleotides produced in step (a) to produce variant polypeptides;
   (c) screening the variant polypeptides for desired properties; and
   (d) selecting a polypeptide having desired properties from the variant polypeptides.

* * * * *